(12) United States Patent
Brouillette et al.

(10) Patent No.: US 6,727,237 B2
(45) Date of Patent: Apr. 27, 2004

(54) INHIBITORS OF BACTERIAL NAD SYNTHETASE

(76) Inventors: Wayne J. Brouillette, 328 Kings Crest La., Pelham, AL (US) 35124; Donald Muccio, 3531 Atdoann Dr., Hoover, AL (US) 35226; Mark J. Jedrzejas, 1800 Trail Ridge Dr., Pelham, AL (US) 35124-1017; Christie G. Brouillette, 328 Kings Crest La., Pelham, AL (US) 35124; Yancho Devedjiev, 890 Old Brook Rd., Charlottesville, VA (US) 22901; Walter Cristofoli, 2115-G 17$^{th}$ Ave. South, Birmingham, AL (US) 35205; Lawrence J. DeLucas, 2739 Altadena Rd., Birmingham, AL (US) 35243; Jose Gabriel Garcia, An der Rehwiese 15, D-81375 Munich (DE); Laurent Schmitt, 44, rue Rogg Haas, 68510 Sierentz (FR); Sadanadan E. Velu, 711 Stonebridge Rd., Birmingham, AL (US) 35209

( * ) Notice: Subject to any disclaimer, the term of this patent is extended or adjusted under 35 U.S.C. 154(b) by 0 days.

(21) Appl. No.: 10/281,407

(22) Filed: Oct. 25, 2002

(65) Prior Publication Data

US 2004/0063758 A1 Apr. 1, 2004

Related U.S. Application Data

(60) Division of application No. 09/617,258, filed on Jul. 14, 2000, now Pat. No. 6,500,852, which is a continuation of application No. PCT/US99/14839, filed on Jun. 30, 1999, which is a continuation-in-part of application No. PCT/US99/00810, filed on Jan. 14, 1999.
(60) Provisional application No. 60/097,880, filed on Aug. 25, 1998, and provisional application No. 60/071,399, filed on Jan. 14, 1998.

(51) Int. Cl.$^7$ .................... A61K 31/44; C07D 209/04; C07D 213/02; C07D 213/20
(52) U.S. Cl. .................. 514/183; 514/354; 514/356; 514/358; 514/415; 514/357; 546/1; 546/329; 546/318; 546/339; 546/347; 548/469; 548/509; 548/518
(58) Field of Search .................. 514/183, 354, 514/356, 357, 358, 415; 546/1, 329, 318, 339, 347; 548/469, 509, 518

(56) References Cited

U.S. PATENT DOCUMENTS

| | | | |
|---|---|---|---|
| 4,275,068 A | 6/1981 | Thiele et al. | 424/266 |
| 4,289,777 A | 9/1981 | Albrecht et al. | 424/258 |
| 4,616,008 A | * 10/1986 | Hirai et al. | 514/200 |
| 4,767,712 A | 8/1988 | Motal et al. | 435/253 |
| 4,797,358 A | 1/1989 | Misaki et al. | 435/176 |
| 4,859,692 A | 8/1989 | Bernstein et al. | 514/281 |
| 4,921,786 A | 5/1990 | Takahashi et al. | 435/4 |
| 5,013,743 A | 5/1991 | Iwahi et al. | 514/338 |
| 5,093,342 A | 3/1992 | Tomoi et al. | 514/328 |
| 5,206,146 A | 4/1993 | Misaki et al. | 435/16 |
| 5,468,768 A | 11/1995 | Cipollina et al. | 324/718 |
| 5,521,197 A | 5/1996 | Audia | 514/323 |
| 5,583,149 A | 12/1996 | Cipollina et al. | 514/339 |
| 5,589,349 A | 12/1996 | Shinzaki et al. | 435/26 |
| 5,622,953 A | 4/1997 | Janssen et al. | 514/255 |
| 5,639,752 A | 6/1997 | Maco | 514/245 |
| 5,659,040 A | 8/1997 | Blatcher et al. | 546/185 |
| 5,708,008 A | 1/1998 | Audia et al. | 514/323 |
| 5,744,488 A | 4/1998 | Cross et al. | 514/334 |
| 5,786,473 A | 7/1998 | Blatcher et al. | 546/277 |
| 5,834,493 A | 11/1998 | Gil Quintero et al. | 514/334 |
| 5,849,764 A | 12/1998 | Goulet et al. | 514/332 |
| 5,932,743 A | 8/1999 | Collini et al. | 548/508 |
| 5,936,098 A | 8/1999 | Yasuda et al. | 548/465 |
| 5,962,474 A | 10/1999 | Audia et al. | 514/323 |
| 5,965,582 A | 10/1999 | Lebaut et al. | 514/338 |
| 5,977,154 A | 11/1999 | Bell et al. | 514/394 |
| 5,981,525 A | 11/1999 | Farina et al. | 514/235.2 |
| 5,981,550 A | 11/1999 | Goulet et al. | 514/333 |
| 5,981,776 A | 11/1999 | Diaz et al. | 549/462 |
| 5,990,150 A | 11/1999 | Matsui et al. | 514/415 |
| 5,998,438 A | 12/1999 | Slassi et al. | 514/316 |
| 6,022,880 A | 2/2000 | Effland et al. | 514/339 |
| 6,037,123 A | 3/2000 | Benton et al. | 435/6 |
| 6,046,136 A | 4/2000 | James et al. | 504/246 |
| 6,174,873 B1 | 1/2001 | Wrenn, Jr. | 514/45 |
| 6,187,541 B1 | 2/2001 | Benton et al. | 435/6 |
| 6,228,588 B1 | 5/2001 | Benton et al. | 435/6 |
| 6,339,073 B1 | 1/2002 | Pero | 514/47 |

FOREIGN PATENT DOCUMENTS

| | | |
|---|---|---|
| EP | 0 090 405 | 10/1983 |
| EP | 0 196 530 | 3/1985 |
| EP | 0 196 530 A | 10/1986 |
| EP | A-0268956 | 1/1988 |
| EP | 0 585722 | 3/1994 |
| WO | WO 99 36422 A | 7/1999 |
| WO | WO 00 10996 A | 3/2000 |

OTHER PUBLICATIONS

Cho, Young Ho, Chemical Abstract DN 78:66798, also cited as Han'guk Saenghwa Hakhoechi, 5/1,1–13(1972).*

Brouillette et al., "Synthesis of Inhibitors of Prokaryotic NAD Synthetase" American Chemical Society. Abstracts of paper. At the National Meeting, American Chemical Society, Washington, DC, US, vol. 218, No. Part 1, Aug. 22, 1999, pp. 295–MEDI, XP000981304 ISSN: 0065–7727 the whole document.

(List continued on next page.)

Primary Examiner—Mukund J. Shah
Assistant Examiner—Sudhaker B. Patel
(74) Attorney, Agent, or Firm—Womble Carlyle Sandridge & Rice PLLC

(57) ABSTRACT

The present invention provides methods of synthesizing and screening inhibitors of bacterial NAD synthetase enzyme, compounds thereof, and methods of treating bacterial and microbial infections with inhibitors of bacterial NAD synthetase enzyme.

17 Claims, No Drawings

OTHER PUBLICATIONS

Brouillette et al., "Synthesis of Inhibitors of Prokaryotic NAD Synthetase", Abstract #295, Divisional of Medicinal Chemistry, 218$^{th}$ National American Chemical Society Meeting, New Orleans, LA, Aug. 22–26, 1999 (Abstract only).

Brouillette et al., Synthesis of NAD Synthetase Inhibitors as Potential Antibacterial Agents, Abstract #298, Division of Medicinal Chemical, 218$^{th}$ National American Chemical Society Meeting, New Orleans, LA, Aug. 22–26, 1999 (Abstract only).

Cristofoli et al., "The Synthesis of Tethered Heterocyclic Dimers as Inhibitors of NAD Synthetase", Gordon Research Conference on Heterocyclic Chemistry, New Port, Rhode Island, Jun. 28–Jul. 3, 1998 ("Title only").

Cristofoli et al., "The Synthesis of Tethered Heterocyclic Dimers as Inhibitors of NAD Synthetase", Poster presentation, Gordon Research Conference on Heterocyclic Compounds, 1998, Newport, RI (Abstract only).

Fostel et al., "Comparison of responses of DNA topoisomerase I from Candida albicans and human cells to four new agents which stimulate toposiomerase–dependent DNA nicking", FEMS Microbiology Letters vol. 138, 1996, pp. 105–111.

Fostel et al., "Identification of the Aminocatechol A–3253 as an in Vitro Poison of DNA Topoisomerase I from Candida albicans", Antimicrobial Agents and Chemotherapy, vol. 39, No. 3, Mar. 1995, pp. 586–592.

Garcia et al., "Combinatorial Synthesis of NAD Synthetase Inhibitors", Abstract #297, division of Medicinal Chemistry, 218$^{th}$ National American Chemical Society Meeting, New Orleans, Louisiana, Aug. 22–26, 1999 ("Title only").

Garcia et al., "Synthesis of Potential NAD Synthetase Inhibitors as Antibacterial Agents", Division of Medicinal Chemistry, American Chemical Society National Meeting, Boston, Massachusetts, Aug. 23–27, 1998 ("Title only").

Garcia et al., "Synthesis of Potential NAD Synthetase Inhibitors as Antibacterial Agents" American Chemical Society (Abstracts). National Meeting, American Chemical Society, Washington, DC, US, vol. 216, No. Part 2, Aug. 23, 1998, pp. 248–MEDI, XP000979956 ISSN: 0065-7727.

Groll et al., "Potential new antifungal agents", Current Opinion in Infectious Diseases, vol. 10, 1997, pp. 449–458.

Kauffman et al., "Antifungal Agents in the 1990s", Drugs, 53(4), Apr. 1997, pp. 539–549.

Merck Index 1954, p. 1030, compound No. 6434: Nocotine.

Monk et al. "Fungal Plasma Membrane Proton Pumps as Promising New Antifungal Targets", Critical Reviews in Microbiology, 20(3), 1994, pp. 209–223.

Monk et al., Targeting the fungal plasma membrane proton pump: Acta Biochimica Polonica, vol. 42, No. 4, 1995, pp. 481–496.

Nafsika H. Georgopapadakou, "Antifungals: mechanism of action and resistance, established and novel drugs", Current Opinion in Microbiology, vol. 1, 1998, pp. 547–457.

Richardson, "Fluconazole, An Orally Active Antifungal Agent", Medicinal Chemistry, 2$^{nd}$ Edition, Academic Press, San Diego, CA 1993.

Rizzi et al., "A novel deamido–NAD+–binding site revealed by the trapped NAD–adenylate intermediate in the NAD+ synthetase structure", Structure, vol. 6, No. 9, 1998, pp. 1129–1140.

Rizzi et al., "Crystal structure of NC$_3$–dependent NAD+ synthetase from Bacillus subtillis", The EMBO Journal, vol. 15, No. 19, 1996, pp. 5125–5134.

Schmitt et al., "The Synthesis of Tethered Heterocyclic Dimers as Inhibitors of NAD Synthetase", Division of Medicinal Chemistry, American Chemical Society National Meeting, Boston, Massachusetts, Aug. 23–27, 1998 ("Title only").

Schmitt et al., "The Synthesis of Tethered Heterocyclic Dimers as Inhibitors of NAD Synthetase", Abstracts of Papers on the American Chemical Society, vol. 216, part 2, pp. 247–MEDI, Aug. 23, 1998.

Shibata et al.: "Effects of dietary orotic acid on the levels of liver and blood NAD in rats" Journal of Nutritional Science and Vitaminology., vol. 31, No. 3, 1985, pp. 265–278, XP001064472 XX, XX p. 265, Summary p. 276, paragraph 1.

Shibata et al.: "Effect of dietary paraquat on the enzyme activities involved in tryptophan–niacin metabolism in rats" Agricultural and Biological Chemistry, vol. 52, No. 7, 1988, pp. 1857–1858 XP002193914 Japan Soc. For Bioscience Biotechnology and Agrochem. Tokyo., JP ISSN: 0002–1369 p. 1857, col. 2, line 20—line 23 p. 1858; table 1.

Shridhar et al., "Antimicrobial Agents—Part III+: Synthesis and Antimicrobial Activity of Some New Aryloxyalkyl Esters of 3–Ally/methyl/chloro–4–Hydroxybenzoic Acids", J. Indian Chem. Soc., vol. LVI, Jan. 1979, pp. 74–76.

Shridhar et al., "Antimicrobial Agents: Synthesis and Antimicrobial Activity of New Aryloxyalkyl Esters of p–Hydroxybenzoic Acid", Journal of Pharmaceutical Sciences, vol. 65, No. 7, Jul. 1976, pp. 1074–1078.

Turner et al.: "Production of slaughter steers from forages in the arid west" Journal of Animal Science, vol. 44, No. 5, 1977, pp. 901–907, XP001064470 New York, NY, US ISSN: 0021–8812 p. 905, col. 2, last paragraph–p. 906, col. 1, paragraph 2.

Weinberg, "Antifungal Agents", Principles of Medicinal Chemistry, 4$^{th}$ Edition: Williams & Wilkins, Media, PA, Chapter 35, 1995, pp, 803.

Yu et al., "Purification and Properties of Yeast Nicotinamide Adenine Dinucleotide Synthetase", The Journal of Biological Chemistry, vol. 247, Issue of Aug. 10, 1972, pp. 4794–4802.

* cited by examiner

INHIBITORS OF BACTERIAL NAD SYNTHETASE

CROSS-REFERENCE TO RELATED APPLICATIONS

This application is a divisional of application Ser. No. 09/617,258 filed on Jul. 14, 2000 now U.S. Pat. No. 6,500,852, which is a continuation of PCT/US98/14839 filed on Jun. 30, 1999, which is a Continuation-in-Part of International Application No. PCT/US99/00810, filed Jan. 14, 1999 which claims priority to United States provisional application Ser. No. 60/097,880 filed on Aug. 25, 1998 and to United States provisional application Ser. No. 60/071,399 filed on Jan. 14, 1998. The contents of each of these referenced patent applications are herein incorporated by this reference in their entireties.

STATEMENT AS TO FEDERALLY SPONSORED RESEARCH

This invention was made, at least in part, with a government grant from DARPA. The U.S. government may have certain rights in this invention.

GOVERNMENT INTEREST STATEMENT

Some research that contributed to the invention herein was supported, in part, by a grant from the United States Department of Defense, Advanced Research Projects Agency.

FIELD OF THE INVENTION

The present invention pertains to antibacterial and antimicrobial agents, in particular, the present invention provides methods of synthesizing and screening compounds that are bacterial nicotinamide adenine dinucleotide (NAD) synthetase enzyme inhibitors. The present invention also provides novel compounds that inhibit bacterial NAD synthetase enzyme. The invention also provides libraries of compounds that comprise bacterial NAD synthetase enzyme inhibitors. Further, the present invention provides compounds that exhibit therapeutic activity as antibacterial agents, antimicrobial agents and broad spectrum antibiotics. Still further, the invention provides methods of treating a mammal with bacterial NAD synthetase enzyme inhibitor compounds. The present invention also provides novel disinfecting agents.

BACKGROUND OF THE INVENTION

Drug-resistant infectious bacteria, that is, bacteria that are not killed or inhibited by existing antibacterial and antimicrobial compounds, have become an alarmingly serious worldwide health problem. (E. Ed. Rubenstein, *Science*, 264, 360 (1994)). In fact, a number of bacterial infections may soon be untreatable unless alternative drug treatments are identified.

Antimicrobial or antibacterial resistance has been recognized since the introduction of penicillin nearly 50 years ago. At that time, penicillin-resistant infections caused by *Staphylococcus aureus* rapidly appeared. Today, hospitals worldwide are facing unprecedented crises from the rapid emergence and dissemination of microbes resistant to one or more antimicrobial and antibacterial agents commonly in use today. As stated in the Fact Sheet on Antimicrobial Resistance of the National Institute of Allergy and Infectious Diseases, National Institutes of Health, several strains of antibiotic-resistant bacteria are now emerging and are becoming a threat to human and animal populations, including those summarized below:

1) Strains of *Staphylococcus aureus* resistant to methicillin and other antibiotics are endemic in hospitals. Infection with methicillin-resistant *S. aureus* (MRSA) strains may also be increasing in non-hospital settings. Vancomycin is the only effective treatment for MRSA infections. A particularly troubling observation is that *S. aureus* strains with reduced susceptibility to vancomycin have emerged recently in Japan and the United States. The emergence of vancomycin-resistant strains would present a serious problem for physicians and patients.

2) Increasing reliance on vancomycin has led to the emergence of vancomycin-resistant enterococci (VRE), bacteria that infect wounds, the urinary tract and other sites. Until 1989, such resistance had not been reported in U.S. hospitals. By 1993, however, more than 10 percent of hospital-acquired enterococci infections reported to the Centers for Disease Control ("CDC") were resistant.

3) *Streptococcus pneumoniae* causes thousands of cases of meningitis and pneumonia, as well as 7 million cases of ear infection in the United States each year. Currently, about 30 percent of *S. pneumoniae* isolates are resistant to penicillin, the primary drug used to treat this infection. Many penicillin-resistant strains are also resistant to other antimicrobial or antibacterial drugs.

4) Strains of multi-drug resistant tuberculosis (MDR-TB) have emerged over the last decade and pose a particular threat to people infected with HIV. Drug-resistant strains are as contagious as those that are susceptible to drugs. MDR-TB is more difficult and vastly more expensive to treat, and patients may remain infectious longer due to inadequate treatment. Multi-drug resistant strains of *Mycobacterium tuberculosis* have also emerged in several countries, including the U.S.

5) Dianheal diseases cause almost 3 million deaths a year, mostly in developing countries, where resistant strains of highly pathogenic bacteria such as *Shigella dysenteriae*, Campylobacter, *Vibrio cholerae, Escherichia coli* and Salmonella are emerging. Furthermore, recent outbreaks of Salmonella food poisoning have occurred in the United States. A potentially dangerous "superbug" known as *Salmonella typhimurium*, resistant to ampicillin, sulfa, streptomycin, tetracycline and chloramphenicol, has caused illness in Europe, Canada and the United States.

In addition to its adverse effect on public health, antimicrobial or antibacterial resistance contributes to higher health care costs. Treating resistant infections often requires the use of more expensive or more toxic drugs and can result in longer hospital stays for infected patients. The Institute of Medicine, a part of the National Academy of Sciences, has estimated that the annual cost of treating antibiotic resistant infections in the United States may be as high as $30 billion.

Given the above, it would be highly desirable to develop novel antibacterial and antimicrobial agents that act by different mechanisms than those agents in use currently. Further, it would be desirable to be able to synthesize such novel compounds. It would also be desirable to develop libraries of compounds that exhibit inhibitory bacterial NAD synthetase activity. Such new agents would be useful to counteract antibiotic resistant strains of bacteria and other types of harmful microbes. It would be even more desirable to develop antibacterial agents that inhibit or block essential bacterial metabolic mechanisms, to result in bacterial death or deactivation, without also affecting the essential metabolic activities of a mammalian host. That is, it would be desirable to develop antibacterial agents that preferentially attack bacteria and other microbes and kill or deactivate the harmful organism without causing any attendant undesirable side effects in a human or animal patient. It would also be desirable to develop methods of rapidly screening potential new antimicrobial and antibacterial agents. It would also be desirable to develop novel disinfecting agents.

SUMMARY OF THE INVENTION

In one aspect, the invention provides a NAD synthetase inhibitor compound of the formula:

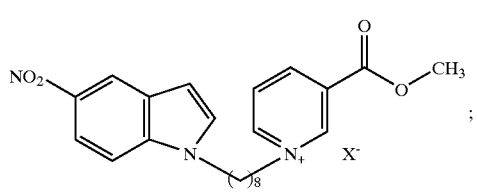
13

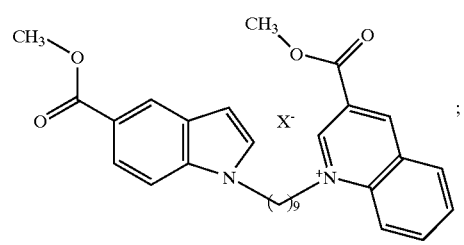
174

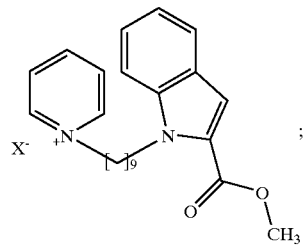
182

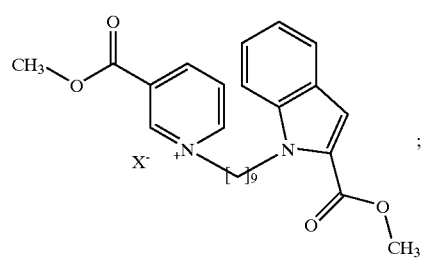
190

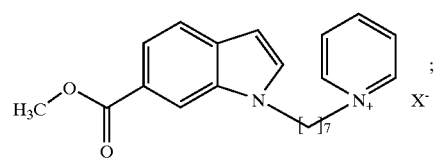
213

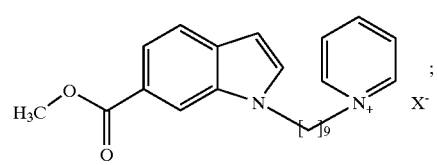
214

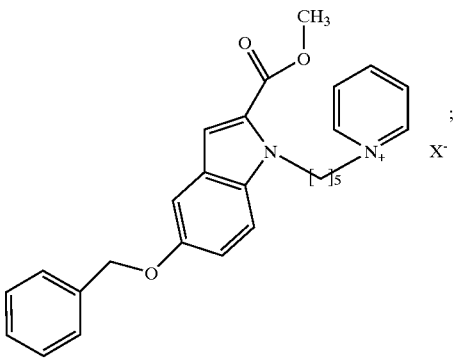
228

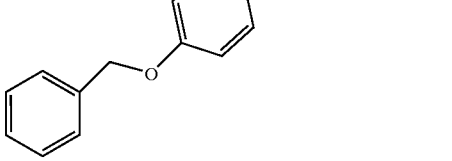
229

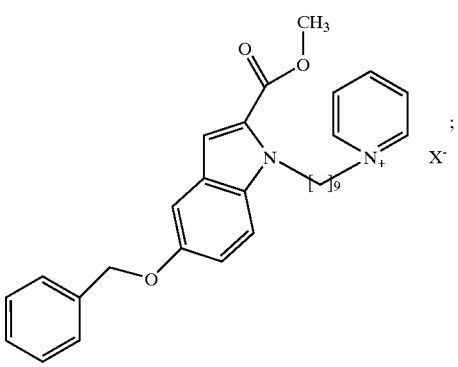
230

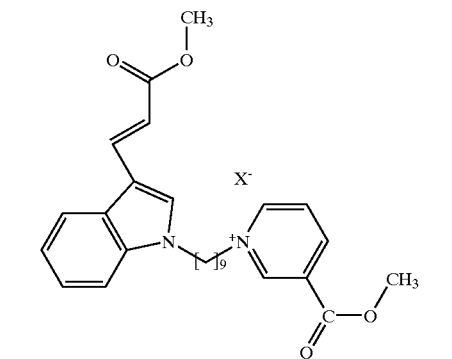
270

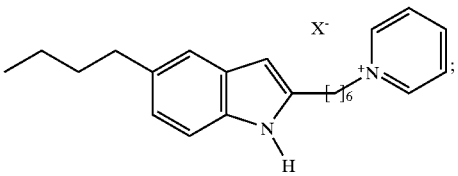
315

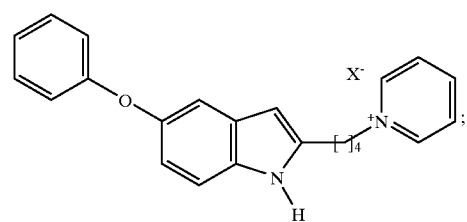
349
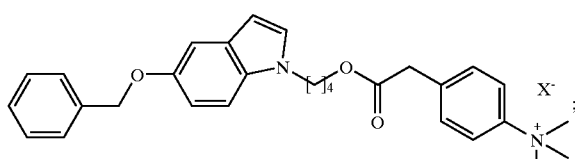
745
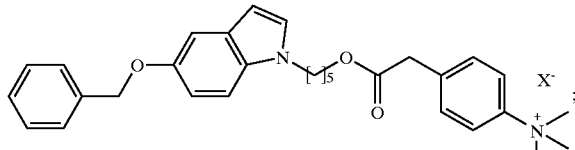
746
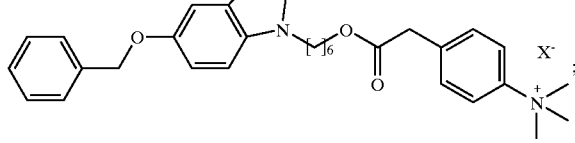
747
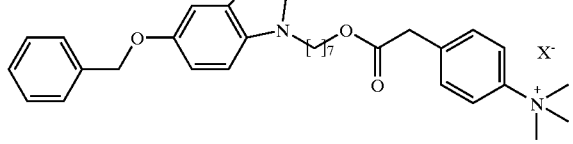
748
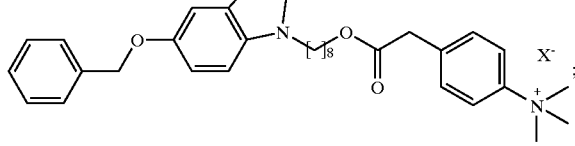
749
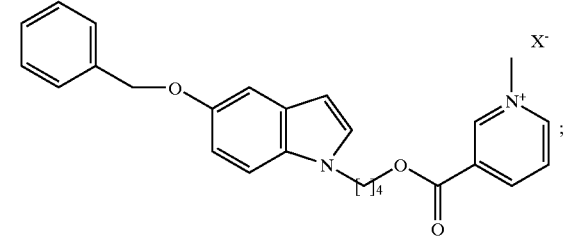
765
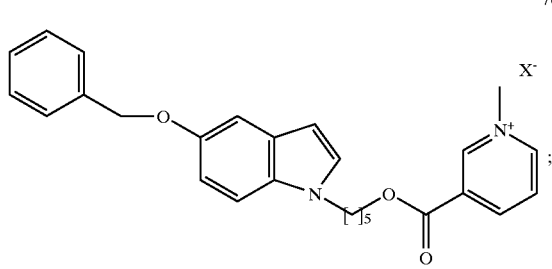
766
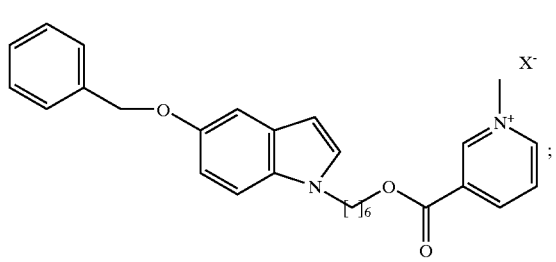
767
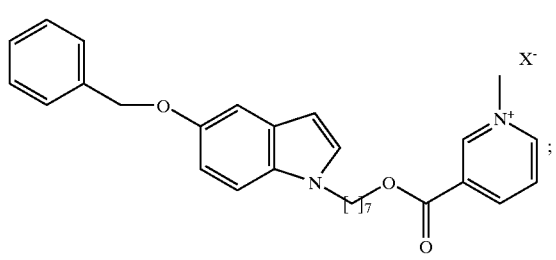
768
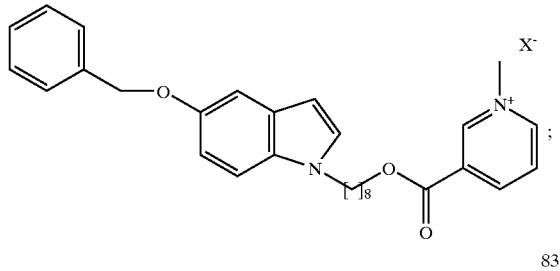
769
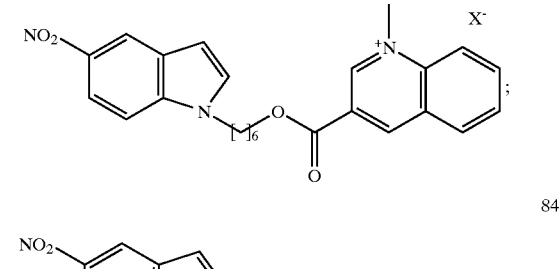
832
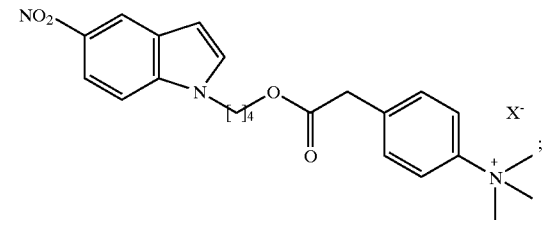
848

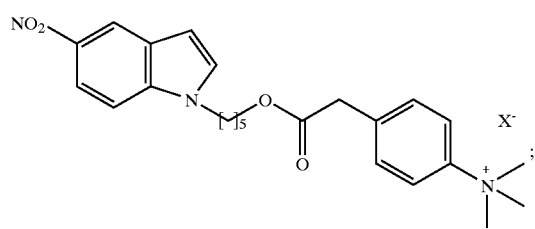
849
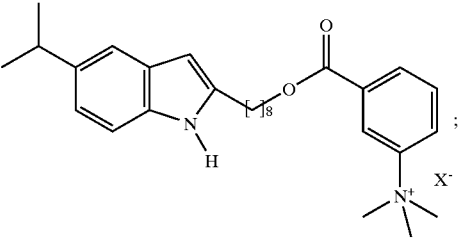
876
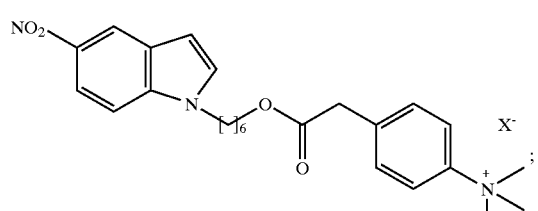
850
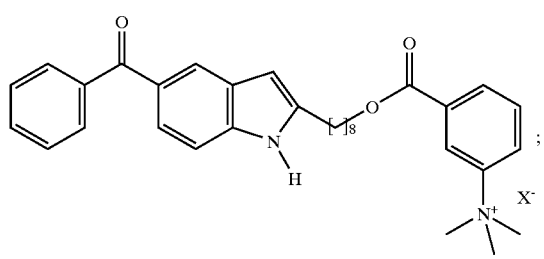
878
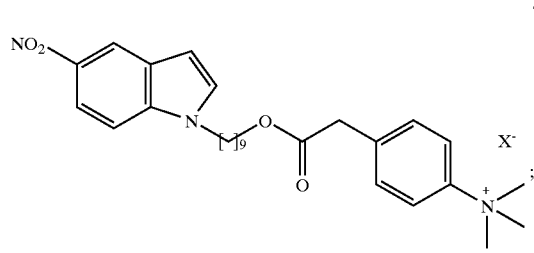
853
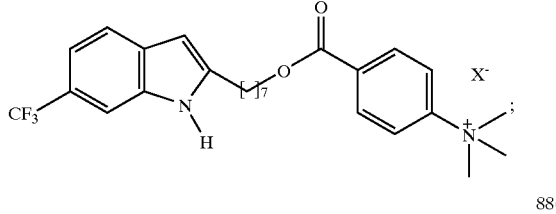
879
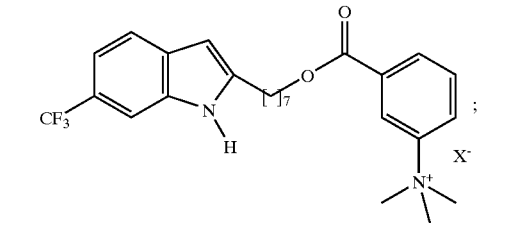
869
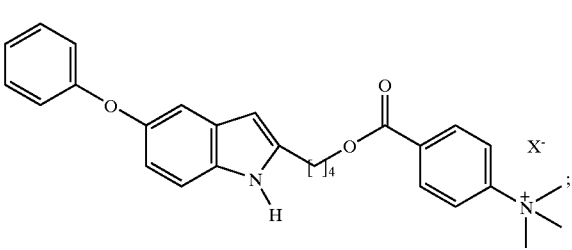
882
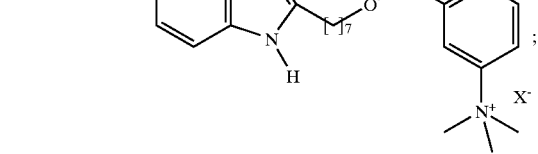
872
884
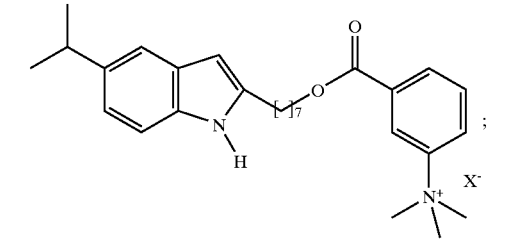
875
886

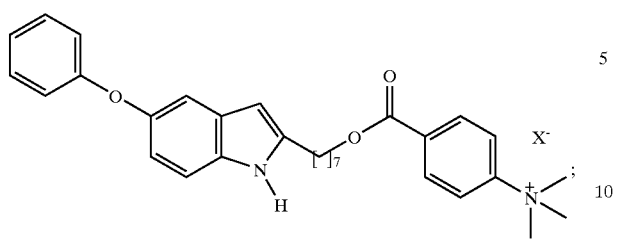
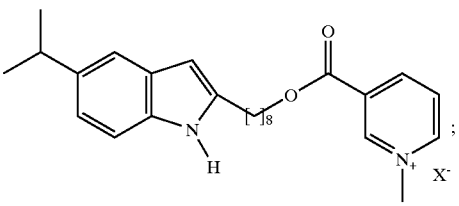
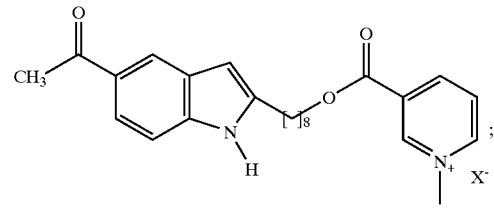
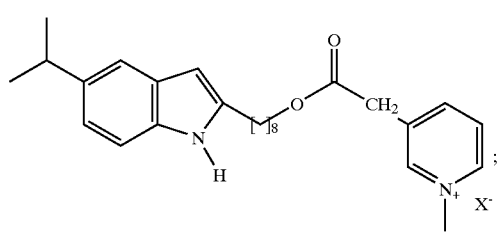
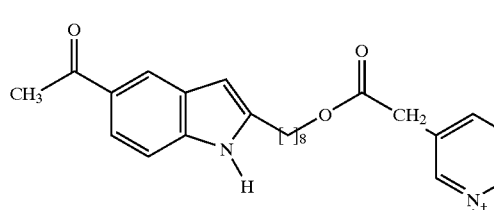
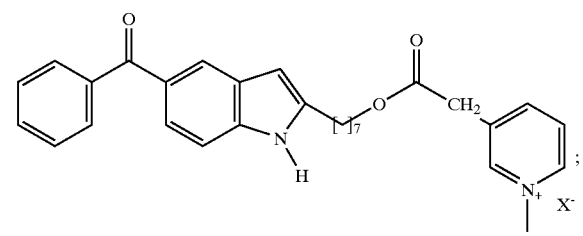
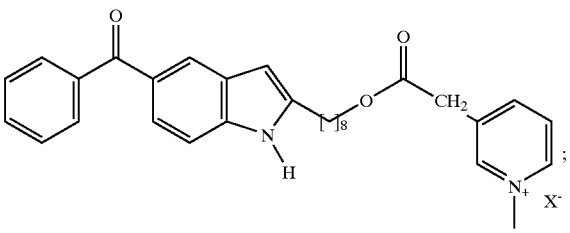
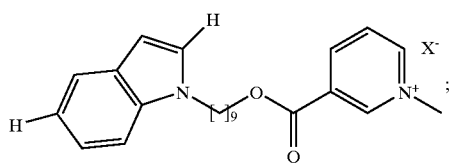

Still further, the invention provides a bacterial NAD synthetase enzyme inhibitor compound of the structure:
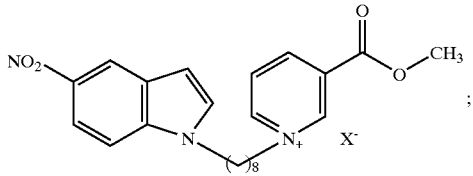
13
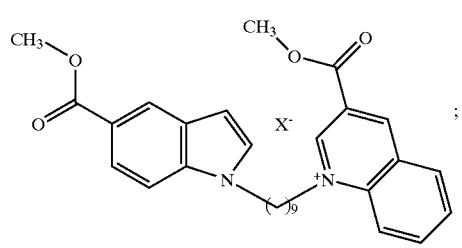
174
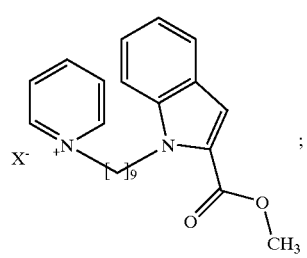
182
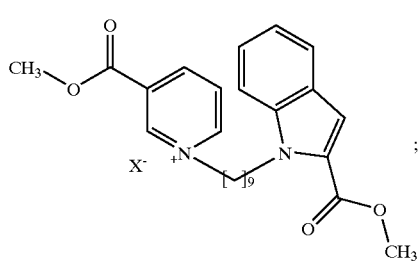
190
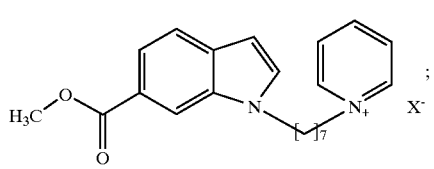
213
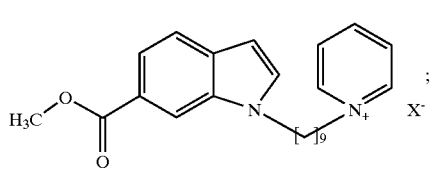
214
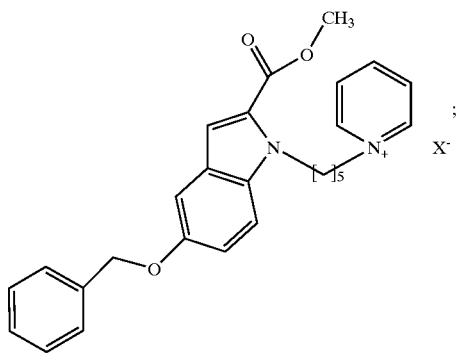
228
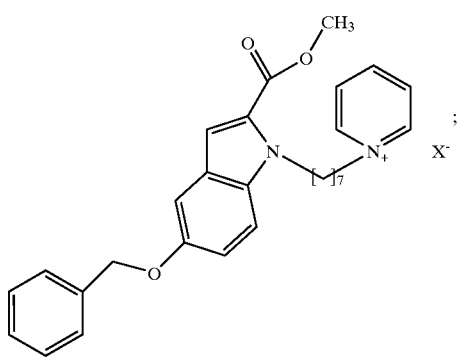
229
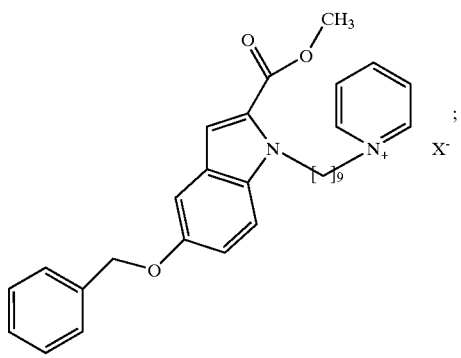
230
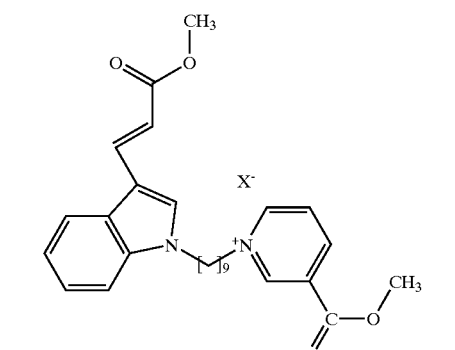
270
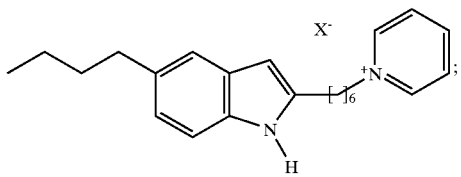
315

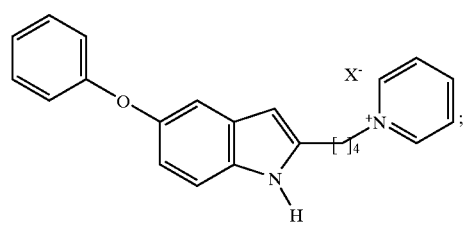
349
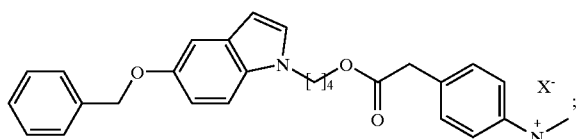
745
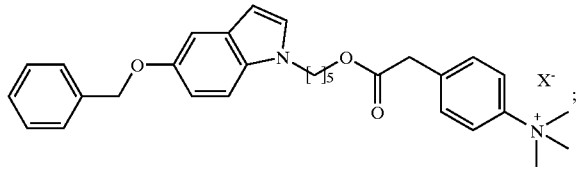
746
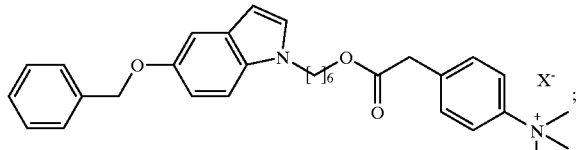
747
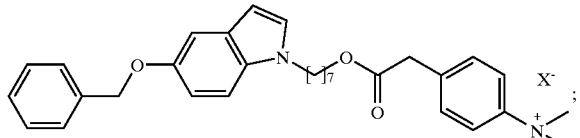
748
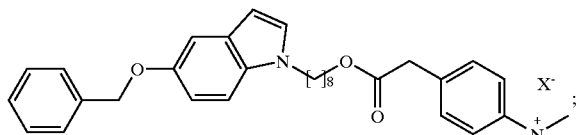
749
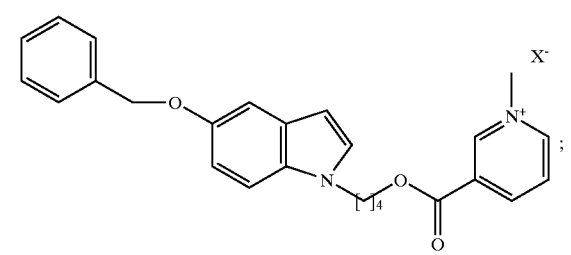
765
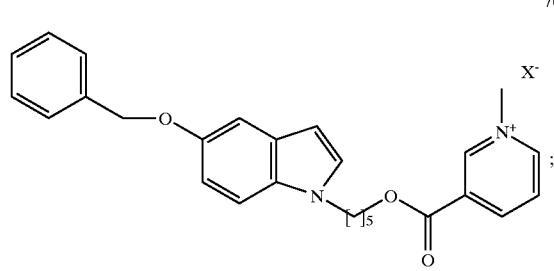
766
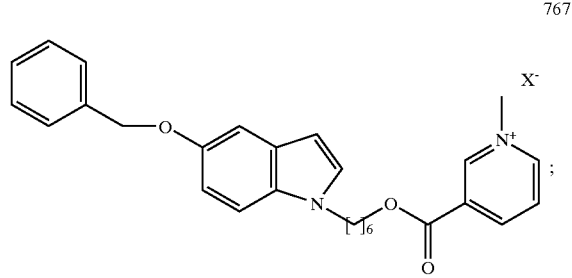
767
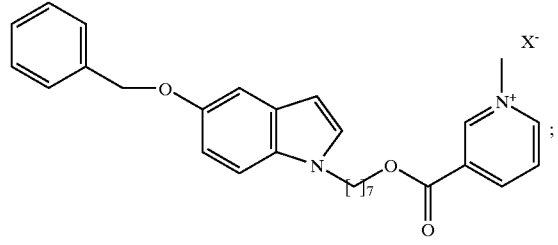
768
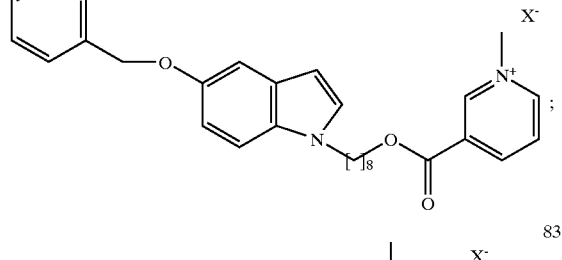
769
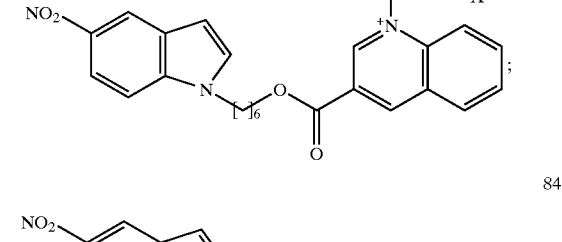
832
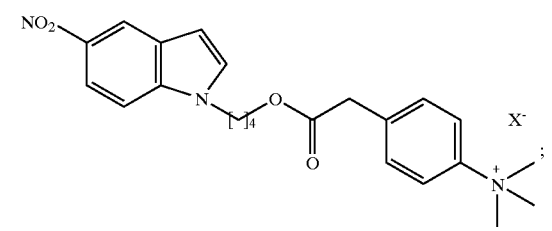
848

849
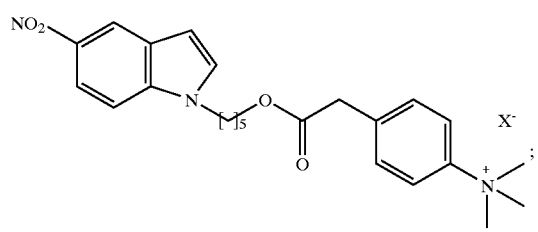
876
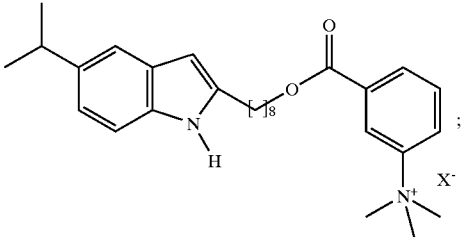
850
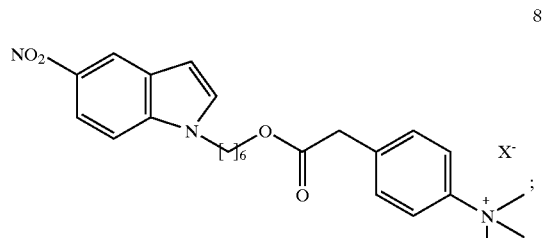
878
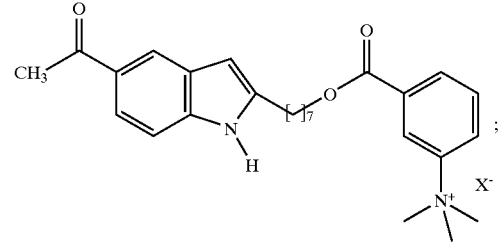
853
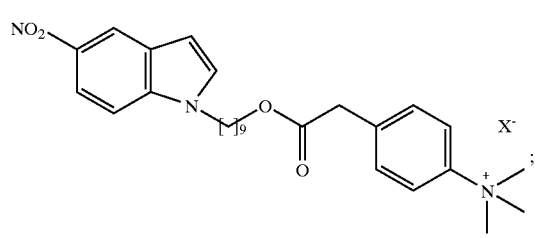
879
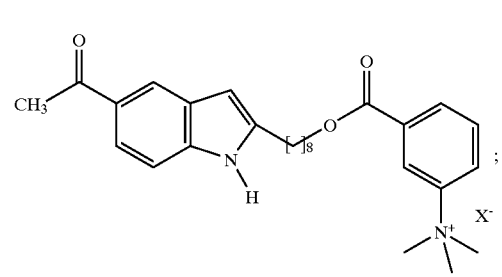
869
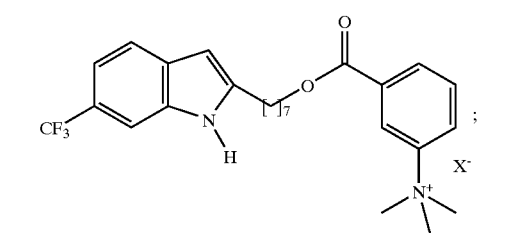
882
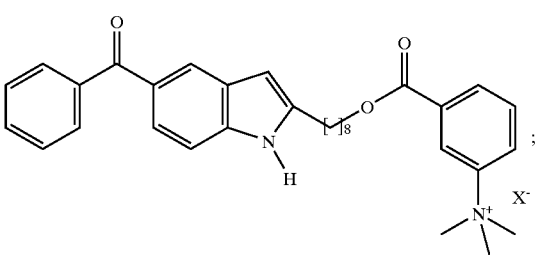
872
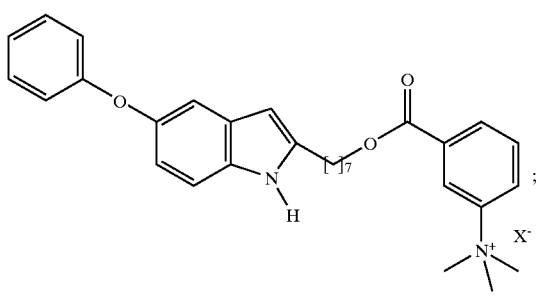
884
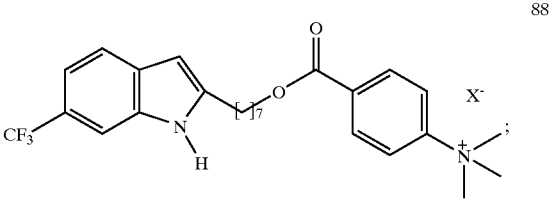
875
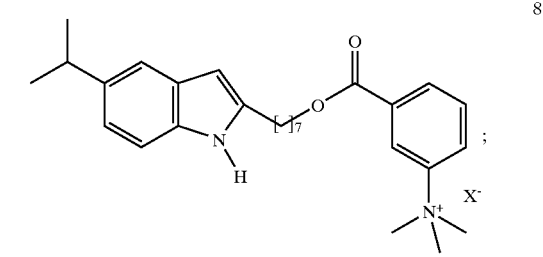
886
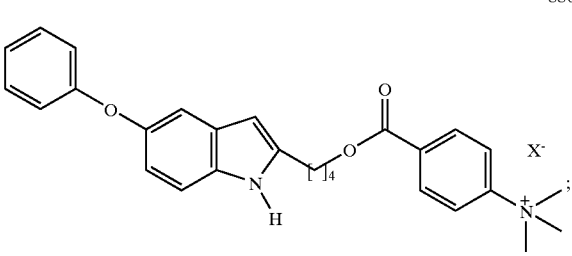

-continued

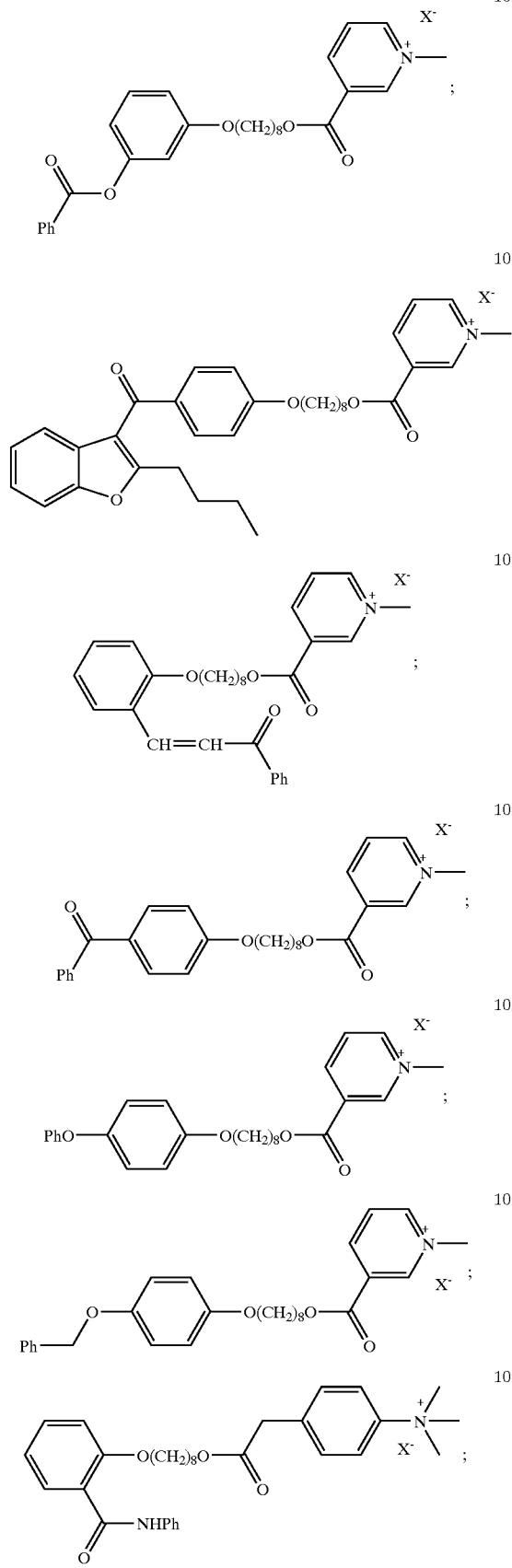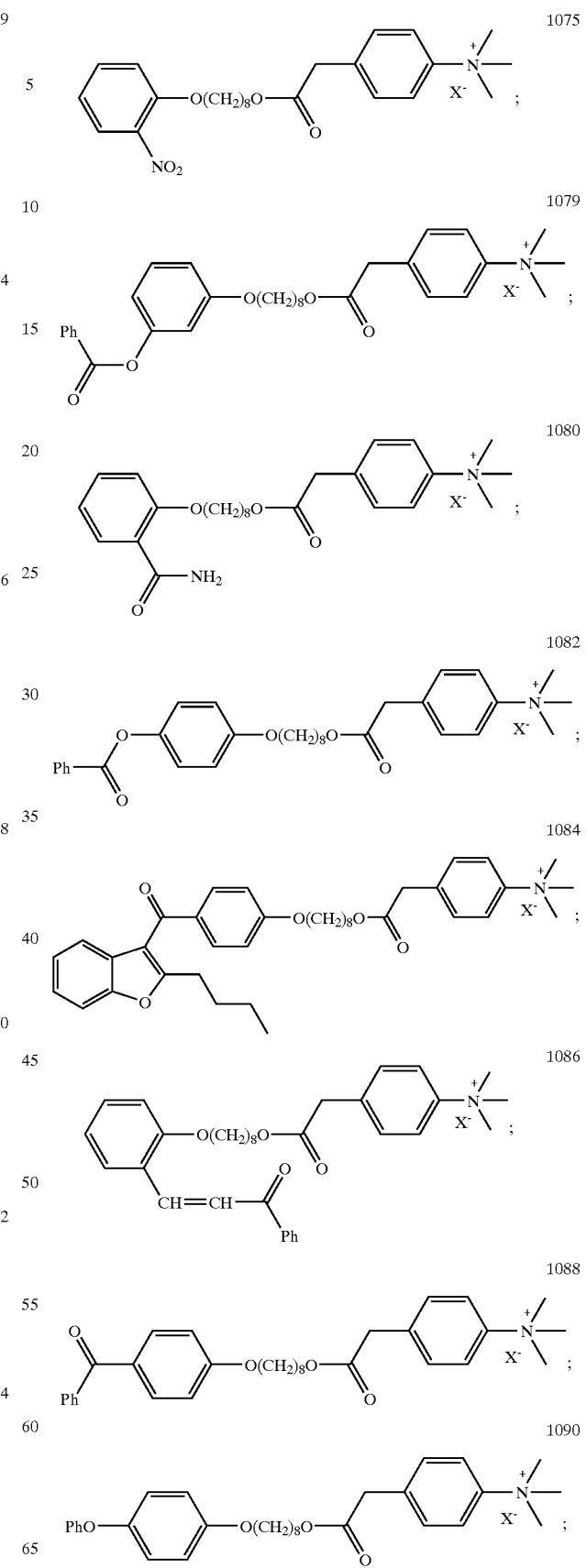

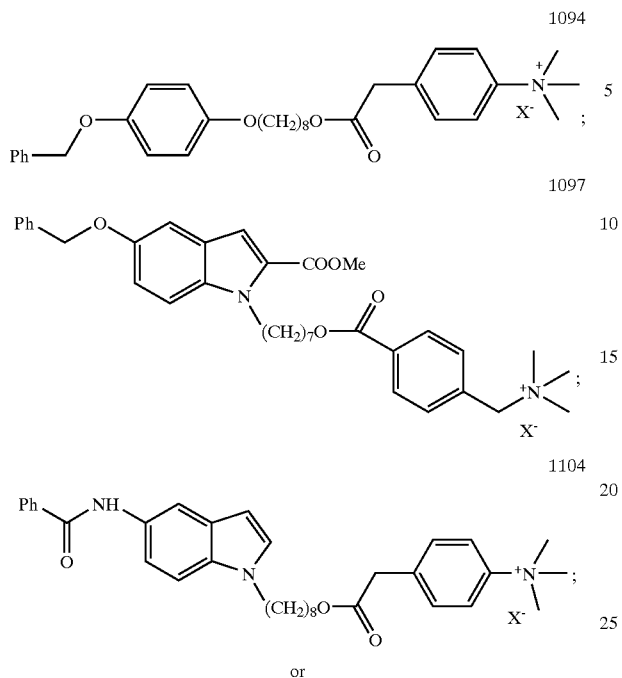
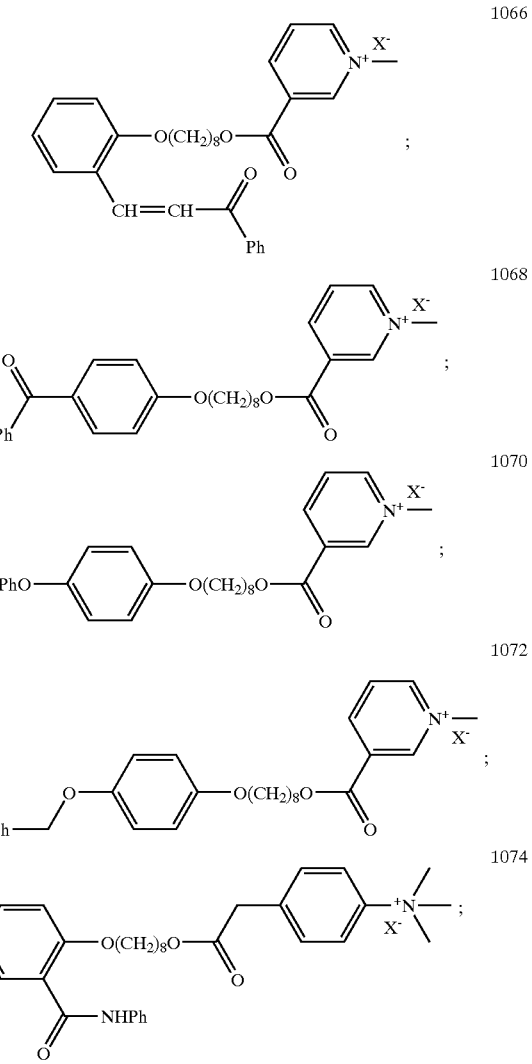
In yet a further embodiment, the invention provides a bacterial NAD synthetase enzyme inhibitor of the formula:
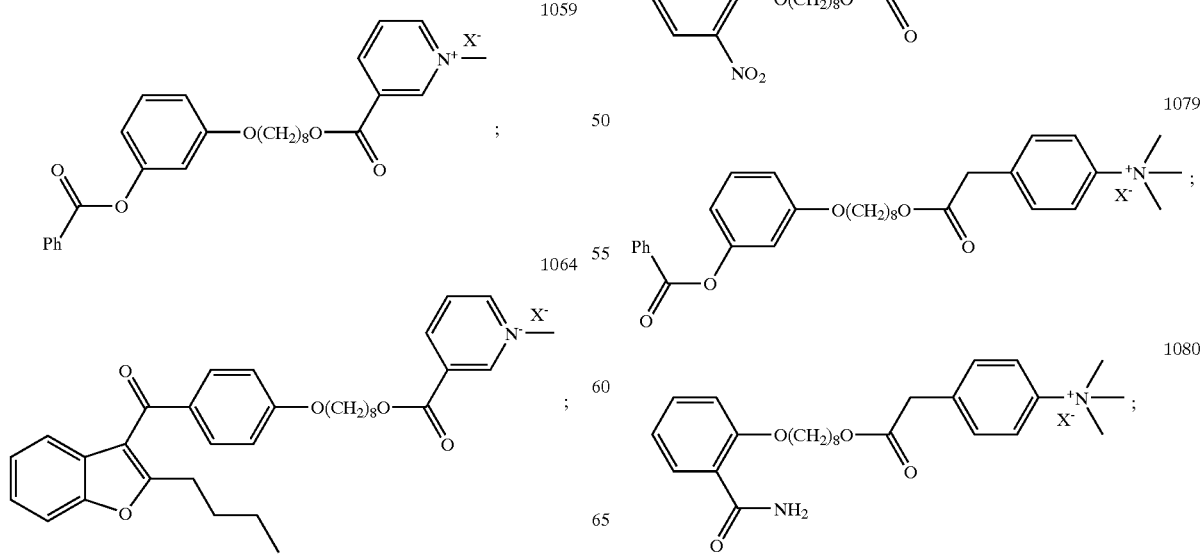

-continued

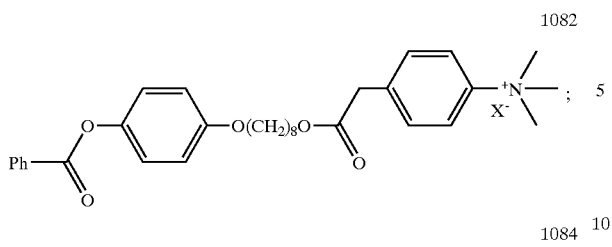
1082

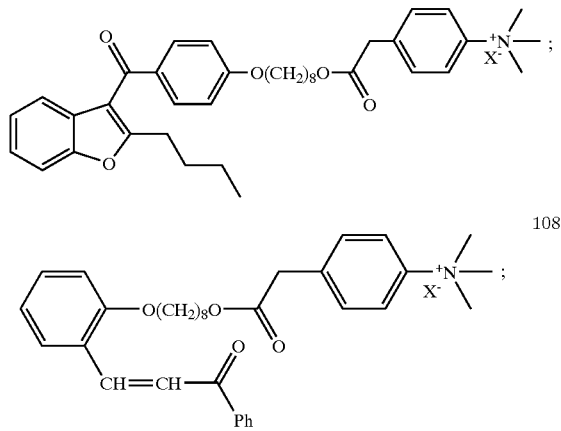
1084

1086

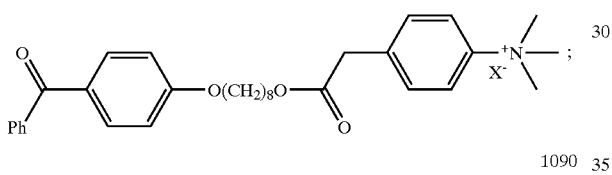
1088

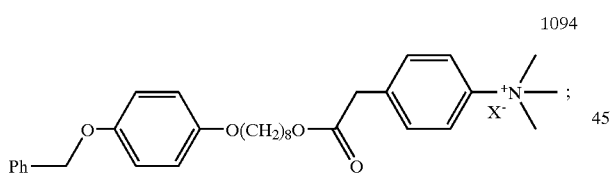
1090

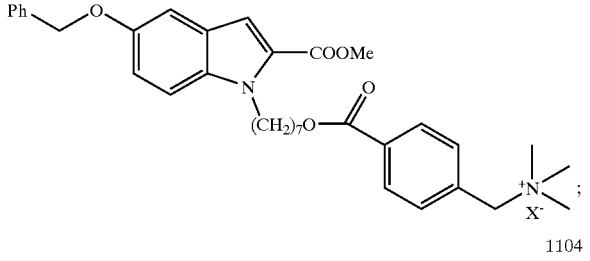
1094

1097

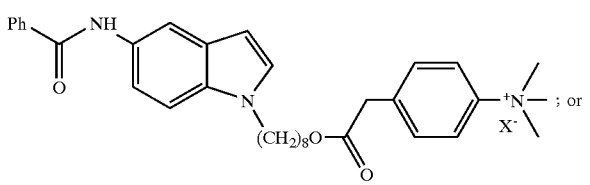
1104 ; or

-continued

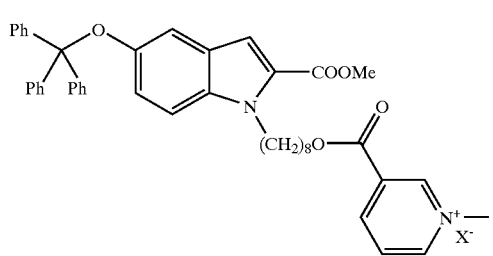
1106

In a further aspect, the invention provides a bacterial NAD synthetase enzyme inhibitor compound, having Structure 2:

Structure 2

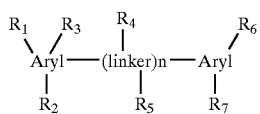

wherein n is an integer of from 1 to 12, $R_1$–$R_7$ each, independently, is an H, an unsubstituted or a substituted cyclic or aliphatic group, a branched or an unbranched group, wherein the linker is a cyclic or aliphatic, branched or an unbranched alkyl, alkenyl, or an alkynyl group and wherein the linker may also contain heteroatoms.

In yet another aspect, the invention provides a bacterial NAD synthetase enzyme inhibitor compound, having Structure 4:

Structure 4

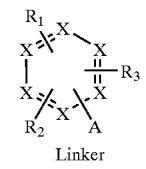

Linker

A—(CH)n—B

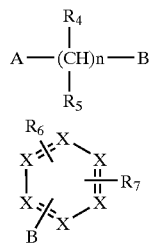

wherein X is a C, N, O or S within a monocyclic or bicyclic moiety, A and B represent the respective sites of attachment for the linker, n is an integer of from 1 to 12, R1–R7 each, independently, is an H, an unsubstituted or a substituted cyclic group, or an aliphatic group, or a branched or an unbranched group, wherein the linker is a saturated or unsaturated cyclic group or an aliphatic branched or unbranched alkyl, alkenyl or alkynyl group, and wherein the linker may also contain heteroatoms.

Further, the invention provides a method of treating or preventing a microbial infection in a mammal comprising administering to the mammal a treatment effective or treatment preventive amount of a bacterial NAD synthetase enzyme inhibitor compound. Still further, a method is provided of killing a prokaryote with an amount of prokaryotic NAD synthetase enzyme inhibitor to reduce of eliminate the production of NAD whereby the prokaryote is killed. Moreover, a method is provided of decreasing prokaryotic growth, comprising contacting the prokaryote with an amount of a prokaryotic NAD synthetase enzyme inhibitor effective to reduce or eliminate the production of NAD whereby prokaryotic growth is decreased. Further provided is a disinfectant compound wherein the compound comprises a bacterial NAD synthetase enzyme inhibitor. Still further, the invention provides a method of disinfecting a material contaminated by a microbe, comprising contacting a contaminated material with a bacterial NAD synthetase enzyme inhibitor compound in an amount sufficient to kill or deactivate the microbe.

In yet another aspect, the invention provides a method of making a bacterial NAD synthetase inhibitor compound comprising the steps of: a. alkylating 5-nitroindole with 6-bromohexyl acetate to form a 6-[N-(5-nitroindolyl)]hexyl acetate; b. hydrolyzing the 6-[N-(5-nitroindolyl)]hexyl acetate to form N-(5-nitroindolyl)hexan-1-ol; c. esterifying the 6-[N-(5-nitroindolyl)]hexan-1-ol with nicotinic acid to form 6-[N-(5-nitroindolyl)]hexyl nicotinate; and d. N-methylating the 6-[N-(5-nitroindolyl)]hexyl nicotinate.

Further, the invention provides a method of making a bacterial NAD synthetase inhibitor compound comprising the steps of: a alkylating 5-nitroindole with bromoalkyl acetate wherein the indole alkyl acetate is converted to indole alkyl alcohol; b. reacting the indole alkyl alcohol with the appropriate reagent to form an indole alkyl ester, and c. N-methylating the indole alkyl ester.

Moreover, the invention provides a method of making a bacterial NAD synthetase inhibitor compound comprising the steps of: a. reacting indole carboxylic acid with the appropriate reagent to provide an indole carboxylate methyl ester or an indole benzyl carboxylate ester; b. N-alkylating the indole carboxylate methyl ester or the indole carboxylate benzyl ester with bromoalkyl acetate; c. reacting the material from step b above with the appropriate reagent to form an indolealkyl alcohol; d. coupling the indolealkyl alcohol with an aromatic amine; and e. reacting the indolealkyl alcohol with the appropriate reagent to convert the methyl or benzyl indolecarboxylate to the respective indole carboxylic acids.

In another aspect, the invention provides a method of making a bacterial NAD synthetase inhibitor compound comprising the steps of: a. brominating an aniline with N-bromosuccinimide to form a 2-bromo-$R^1$-substituted-aniline or a 2-bromo-$R^2$-substituted-aniline; b. reacting the 2-bromo-$R^{21}$-substituted-aniline or the 2-bromo-$R^2$-substituted-aniline using a Heck coupling reaction to form an alkyne-substituted aniline; c. reacting the alkyne-substituted aniline using a cyclization reaction to form an indole alcohol; d. quaternizing the indole alcohol with an amine; e. reacting the indole alcohol with methansulfonyl chloride to provide an indole mesylate; and f. reacting the indole mesylate with a carboxylic acid to form an indole ester.

Still further, the invention provides a method of making a bacterial NAD synthetase inhibitor compound comprising the steps of: a. brominating an aniline with N-bromosuccinimide to form a 2-bromo-$R^1$-substituted-aniline or a 2-bromo-$R^2$-substituted-aniline; b. reacting the 2-bromo-$R^1$-substituted-aniline or a 2-bromo-$R^2$-substituted-aniline using a Heck coupling reaction to form an alkyne-substituted aniline; c. reacting the alkyne-substituted aniline using a cyclization reaction to form an indole alcohol; d. quaternizing the indole alcohol with an amine; e. reacting the indole alcohol with triflouromethyl-sulfonic anhydride to provide a triflate; and f. reacting the indole triflate with an amine to form an indole alkylammonium product.

In a further aspect, the invention provides a method of making a bacterial NAD synthetase inhibitor compound comprising the steps of: a. alkylating a phenol with 7-bromo-1-heptanol to provide 7-(phenyloxy)-1-heptanol; b. mesylating 7-(phenyloxy)-1-heptanol to provide 7-(phenyloxy)-1-heptyl methanesulfonate; c. esterifying 7-(phenyloxy)-1-heptyl-methanesulfonate to provide 7-(phenyloxy)-1-heptyl nicotinate; and d. n-methylating 7-(phenyloxy)-1-heptyl nicotinate to provide [7-(phenyloxy)-1-heptyl-(N-methyl)nictotinate]iodide.

In yet another aspect, the invention provides a method of generating a library comprising at least one bacterial NAD synthetase enzyme inhibitor compound comprising the steps of: a. obtaining the crystal structure of a bacterial NAD synthetase enzyme; b. identifying one or more sites of catalytic activity on the NAD synthetase enzyme; c. identifying the chemical structure of the catalytic sites on the NAD synthetase enzyme; d. selecting one or more active molecules that will demonstrate affinity for at least one of the catalytic sites on the NAD synthetase enzyme; f. synthesizing one or more dimeric compounds comprised of at least one active molecule wherein the active molecule compound are joined by means of n linker compounds and wherein n is an integer of from 1 to 12, and g. screening the one or more compounds for NAD synthetase inhibitor activity.

In a further aspect of the invention herein, a method is provided for the in vitro screening a compound for bacterial NAD synthetase enzyme inhibitory activity comprising the steps of: a. preparing a bacterial NAD synthetase enzyme solution from pure bacterial NAD synthetase enzyme mixed with a suitable buffer; b. contacting the bacterial NAD synthetase enzyme solution with a test compound; and c. measuring the rate of the enzyme-catalyzed reaction between the NAD synthetase enzyme and the test compound, wherein the rate of the enzyme catalyzed reaction comprises a measure of bacterial NAD synthetase enzyme inhibitory activity.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included herein.

Before the present methods, compounds, compositions and apparatuses are disclosed and described it is to be understood that this invention is not limited to the specific synthetic methods described herein. It is to be further understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

Throughout this application, where a chemical diagram has a straight line emanating from a chemical structure, such a line represents a $CH_3$ group. For example, in the following diagram:

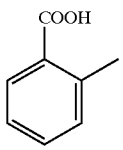

o-methylbenzoic acid is represented.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. The term "cycloalkyl" intends a cyclic alkyl group of from three to eight, preferably five or six carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms.

The term "alkylene" as used herein refers to a difunctional saturated branched or unbranched hydrocarbon chain containing from 1 to 24 carbon atoms, and includes, for example, methylene (—CH2—), ethylene (—CH2—CH2—), propylene (—CH2—CH2—CH2—), 2-methylpropylene [—CH2—CH(CH3)—CH2—], hexylene [—(CH2)6—] and the like. The term "cycloalkylene" as used herein refers to a cyclic alkylene group, typically a 5- or 6-membered ring.

The term "alkene" as used herein intends a mono-unsaturated or di-unsaturated hydrocarbon group of 2 to 24 carbon atoms. Asymmetric structures such as (AB)C=C(CD) are intended to include both the E and Z isomers. This may be presumed in structural formulae herein wherein an asymmetric alkene is present.

The term "alkynyl" as used herein refers to a branched or unbranched unsaturated hydrocarbon group of 1 to 24 carbon atoms wherein the group has at least one triple bond.

The term "cyclic" as used herein intends a structure that is characterized by one or more closed rings. As further used herein, the cyclic compounds discussed herein may be saturated or unsaturated and may be heterocyclic. By heterocyclic, it is meant a closed-ring structure, preferably of 5 or 6 members, in which one or more atoms in the ring is an element other than carbon, for example, sulfur, nitrogen, etc.

The term "bicyclic" as used herein intends a structure with two closed rings. As further used herein, the two rings in a bicyclic structure can be the sane or different. Either of the rings in a bicyclic structure may be heterocyclic.

By the term "effective amount" of a compound as provided herein is meant a sufficient amount of the compound to provide the desired treatment or preventive effect. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount may be determined by one of ordinary skill in the art using only routine experimentation. It is preferred that the effective amount be essentially non-toxic to the subject, but it is contemplated that some toxicity will be acceptable in some circumstances where higher dosages are required.

By "pharmaceutically acceptable carrier" is meant a material that is not biologically or otherwise undesirable, i.e., the material may be administered to an individual along with the compounds of the invention without causing any undesirable biological effects or interacting in a deleterious manner with any of the other components of the pharmaceutical composition in which it is contained.

As used herein, "NAD synthetase enzyme" is defined as the enzyme that catalyzes the final reaction in the biosynthesis of NAD, namely, the transformation of NaAD into NAD. As used herein, the term "catalytic sites" are defined as those portions of the NAD synthetase enzyme that bind to substrates, and cofactors, including nictonic acid dinucleotide (NaAD), NAD, adenosine triphosphate (ATP), adenosine monophosphate (AMP), pyrophosphate, magnesium and ammonia in bacteria or microbes. The term "receptor site" or "receptor subsite" relates to those portions of the bacterial NAD synthetase enzyme in which the bacterial NAD synthetase enzyme inhibitors disclosed herein are believed to bind. For the purposes of this disclosure, the terms "catalytic site," "receptor site" and "receptor subsite" may be used interchangeably.

As used herein, the terms "library" and "library of compounds" denote an intentionally created collection of differing compounds which can be prepared by the synthetic means provided herein or generated otherwise using synthetic methods utilized in the art. The library can be screened for biological activity in any variety of methods, such as those disclosed below herein, as well as other methods useful for assessing the biological activity of chemical compounds. One of skill in the art will recognize that the means utilized to generate the libraries herein comprise generally combinatorial chemical methods such as those described in Gallop, et al, "Applications of Combinatorial Techniques to Drug Discovery," "Part 1 Background and Peptide Combinatorial Libraries," and "Part 2: Combinatorial Organic Synthesis, Library Screening Strategies, and Future Directions," *J. Med. Chem.*, Vol. 37(1994) pp. 1233 and 1385. As used herein, the terms "combinatorial chemistry" or "combinatorial methods" are defined as the systematic and repetitive, covalent connection of a set of different "building blocks" of varying structure, such as the active molecules disclosed herein, to provide a large array of diverse molecular entities. As contemplated herein, the large array of diverse molecular entities together form the libraries of compounds of the invention.

As used herein, the term "antibacterial compound" denotes a material that kills or deactivates bacteria or microbes so as to reduce or eliminate the harmful effects of the bacteria on a subject or in a system. Such materials are also known in the art as "bacteriostatic agents" or "bacteriocidal agents." The bacteria so affected can be gram positive, gram negative or a combination thereof The terms "antimicrobial compound" and "broad spectrum antibiotic" denote a material that kills or deactivates a wide variety of microbes, including, but not limited to, one of more of, gram positive or gram negative bacteria, *Staphylococcus aureus, Streptococcus pyogenes, Streptococcus viridans*, Enterococcus, anaerobic Streptococcus, Pneumococcus, Gonococcus, Meningococcus, Mima, *Bacillus anthracis, C. diphtheriae, List. monocytogenes, Streptobacillus monohiliformis, Erysipelothrix insidiosa, E. coli, A. aerogenes, A. faecalis, Proteus mirabilis, Pseudomonas aeruginosa, K. pneumoniae*, Salmonella, Shigella, *H. influenzae, H. ducreyi*, Brucella, *Past. pestis, Past.* tularensis, Past. muiltocida, V. comma, Actinobacillus mallei, Pseud. pseudomallei, Cl. tetani, Bacteroides, *Fusobacterium fusiforme, M. tuberculosis*, atypical niycobacteria, *Actinomyces israelii*, Nocardia, *T. pallidum, T. pernue, Borrelia recurrentis*, Peptospira, Rickettsia, and *Mycoplasma pneumoniae*.

In accordance with the desirability for developing improved antibacterial and antimicrobial agents, with the invention herein novel compounds have been identified that inhibit bacterial NAD synthetase enzymatic activity. Such activity translates into effectiveness as bacteriocidal agents, as well as effectiveness as a broad spectrum antibiotic materials. Novel compounds have been developed that inhibit a previously unrecognized target in prokaryotic organisms, such as bacteria, to block essential biological function and thereby cause bacterial death or deactivation of bacteria or other microbes. Specifically, the invention herein has identified an enzyme found in both gram positive and gram negative bacteria, NAD synthetase enzyme, which can be utilized as a target for drug design to provide protection from and/or treatment for bacterial and other microbial infections.

The NAD synthetase enzyme catalyzes the final step in the biosynthesis of nicotinamide adenine dinucleotide (NAD). Bacterial NAD synthetase is an ammonia-dependent amnidotransferase belonging to a family of "N-type" ATP pyrophosphatases; this family also includes asparagine synthetase and argininosuccinate synthetase. NAD synthetase enzyme catalyzes the last step in both the de novo and salvage pathways for NAD$^+$ biosynthesis, which involves the transfer of ammonia to the carboxylate of nicotinic acid adenine dinucleotide (NAAD) in the presence of ATP and Mg$^{+2}$. The overall, reaction is illustrated in Scheme 1.

SCHEME 1:

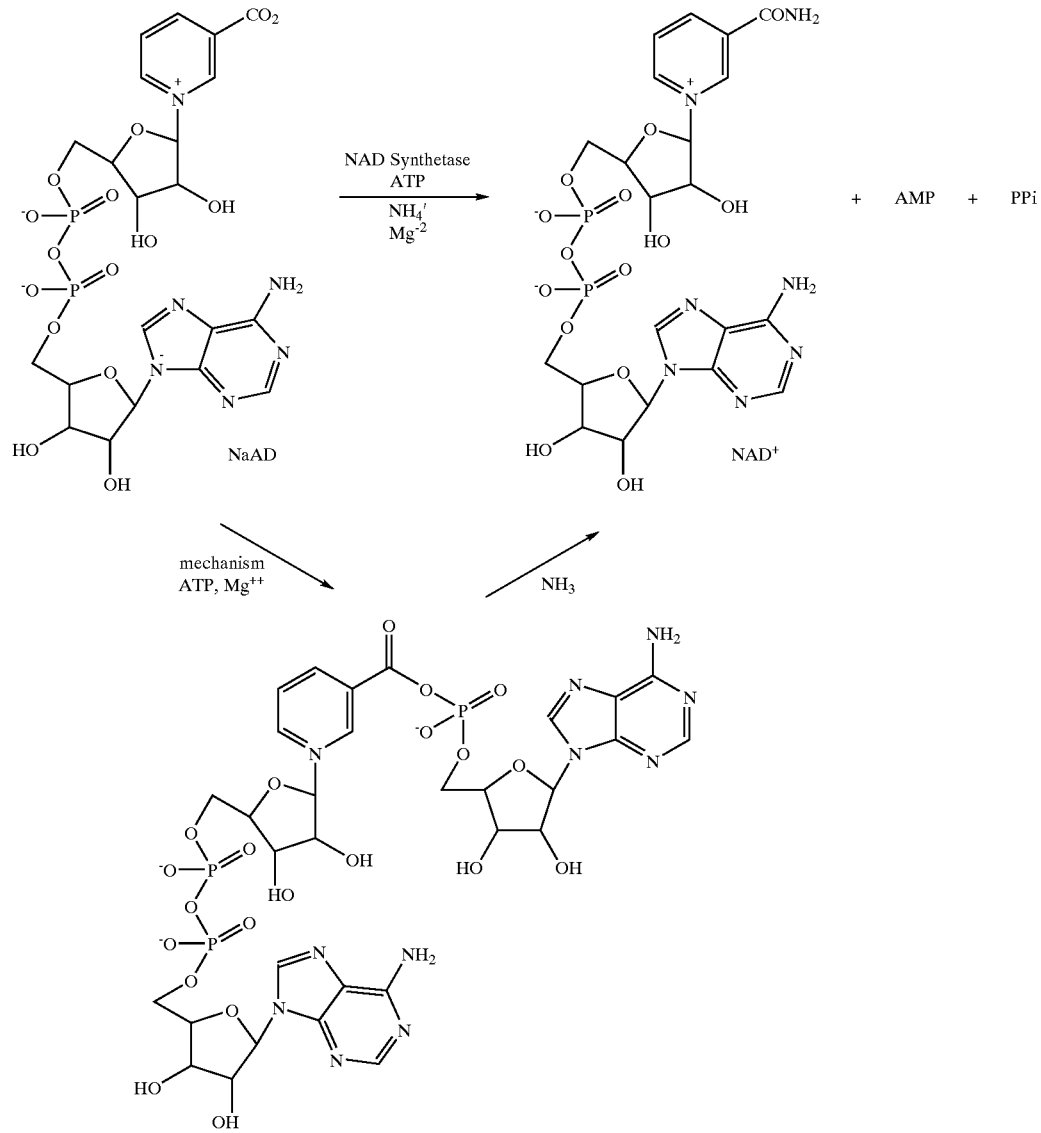

Unlike eukaryotic NAD synthetase e.g., that found in mammals, which can utilize glutamine as a source of nitrogen, prokaryotic NAD synthetase in bacteria utilizes ammonia as the sole nitrogen source. Through x-ray crystallography and other methods, the invention has identified marked differences in the structures of eukaryotic and prokaryotic forms of the NAD synthetase enzyme. For example, B. subtilis NAD synthetase enzyme, which in the invention has been crystallized and used in the drug design methodologies herein, is a dimeric material with molecular weight around 60,500. In marked contrast, the eukaryotic form of NAD synthetase found in mammals is multimeric and has a molecular weight of at least 10 times larger.

By utilizing the significant differences between the eukaryotic and prokaryotic forms of NAD synthetase enzyme, the invention herein provides novel compounds that can be utilized as antibacterial and antimicrobial agents that specifically target the prokaryotic NAD synthetase enzyme without also effecting a mammalian host. With the invention herein, it has been found that by specifically inhibiting bacterial NAD synthetase enzymatic activity, bacteria can be deprived of the energy necessary to thrive and replicate. Accordingly, through the invention disclosed and claimed herein, antibacterial and antimicrobial drugs have been developed that preferentially attack the bacteria to kill or deactivate it so as to reduce or eliminate its harmful properties, without appreciably affecting mammalian NAD synthetase enzymatic activity at the same dosage.

Furthermore, novel methods are provided that allow the rapid screening of compounds for bacterial NAD synthetase enzyme inhibitory activity. Moreover, the invention provides methods of treating microbial infections in a subject. Because of the differences in structure between bacterial and mammalian NAD synthetase enzyme, it would not be expected that the compounds of the invention would inhibit or otherwise affect mammalian NAD synthetase enzyme in the same manner as the compounds act on bacteria.

Without being bound by theory, through chemical analysis and x-ray crystallography methods, at least two separate catalytic subsites on the bacterial NAD synthetase enzyme in which it is possible to bind at least one or more small molecules ("active molecules") have been characterized. These sites are illustrated below by the cartoon in FIG. 2.

FIG. 2: CATALYTIC SITES IN BACTERIAL NAD SYNTHETASE ENZYME

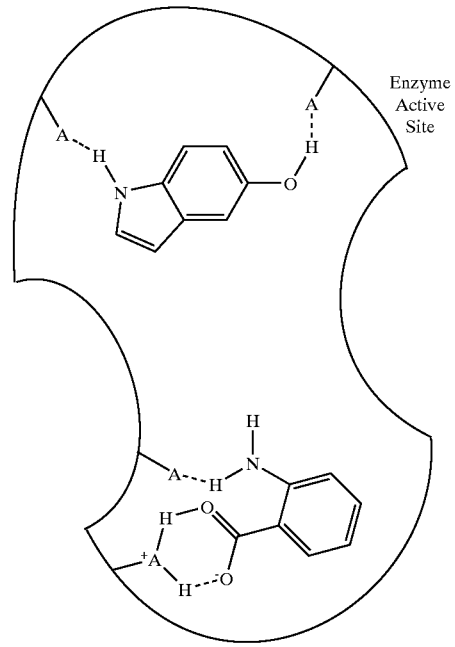

Because of the specific structure of these catalytic sites, it has been determined that it is possible to identify small molecules that will demonstrate affinity for at least one of the sites. Small molecules of the proper configuration, the configuration being determined by the structure of the catalytic site(s), will bind with a receptor site or sites on the bacterial NAD synthetase enzyme, thereby blocking the catalytic activity of the enzyme. FIG. 4 illustrates via cartoon a bacterial NAD synthetase enzyme in which the catalytic sites are blocked by an example of a compound of the present invention.

FIG. 4: BACTERIAL NAD SYNTHETASE ENZYME WITH BLOCKED CATALYTIC/RECEPTOR SITES

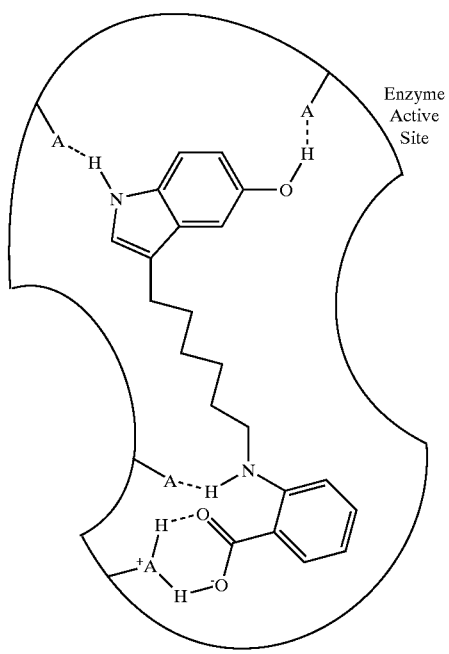

Under such circumstances, it is hypothesized that spore-forming bacteria will be unable to undergo germination and outgrowth, and the essential cellular respiratory functions of the vegetative bacteria will be halted, thereby causing cellular death or deactivation, e.g., gram positive and gram negative bacteria and other microbes will be killed or prevented from undergoing growth. Accordingly, the invention has found that compounds that exhibit inhibitory activity against the bacterial NAD synthetase enzyme will also exhibit therapeutic activity as antibacterial and antimicrobial compounds, as well as broad spectrum antibiotic materials.

With the invention herein it has been surprisingly found that it is possible to synthesize novel tethered dimeric compounds that will exhibit activity as bacterial NAD synthetase enzyme inhibitors. By linking one or more active molecules through a linker molecule, one or more ends of the tethered dimer can bind in the respective receptor sites or subsites to thereby render the bacterial NAD synthetase enzyme inactive. When more than one active molecule is used, each active molecule can be the same or different. The term "active molecules" as used herein refers to small molecules that may be used alone or tethered together through a linker (tether) fragment to form a tethered dimeric compound.

In the present invention, the active molecules are comprised of substituent groups as hereinafter disclosed that will bind with at least one of the receptor sites in bacterial NAD synthetase enzyme. In the invention herein one or more active molecules are tethered together to form a dimeric molecule that is capable of inhibiting the bacterial NAD synthetase enzyme.

Further, in this invention it has been found that, under some circumstances, different active molecules will be more likely to bind to different locations in the receptor site of a bacterial NAD synthetase enzyme because of the differing chemical make-up of each of these sites. Therefore, in one embodiment, it is beneficial to tether at least two different active molecules to each other wherein each active molecule demonstrates selective affinity for a different subsite in the receptor. Using the tethered dimers herein it is possible to drastically enhance the potency of NAD synthetase enzyme inhibition, as compared to blocking a single site on the bacterial NAD synthetase enzyme. As used herein, the term "selective affinity" means that the active molecule shows enhanced tendency to bind with one subsite with the receptor in the bacterial NAD synthetase enzyme because of a chemical complementarity between the receptor subsite and the active molecule. A tethered dimer compound is illustrated in Scheme 2 below.

SCHEME 2:

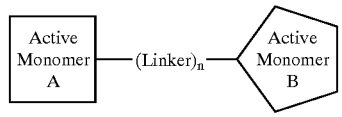

In one embodiment, a dimeric inhibitor compound will bind with, for example, the sites of catalytic activity on the bacterial NAD synthetase enzyme, thereby preventing the production of NAD/NADH by the bacteria. As an additional surprising finding in this invention, it has been determined that by varying the length of the linker molecule, and, accordingly, the distance between the two active molecules, the affinity of the tethered inhibitor compound for the NAD synthetase enzyme will also vary.

In practice of the invention relating to the design of novel NAD synthetase enzyme inhibitor compounds, a software program can be utilized which facilitates the prediction of the binding affinities of molecules to proteins so as to allow identification of commercially available small molecules with the ability to bind to at least one receptor subsite in the bacterial NAD synthetase enzyme. An example of one such computer program is DOCK, available from the Department of Pharmaceutical Chemistry at the University of California, San Francisco. DOCK evaluates the chemical and geometric complementarity between a small molecule and a macromolecular binding site. However, such a program would be useless in the design of a bacterial NAD synthetase enzyme inhibitor in the absence of complete information regarding the enzyme's structure and the chemical makeup of the receptor sites, identified and disclosed fully for the first time herein.

With this invention, the crystal structure of one type of bacterial NAD synthetase enzyme e.g., B. subtilis has been for the first time identified fully. The x-ray crystal structure of NAD synthetase enzyme from B. subtilis had been reported in the literature. (M. Rizzi et al., The EMBO Journal, 15, 5125, (1996); M. Rizzi et al., Structure, 1129 (1998)). This was accomplished in free form and in complex with ATP and $Mg^{+2}$ at 2.6 and 2.0 Å, respectively. This structure contained the hydrolyzed form of ATP, namely AMP and Ppi, in the ATP binding site and ATP was present in the NaAD binding site. However, the prior art was not able to obtain the structure of the enzyme complex containing NaAD due to technical problems that precluded full identification. Without the structure of the enzyme complex containing NaAD, the structure-based drug design targeted to NAD synthetase enzyme of the present invention could not be developed.

In order to carry out structure-based drug design targeted to bacterial NAD synthetase enzyme, the structure of the enzyme in complex with all substrates, including NaAD has been solved herein. The additional structural information obtained in this invention for the first time clearly defined the interactions between NaAD and the enzyme, which provided information important for guiding combinatorial library design and inhibitor identification. Schematic drawings of crystal structures of the open and blocked receptor/catalytic sites of B. subtilis are set out previously in FIGS. 2 and 4.

The invention utilizes two approaches reported in the literature (for other biological targets) to help identify lead compounds. (1) Once the structure of a bacterial NAD synthetase catalytic site was identified, the software DOCK (I. D. Kunz et al., J. Mol. Biol., 161, 269–288 (1982)) was utilized to search the Available Chemicals Directory database and computationally score the relative binding affinities for each structure. Based on these results and structural information regarding substrate binding, commercially available compounds were selected for purchase and subsequent enzyme kinetics evaluation. Such database searching strategies in drug discovery are now commonly used by those of skill in the art of drug design. (D. T. Manallack, Drug Discovery Today, 1, 231–238 (1996)). (2) Using the results of biological screening for selected commercially available compounds to identify biologically active molecules, the inventors then designed a combinatorial library consisting of "tethered dimers" to rapidly identify more effective inhibitors of NAD synthetase enzyme as antibacterial agents. The use of "tethered dimers" to enhance the binding affinity of two moderately effective small molecule ligands that interact in the same binding site has been previously described in the literature. (S. B. Stuker, P. J. Hejduk, R. P. Meadows, and S. W. Fesik, Science, 274, 1531–1534 (1996)). However, this invention involves the first and, therefore, a novel application of database searching coupled with a combinatorial tethered dimer approach that was guided by the structure of and targeted to the bacterial NAD synthetase enzyme.

Examples from the top scoring small molecules as determined by, for example, DOCK, are preferably pre-screened using in vitro enzyme assays as further described herein. As a significant aspect of the invention herein, the preferred screening method utilized should allow the rapid screening of large numbers of compounds for inhibitory activity. In a preferred method of the present invention, the small molecule inhibitor candidate for each site that is most promising as an active molecule, as identified by DOCK (or other programs known to one of skill in the art) and the prescreening method herein, or that were designed based upon the substrate protein complex structure, were synthesized according to the methods disclosed herein below.

In one embodiment, the active molecules are chemically tethered to one another by means of a linker compound. In a further embodiment, the linker comprises one or more $CH_2$ or other groups, using a variety of tether lengths, preferably 1 to 12 nonhydrogen atoms, more preferably 3 to 10 nonhydrogen atoms, further more preferably 5 to 9 nonhydrogen atoms and, still more preferably, 6 to 9 nonhydrogen atoms.

In another embodiment of the present invention, the novel compounds with preferred structures determined from the methods described above are synthesized by means of rapid, solution phase-parallel synthesis of the tethered dimers compounds in a combinatorial fashion. One of skill in the art will recognize such techniques. For each class of dimeric compounds designed in accordance with the invention herein, a novel synthetic strategy was developed to allow variation in the length of the linking group through which the active molecules are joined. These synthetic strategies are set forth herein as Schemes 3 through 7 and in Examples 1 through 5 below. Use of the preferred method of variable linkage greatly increases the number of different tethered dimeric compounds that can be produced from a single pair of the same or different active molecules. The active molecules specifically disclosed herein may be used, as well as any pharmaceutically acceptable salts thereof.

As noted, pharmaceutically acceptable salts of the compounds set out herein below are also contemplated for use in this invention. Such salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of structural formula (I) to base used are chosen to provide the ratio desired for any particular salts. For preparing, for example, the ammonium salts of the free acid starting material-a particular preferred embodiment-the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used.

Similarly, salts of aliphatic and/or aromatic amines are also contemplated for use in this invention. A variety of pharmaceutically acceptable salts may be prepared by any of several methods well known to those skilled in the art. Such methods include treatment of a free aliphatic or aromatic amine with an appropriate carboxylic acid, mineral acid, or alkyl halide, or by conversion of the ammonium salt to another form using ion exchange resins.

Compounds prepared in accordance with the design and synthesis methods of this invention are especially attractive because they may preferably be further optimized by incorporation of substituents on either the active molecule and/or the linking group. These latter modifications can also preferably be accomplished using the combinatorial methods disclosed herein.

In a further embodiment of the present invention, selected novel compounds whose structures are designed by the above methods are synthesized individually using a novel strategy that allows variation in the length of the linking group. An example of a route preferably utilized to synthesize one class of dimers according to the present invention, using a single pair of active molecules, is summarized below in Scheme 3.

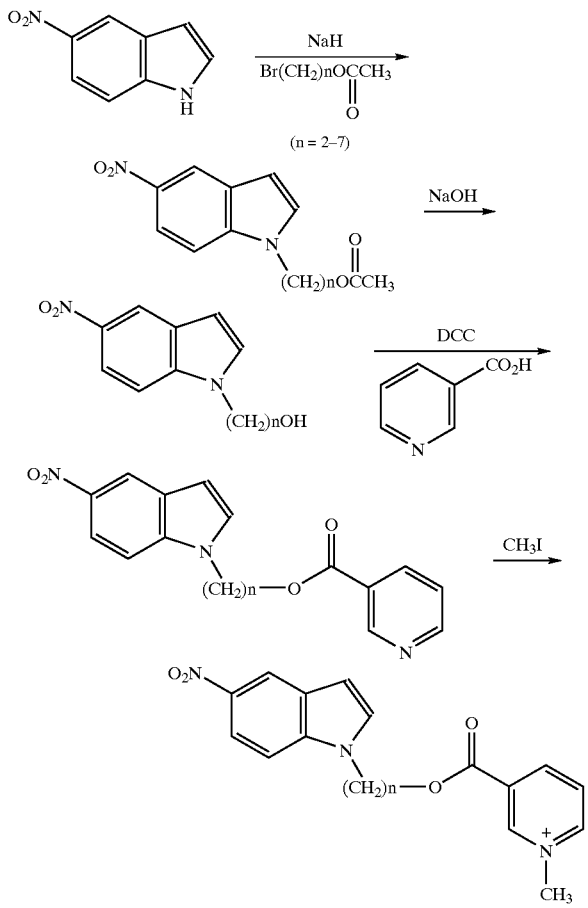

In a preferred embodiment, the invention provides a method of making a bacterial NAD synthetase inhibitor compound comprising the steps of:

a. alkylating 5-nitroindole with 6-bromohexyl acetate to form a 6-[N-(5-nitroindolyl)]hexyl acetate;

b. hydrolyzing the 6-[N-(5-nitroindolyl)]hexyl acetate to form 6-[N(5 nitroindolyl)]hexan-1-ol;

c. esterifying the 6-[N-(5-nitroindolyl)]hexan-1-ol with nicotinic acid to form 6[N-(5-nitroindolyl)]hexyl nicotinate; and d. N-methylating the 6-[N-(5-nitroindolyl)]hexyl nicotinate.

The following compounds were prepared according to Scheme 3 above, wherein n represents the number of linker groups tethering the two active molecules together.

TABLE 2

SAMPLE COMPOUND PREPARED ACCORDING TO SCHEME 3

| Compound | N |
|---|---|
| 862 | 3 |
| 863 | 4 |
| 864 | 5 |
| 865 | 6 |

Examples of additional preferred synthetic procedures utilized for preparing the library of the present invention are provided in Schemes 4–7. In Schemes 4–7, it is preferable to utilize combinational methods of synthesis using, for example, parallel solution phase synthetic techniques. One of skill in the art will readily recognize the manner in which the synthetic pathways disclosed below may be varied without departing from the novel and unobvious aspects of the invention.

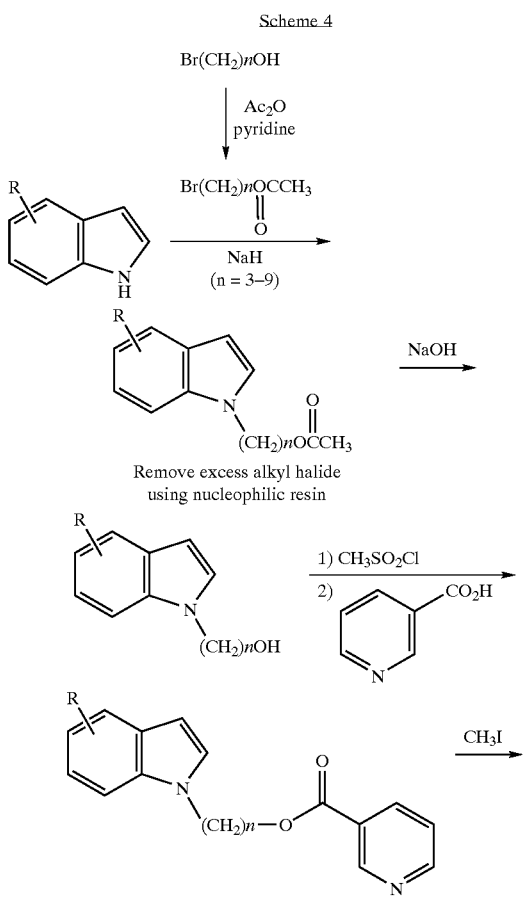

-continued

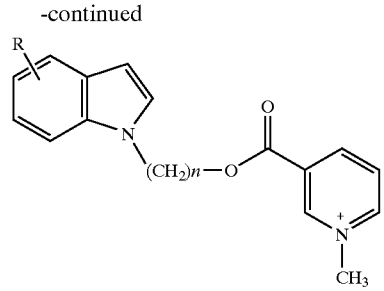

Alternatively:

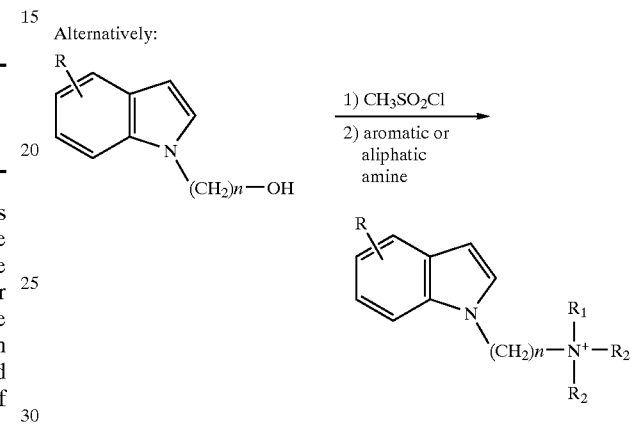

In a preferred embodiment, the invention provides a method of synthesizing a NAD synthetase inhibitor compound from the route set out in Scheme 4 above, comprising the steps of:

a. alkylating 5-nitroindole with bromoalkyl acetate wherein the indole alkyl acetate is converted to indole alkyl alcohol;

b. reacting the indole alkyl alcohol with the appropriate reagent to form an indole alkyl ester; and c. N-methylating the indole alkyl ester.

In yet another embodiment, the invention provides a method of making a NAD synthetase inhibitor compound from the route set out in Scheme 4 above comprising the steps of:

a. alkylating 5-nitroindole with bromoalkyl acetate wherein the indole alkyl acetate is converted to indole alkyl alcohol;

b. reacting the indole alkyl alcohol with the appropriate reagent to form an indole alkyl ester, and c. reacting the indole alkyl alcohol with mesyl chloride followed by reaction with an amine to generate an ammonium product.

Scheme 5

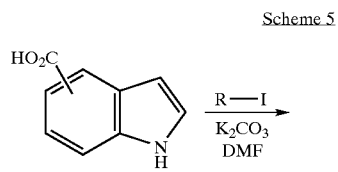

-continued

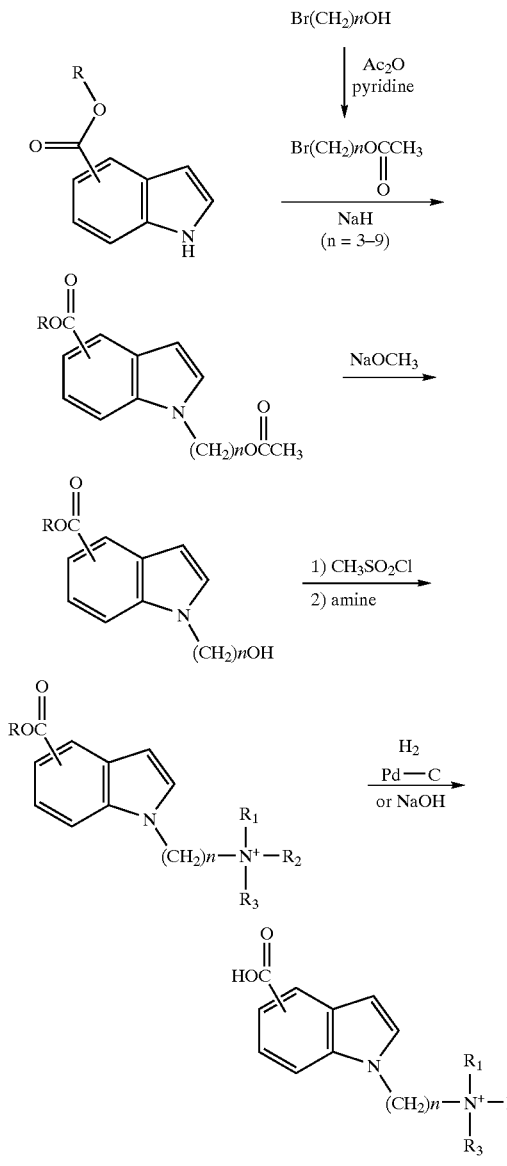

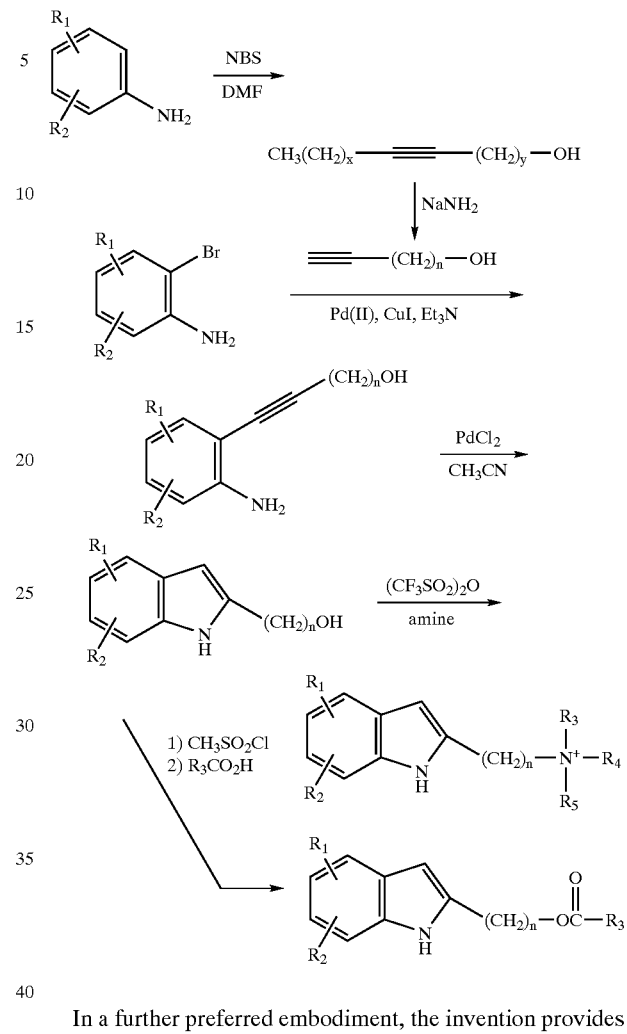

In yet a further, still preferred, embodiment, the invention provides a method of making a NAD synthetase inhibitor from the route set out in Scheme 5 above, comprising the steps of:

a. reacting indole carboxylic acid with the appropriate reagent to provide an indole carboxylate methyl ester or an indole benzyl carboxylate ester;

b. V-alkylating the indole carboxylate methyl ester or the indole carboxylate benzyl ester with bromoalkyl acetate;

c. reacting the material from step b above with the appropriate reagent to form an indolealkyl alcohol;

d. coupling the indolealkyl alcohol with an aromatic amine; and e. reacting the indolealkyl alcohol with the appropriate reagent to convert the methyl or benzyl indolecarboxylate to the respective indole carboxylic acids.

In a further preferred embodiment, the invention provides a method of making a NAD synthetase inhibitor from the route set out in Scheme 6 above, comprising the steps of:

a. brominating an aniline with N-bromosuccinimide to form a 2-bromo-$R^1$-substituted-aniline or a 2-bromo-$R^2$-substituted-aniline;

b. reacting the 2-bromo-$R^1$-substituted-aniline or the 2-bromo-$R^2$-substituted-aniline using a Heck coupling reaction to form an alkyne-substituted aniline;

c. reacting the alkyne-substituted aniline using a cyclization reaction to form an indole alcohol;

d. quaternizing the indole alcohol with an amine;

e. reacting the indole alcohol with methansulfonyl chloride to provide an indole mesylate; and f. reacting the indole mesylate with a carboxylic acid to form an indole ester.

In yet another preferred embodiment, the invention provides a method of making a NAD synthetase inhibitor compound from the route set out in Scheme 6 above, comprising the steps of:

a. brominating an aniline with N-bromosuccinimide to form a 2-bromo-$R^1$-substituted-aniline or a 2-bromo-$R^2$-substituted-aniline;

b. reacting the 2-bromo-$R^1$-substituted-aniline or a 2-bromo-$R^2$-substituted-aniline using a Heck coupling reaction to form an alkyne-substituted aniline;

c. reacting the alkyne-substituted aniline using a cyclization reaction to form an indole alcohol;
d. quaternizing the indole alcohol with an amine;
e. reacting the indole alcohol with triflouromethylsulfonic anhydride to provide a triflate; and
f. reacting the indole triflate with an amine to form an indole alkylammonium product.

aliphatic group, a branched or an unbranched group, and wherein the linker is a cyclic or aliphatic, branched or an unbranched alkyl, alkenyl, or an alkynyl group and wherein the linker may also contain heteroatoms. By heteroatoms, it is meant that one or more atoms is an element other than carbon.

$R^1$–$R_7$, may also be one of the following groups: an H, alkyl, alkenyl, alknyl, or an aryl. $R_1$–$R_7$, may further be a

SCHEME 7

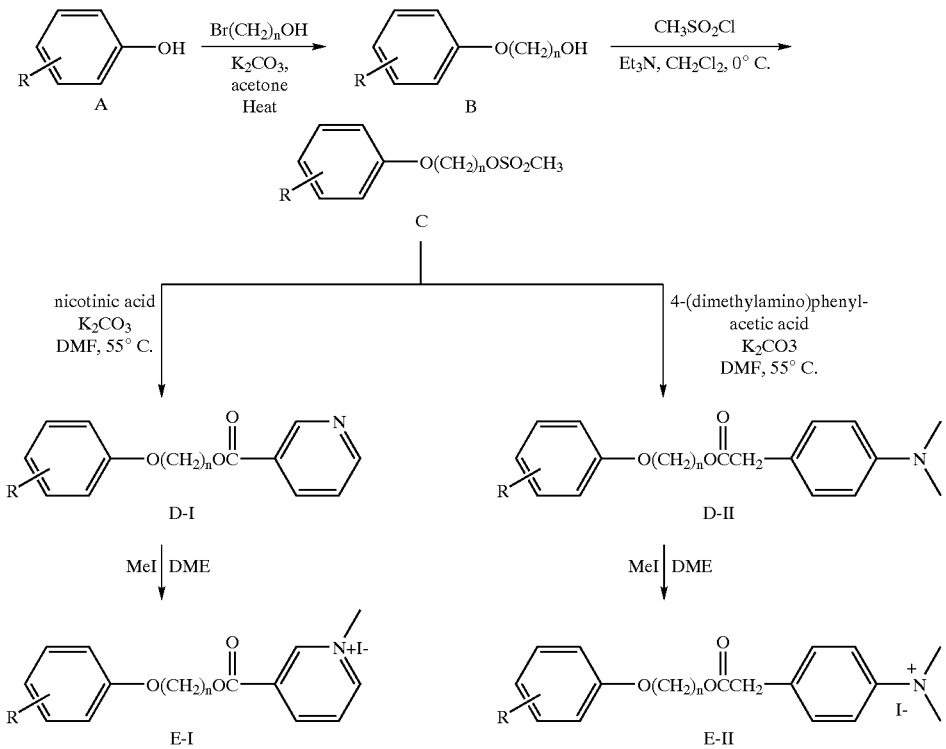

In a preferred embodiment, the invention provides a method of synthesizing a NAD synthetase inhibitor compound from the route set out in Scheme 7 above, comprising the steps of:
a. alkylating a phenol with 7-bromo-1-heptanol to provide 7-(phenyloxy)-1-heptanol;
b. mesylating 7-(phenyloxy)-1-heptanol to provide 7-(phenyloxy)-1-heptyl methanesulfonate;
c. esterifying 7-(phenyloxy)-1-heptyl-methanesulfonate to provide 7-(phenyloxy)-1-heptyl nicotinate; and
d. n-methylating 7-(phenyloxy)-1-heptyl nicotinate to provide [7-(phenyloxy)-1-heptyl-(N-methyl) nictotinate]iodide.

In a preferred embodiment, the invention provides a compound having the general structure of Structure 2:

STRUCTURE 2:

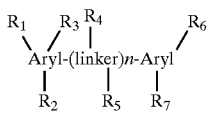

wherein:
n is an integer of from 1 to 12, $R_1$–$R_7$ each, independently, is an H, an unsubstituted or a substituted cyclic or hydroxyl, ketone, nitro, amino, amidino, guanidino, carboxylate, amide, sulfonate, or halogen or the common derivatives of these groups. Note that n may also be an integer of from 3 to 10, more preferably 5 to 9 and, still more preferably 6 to 9. The tethered active molecule, e.g., in this example denoted "aryl," moieties may be the same or different.

In a further embodiment, the invention provides a compound of Structure 4:

STRUCTURE 4:

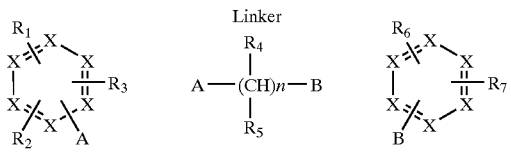

wherein:
X is a C, N, O or S within a monocyclic or bicyclic moiety, A and B represent the respective sites of attachment for the linker, n is an integer of from 1 to 12, $R_1$–$R_7$ each, independently, is an H, an unsubstituted or a substituted cyclic group, or an aliphatic group, or a branched or an unbranched group, and the linker is a saturated or unsaturated cyclic group or an aliphatic branched or unbranched alkyl, alkenyl or alkynyl group, and wherein the linker may also contain heteroatoms.

$R_1$–$R_7$ may also be one of the following groups: an H, alkyl, alkenyl, alkynyl, or an aryl group. $R_1$–$R_7$ may also be a hydroxyl, ketone, nitro, amino, amidino, guanidino, carboxylate, amide, sulfonate, or halogen or the common derivatives of these groups. One of skill in the art would know what moieties are considered to constitute derivatives of these groups. In further embodiments, n may also be an integer of from 3 to 10, more preferably 5 to 9 and, still more preferably 6 to 9.

In a further embodiment, the invention provides a compound of Structure 6:

STRUCTURE 6:

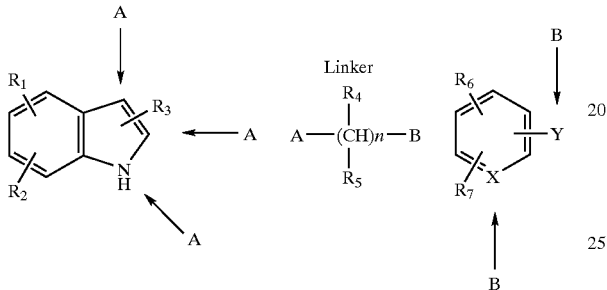

wherein:

X is C, N, O or S, Y is C, N, O, S, carboxy, ester, amide, or ketone, A and B represent the respective sites of attachment for a linker, n is an integer of from 1 to 12, and $R_1$–$R_7$ each, independently, is an H, unsubstituted or substituted cyclic group or an aliphatic group, a branched or an unbranched group, and the linker is a saturated or unsaturated cyclic or aliphatic group, branched or unbranched alkyl, alkenyl, or alkynyl group and wherein the linker may also contain heteroatoms.

$R_1$–$R_7$, may also be one of the following groups: an H, alkyl, alkenyl, alknyl, or an aryl. $R_1$–$R_7$, may further be a hydroxyl, ketone, nitro, amino, amidino, guanidino, carboxylate, amide, sulfonate, or halogen or the common derivatives of these groups. Note that n may also be an integer of from 3 to 10, more preferably 5 to 9 and, still more preferably 6 to 9. The tethered active molecule, e.g., in this example denoted "aryl," moieties may be the same or different.

In a further embodiment, the invention provides a compound of Structure 7:

STRUCTURE 7

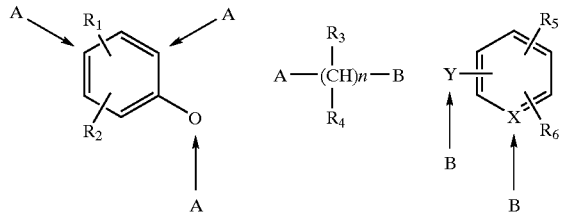

wherein:

X is C, N, O or S, Y is C, N, O, S, carboxy, ester, amide, or ketone, A and B represent the respective sites of attachment for a linker, n is an integer of from 1 to 12, and $R_1$–$R_6$ each, independently, is an H, unsubstituted or substituted cyclic group or an aliphatic group, a branched or an unbranched group, and the linker is a saturated or unsaturated cyclic or aliphatic group, branched or unbranched alkyl, alkenyl, or alkynyl group and wherein the linker may also contain heteroatoms.

$R_1$–$R_6$ may also be one of the following groups: an H, alkyl, alkenyl, alknyl, or an aryl. $R_1$–$R_6$, may further be a hydroxyl, ketone, nitro, amino, amidino, guanidino, carboxylate, amide, sulfonate, or halogen or the common derivatives of these groups. Note that n may also be an integer of from 3 to 10, more preferably 5 to 9 and, still more preferably 6 to 9. The tethered active molecule, e.g., in this example denoted "aryl," moieties may be the same or different.

In a further embodiment, the invention provides a compound of Structure 8:

STRUCTURE 8:

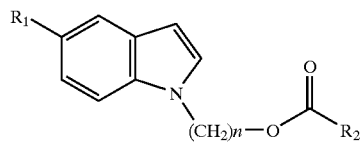

wherein:

n is an integer of from 1 to 12, $R_1$ is an H, methoxy, benzyloxy, or nitro and $R_2$ is 3-pyridyl, N-methyl-3-pyridyl, 3-quinolinyl, N-methyl-3-quinolinyl, 3-(dimethylamino)phenyl, 3-(trimethylammonio) phenyl, 4-(dimethylamino)phenyl, 4-(trimethylammonio)phenyl, 4-(dimethylamino) phenylmethyl, or 4-(trimethylammonio)phenylmethyl.

In further embodiments, n may also be an integer of from 3 to 10, more preferably 5 to 9 and, still more preferably 6 to 9.

In a further embodiment, the invention provides a compound of Structure 10:

STRUCTURE 10:

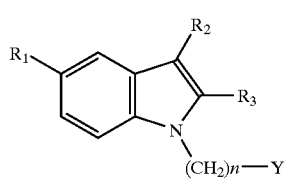

wherein:

n is an integer of from 1 to 12, $R_1$ is an H, $CO_2H$, —$OCH_3$, or —$OCH_2Ph$, $R_2$ is H, $CO_2H$, or CH=$CHCO_2H$, $R_3$ is H or $CO_2H$, and Y is N-linked pyridine-3-carboxylic acid, N-linked pyridine, N-linked quinoline, or N-linked isoquinoline. In further embodiments, n may also be an integer of from 3 to 10, more preferably 5 to 9 and, still more preferably 6 to 9.

In a further embodiment, the invention provides a compound of Structure 12:

STRUCTURE 12:

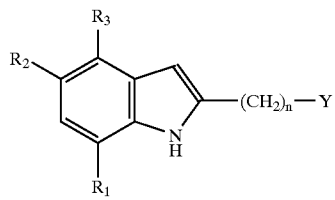

wherein:

n is an integer of from 1 to 12, $R_1$ is H, F, or $NO_2$, $R_2$ is H, $CH_3$, $CF_3$, $NO_2$, phenyl, n-butyl, isopropyl, F, phenyloxy, triphenylmethyl, methoxycarbonyl, methoxy, carboxy, acetyl, or benzoyl, $R_3$ is H or $CF_3$ and Y is N-linked pyridine-3-carboxylic acid, N-linked pyridine, N-linked quinoline, or N-linked isoquinoline. In further embodiments, n may also be an integer of from 3 to 10, more preferably 5 to 9 and, still more preferably 6 to 9.

In a further embodiment, the invention provides a compound of Structure 14:

STRUCTURE 14:

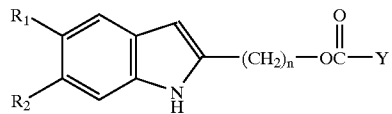

wherein:

n is an integer of from 1 to 12, $R_1$ is H, phenyloxy, isopropyl, acetyl, or benzoyl, $R_2$ is H or $CF_3$, and Y is 3-(dimethylamino)phenyl, 3-(trimethylammonio)phenyl, 4-(dimethylamino)phenyl, 4-(trimethylammonio)phenyl, 2-(phenyl)phenyl, diphenylmethyl, 3-pyridyl, 4-pyridyl, or pyridine-3-methyl. In further embodiments, n may also be an integer of from 3 to 10, more preferably 5 to 9 and, still more preferably 6 to 9.

In a further embodiment, the invention provides a compound of Structure 16:

STRUCTURE 16:

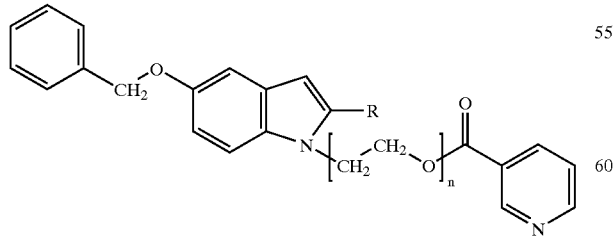

wherein R is H or $CO_2CH_3$ and n is an integer of from 1 to 4, more preferably 2 to 3, and even more preferably, n is 3.

In a further embodiment, the invention provides a compound of Structure 18:

STRUCTURE 18:

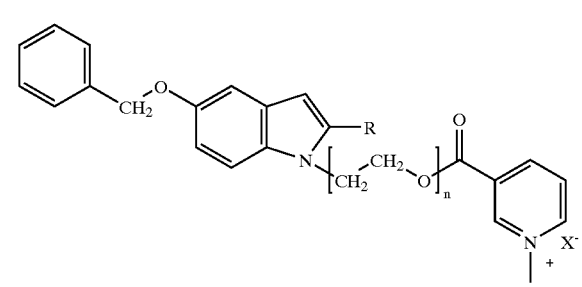

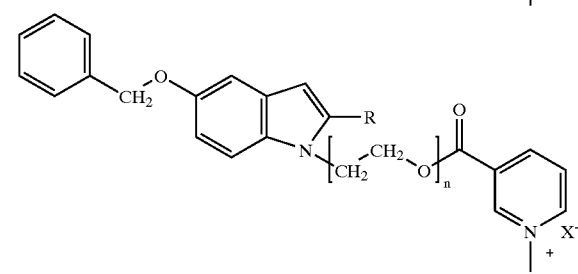

wherein R is H or $CO_2CH_3$ and n is an integer of from 1 to 4, more preferably 2 to 3, and even more preferably, n is 3.

In further preferred embodiments of the invention herein, compounds of the structures denoted in Tables 102–128 as Compounds 1–274 were synthesized utilizing the methods disclosed herein. For Compounds 1–274, structures denoted in FIG. 6 as Fragments I–X each represent an active molecule, as defined previously herein, which can be included in the compounds of the present invention as further described in the respective Tables. In Fragments I–X of FIG. 6, the point of attachment for the linker compound is at the nitrogen.

In the chemical structures that follow, and as intended for the compounds of this invention, the symbol $X^-$ and $P^-$ designate generally the presence of an anion. As contemplated by the present invention; the type of anion in the compounds of this invention is not critical. The anions present in the compounds of this may be comprised of any such moieties known generally to one of skill in the art or that follow from the synthesis methods disclosed herein.

I

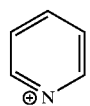

II

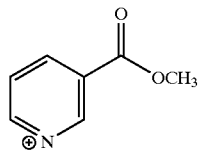

III

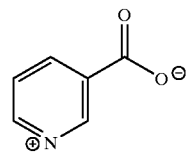

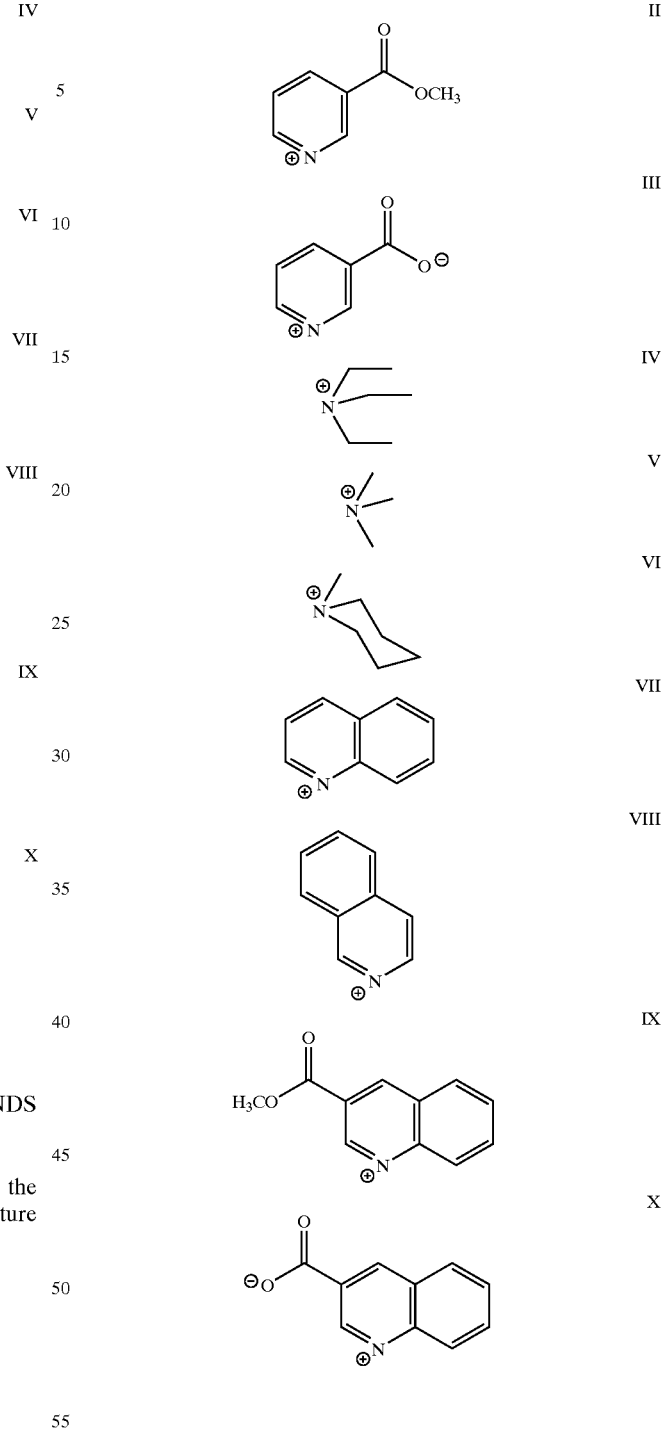

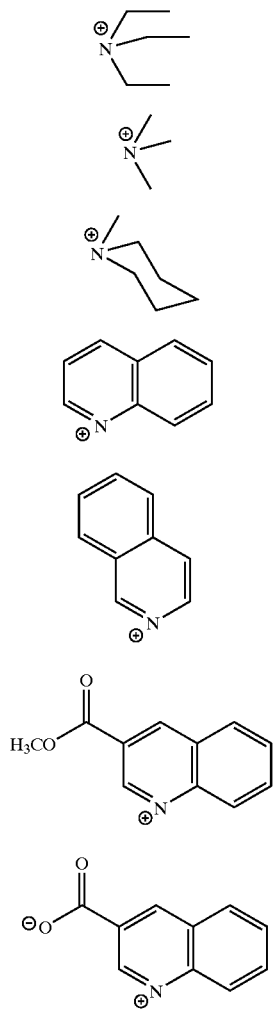

FIG. 6: FRAGMENTS UTILIZED IN COMPOUNDS 1–274

In preferred embodiments of the invention herein, the compounds of the present invention correspond to Structure 100:

Structure 100:

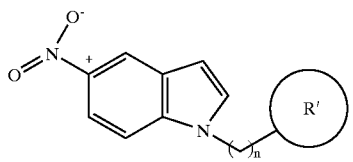

wherein R' is:

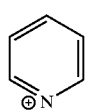

and n is an integer of from 1 to t2. N may also be from 3 to 10, more preferably 5 to 9 and, still more preferably 6 to 9.

In further preferred embodiments of the invention herein, the compounds of the present invention correspond to the structures set out in Structure 100 and as further defined in Table 100. For those compounds that correspond to Structure 100, n may also be an integer of from 1 to 12, more preferably, from 3 to 10, more preferably from 5 to 9 and, still more preferably from 6 to 9.

Structure 100:

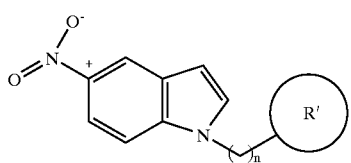

TABLE 100

SUBSTITUENT GROUPS FOR COMPOUNDS 1-24

| R' | n = | | | | | |
|---|---|---|---|---|---|---|
|  | 3 | 4 | 5 | 6 | 7 | 8 | 9 |
| I | 1 | 2 | 3 | 4 | 5 | 6 | 7 |
| II | 8 | 9 | 10 | 11 | 12 | 13 | 14 |
| III | 15 | 16 | 17 | 18 | 19 | 20 | 21 |
| IV |  |  |  |  | 22 |  |  |
| V |  |  |  |  | 23 |  |  |
| VI |  |  |  |  | 24 |  |  |

In the above Table, R' corresponds to a Fragment as previously defined in FIG. 6 and n indicates the number of linker groups separating the two tethered active molecule groups in the compound.

As set out below in relation to Compounds 25-274, Fragments A-G are set out in FIG. 8. The group denoted R in A-G of FIG. 8 can be a benzyl group, a methyl group or a hydrogen. The point of attachment of the linker group to Fragments A-G is at the nitrogen group.

In one embodiment, the compounds of the present invention correspond to compounds of Structure 101. For those compounds that correspond to Structure 101, n is an integer of from 1 to 12, more preferably from 3 to 10, more preferably from 5 to 9 and, still more preferably from 6 to 9. The point of attachment of the linker group for both R1 and R' is at the respective nitrogen groups of each illustrated fragment.

Structure 101:

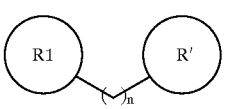

wherein R' is:

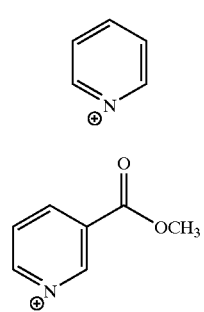

I

II

-continued

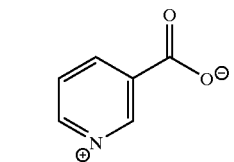

III

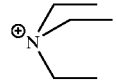

IV

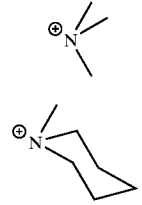

V

VI

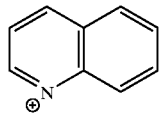

VII

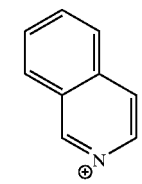

VIII

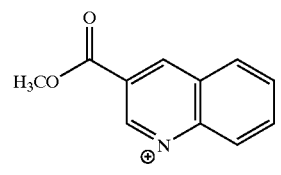

IX

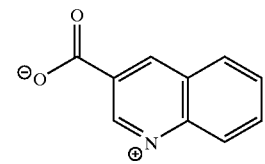

X wherein R1 is:

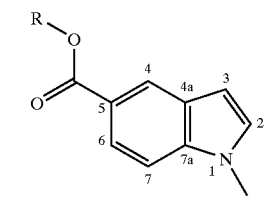

A

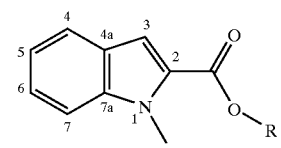

B

-continued

C

D

E

F

G wherein the R group in Fragments A–G is a benzyl group, a methyl group or a hydrogen., In one embodiment of the invention herein, the compounds of the present invention may include the Fragments illustrated below in FIG. 8.

A

B

-continued

C

D

E

F

G

FIG. 8: FRAGMENTS A–G IN COMPOUNDS 25–274

In further preferred embodiments of the invention herein, the compounds of the present invention correspond to the structures set out in Structure 102. For those compounds that correspond to Structure 102, n is an integer of from i to 12, from 3 to 10, more preferably from 5 to .9, and still more preferably from 6 to 9. In further embodiments, the compounds herein correspond to Structure 102, as further set out in Table 102.

STRUCTURE 102:

TABLE 102

SUBSTITUENT GROUPS FOR COMPOUNDS 25–48

| R' | n = 4 | n = 6 | n = 8 |
| --- | --- | --- | --- |
| I | 25 | 26 | 27 |
| I* | 28 | 29 | 30 |
| II | 31 | 32 | 33 |

TABLE 102-continued

SUBSTITUENT GROUPS FOR COMPOUNDS 25–48

| R' | n = 4 | 6 | 8 |
|---|---|---|---|
| III* | 34 | 35 | 36 |
| VII | 37 | 38 | 39 |
| VII* | 40 | 41 | 42 |
| VIII | 43 | 44 | 45 |
| VIII* | 46 | 47 | 48 |

In the above table, R' corresponds to a Fragment as previously defined in FIG. 6, A corresponds to a fragment as previously defined in FIG. 8, and n indicates the number of linker groups separating Groups R' and A in the respective compounds. Groups I, II, VII, VIII each have a benzyl group and Groups I*, III*, VII*, VIII* each have a hydrogen, respectively in the position designated R in Fragment A of FIG. 8.

In further preferred embodiments of the invention herein the compounds of the present invention correspond to the structures set out in Structure 104. For those compounds that correspond to Structure 104, n is an integer of from 1 to 12, from 3 to 10, more preferably from 5 to 9, and still more preferably from 6 to 9. In further embodiments, the compounds herein correspond to Structure 104, as further set out in Table 104.

STRUCTURE 104:

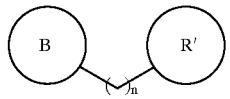

TABLE 104

SUBSTITUENT GROUPS FOR COMPOUNDS 49–66

| R' | n = 4 | 6 | 8 |
|---|---|---|---|
| I | 49 | 50 | 51 |
| I* | 52 | 53 | 54 |
| VII | 55 | 56 | 57 |
| VII* | 58 | 59 | 60 |
| VIII | 61 | 62 | 63 |
| VIII* | 64 | 65 | 66 |

In the above Table, R' corresponds to a Fragment as previously defined in FIG. 6, B corresponds to a Fragment as previously defined in FIG. 8, and n indicates the number of linker groups separating Groups R' and B in the respective compounds. Groups I, VII, VIII each have a benzyl group and Groups I*, VII*, VIII* each have a hydrogen, respectively, in the-position designated R in Fragment B of FIG. 8.

In further preferred embodiments of the invention herein, the compounds of the present invention correspond to the structures set out in Structure 106. For those compounds that correspond to Structure 106, n is an integer of from 1 to 12, from 3 to 10, more preferably from 5 to 9, and still more preferably from 6 to 9. In further embodiments, the compounds herein correspond to Structure 106, as further set out in Table 106.

STRUCTURE 106:

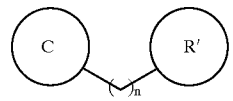

TABLE 106

SUBSTITUENT GROUPS FOR COMPOUNDS 67–90

| R' | n = 4 | 6 | 8 |
|---|---|---|---|
| I | 67 | 68 | 69 |
| I* | 70 | 71 | 72 |
| II | 73 | 74 | 75 |
| III* | 76 | 77 | 78 |
| VII | 79 | 80 | 81 |
| VII* | 82 | 83 | 84 |
| VIII | 85 | 86 | 87 |
| VIII* | 88 | 89 | 90 |

In the above table, R' corresponds to a Fragment as previously defined in FIG. 6, C corresponds to a Fragment as previously defined in FIG. 8, and n indicates the number of linker groups separating Groups R' and C in the respective compounds. Groups I, II, VII, VIII each have a benzyl group and Groups I*, II*, VII*, VII* each have a hydrogen, respectively, in the position designated R in Fragment C of FIG. 8.

In further preferred embodiments of the invention herein, the compounds of the present invention correspond to the structures set out in Structure 108. For those compounds that correspond to Structure 108, n is an integer of from 1 to 12, from 3 to 10, more preferably from 5 to 9, and still more preferably from 6 to 9. In further embodiments, the compounds herein correspond to Structure 108, as further set out in Table 108.

STRUCTURE 108:

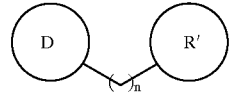

TABLE 108

SUBSTITUENT GROUPS FOR COMPOUNDS 91–108

| R' | n = 4 | 6 | 8 |
|---|---|---|---|
| I | 91 | 92 | 93 |
| I* | 94 | 95 | 96 |
| VII | 97 | 98 | 99 |
| VII* | 100 | 101 | 102 |
| VIII | 103 | 104 | 105 |
| VIII* | 106 | 107 | 108 |

In the above Table, R' corresponds to a Fragment as previously defined in FIG. 6, D corresponds to a fragment as previously defined in FIG. 8, and n indicates the number of linker groups separating Groups R' and D in the compound. Groups I, VII, VIII each have a benzyl group and Groups I*, VII*, VIII* each have a hydrogen, respectively, in the position designated R in Fragment D of FIG. 8.

In further preferred embodiments of the invention herein, the compounds of the present invention correspond to the structures set out in Structure 110. For those compounds that correspond to Structure 110, n is an integer of from 1 to 12, from 3 to 10, more preferably from 5 to 9, and still more preferably from 6 to 9. In further embodiments, the compounds herein correspond to Structure 110, as further set out in Table 110.

STRUCTURE 110:

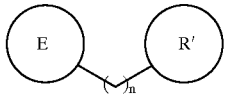

TABLE 110

SUBSTITUENT GROUPS FOR COMPOUNDS 109–126

| | n = | | |
|---|---|---|---|
| R' | 4 | 6 | 8 |
| I | 109 | 110 | 111 |
| I* | 112 | 113 | 114 |
| VII | 115 | 116 | 117 |
| VII* | 118 | 119 | 120 |
| VIII | 121 | 122 | 123 |
| VIII* | 124 | 125 | 126 |

In the above Table, R' corresponds to a Fragment as previously defined in FIG. 6, E corresponds to a Fragment as previously defined in FIG. 8, and n indicates the number of linker groups separating Groups R' and E in the respective compounds. Groups I, VII, VIII each have a benzyl group and Groups I*, VII*, VIII* each have a hydrogen, respectively in the position designated R in Fragment E of FIG. 8.

In further preferred embodiments of the invention herein, the compounds of the present invention correspond to the structures set out in Structure 112. For those compounds that correspond to Structure 112, n is an integer of from 1 to 12, from 3 to 10, more preferably from 5 to 9, and still more preferably from 6 to 9. In further embodiments, the compounds herein correspond to Structure 112, as further set out in Table 112.

STRUCTURE 112:

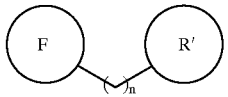

TABLE 112

SUBSTITUENT GROUPS FOR COMPOUNDS 127–144

| | n = | | |
|---|---|---|---|
| R' | 4 | 6 | 8 |
| I | 127 | 128 | 129 |
| I* | 130 | 131 | 132 |
| VII | 133 | 134 | 135 |
| VII* | 136 | 137 | 138 |
| VIII | 139 | 140 | 141 |
| VIII* | 142 | 143 | 144 |

In the above Table, R' corresponds to a Fragment as previously defined in FIG. 6, F corresponds to a Fragment as previously defined in FIG. 8, and n indicates the number of linker groups separating Groups R' and F in the respective compounds. Groups I, VI, VIII each have a benzyl group and Groups I*, VII*, VIE* each have a hydrogen, respectively, in the position designated R in Fragment F of FIG. 8.

In further preferred embodiments of the invention herein, the compounds of the present invention correspond to the structures set out in Structure 114. For those compounds that correspond to Structure 114, n is an integer of from 1 to 12, from 3 to 10, more preferably from 5 to 9, and still more preferably from 6 to 9. In further embodiments, the compounds herein correspond to Structure 114, as further set out in Table 114.

STRUCTURE 114:

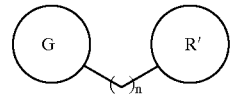

TABLE 114

SUBSTITUENT GROUPS FOR COMPOUNDS 145–162

| | n = | | |
|---|---|---|---|
| R' | 4 | 6 | 8 |
| I | 145 | 146 | 147 |
| I* | 148 | 149 | 150 |
| VII | 151 | 152 | 153 |
| VII* | 154 | 155 | 156 |
| VIII | 157 | 158 | 159 |
| VIII* | 160 | 161 | 162 |

In the above Table, R' corresponds to a Fragment as previously defined in FIG. 6, G corresponds to a Fragment as previously defined in FIG. 8, and n indicates the number of linker groups separating Groups R' and G in the respective compounds. Groups I, VII, VIII each have a benzyl group and Groups I*, VII*, VIII* each have a hydrogen, respectively, in the position designated R in Fragment G of FIG. 8.

In further preferred embodiments of the invention herein, the compounds of the present invention correspond to the structures set out in Structure 116. For those compounds that correspond to Structure 116, n is an integer of from 1 to 12, from 3 to 10, more preferably from 5 to 9, and still more preferably from 6 to 9. In further embodiments, the compounds herein correspond to Structure 116, as further set out in Table 116.

STRUCTURE 116:

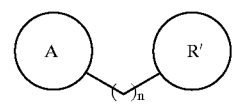

TABLE 116

SUBSTITUENT GROUPS FOR COMPOUNDS 163–178

| | n = | | | |
|---|---|---|---|---|
| R' | 3 | 5 | 7 | 9 |
| I | 163 | 164 | 165 | 166 |
| I* | 167 | 168 | 169 | 170 |

TABLE 116-continued

SUBSTITUENT GROUPS FOR COMPOUNDS 163–178

| R' | n = 3 | 5 | 7 | 9 |
|---|---|---|---|---|
| II | 171 | 172 | 173 | 174 |
| III* | 175 | 176 | 177 | 178 |

In the above Table, R' corresponds to a Fragment as previously defined in FIG. 6, A corresponds to a Fragment as previously defined in FIG. 8, and n indicates the number of linker groups separating Groups R' and A in the respective compounds. Groups I, II each have a methyl group and Groups I*, II* each have a hydrogen, respectively, in the position designated R in Fragment A of FIG. 8.

In further preferred embodiments of the invention herein, the compounds of the present invention correspond to the structures set out in Structure 118. For those compounds that correspond to Structure 118, n is an integer of from 1 to 12, from 3 to 10, more preferably from 5 to 9, and still more preferably from 6 to 9. In further embodiments, the compounds herein correspond to Structure 118, as further set out in Table 118.

STRUCTURE 118:

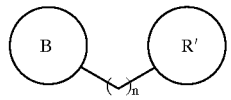

TABLE 118

SUBSTITUENT GROUPS FOR COMPOUNDS 179–194

| R' | n = 3 | 5 | 7 | 9 |
|---|---|---|---|---|
| I | 179 | 180 | 181 | 182 |
| I* | 183 | 184 | 185 | 186 |
| II | 187 | 188 | 189 | 190 |
| III* | 191 | 192 | 193 | 194 |

In the above Table, R' corresponds to a Fragment as previously defined in FIG. 6, B corresponds to a Fragment as previously defined in FIG. 8, and n indicates the number of linker groups separating Groups R' and B in the respective compounds. Groups I, II each have a methyl group and Groups I*, III* each have a hydrogen, respectively, in the position designated R in Fragment B of FIG. 8.

In further preferred embodiments of the invention herein, the compounds of the present invention correspond to the structures set out in Structure 120. For those compounds that correspond to Structure 120, n is an integer of from 1 to 12, from 3 to 10, more preferably from 5 to 9, and still more preferably from 6 to 9. In further embodiments, the compounds herein correspond to Structure 120, as further set out in Table 120.

STRUCTURE 120:

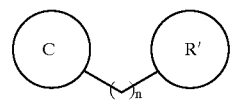

TABLE 120

SUBSTITUENT GROUPS FOR COMPOUNDS 195–210

| R' | n = 3 | 5 | 7 | 9 |
|---|---|---|---|---|
| I | 195 | 196 | 197 | 198 |
| I* | 199 | 200 | 201 | 202 |
| II | 203 | 204 | 205 | 206 |
| III* | 207 | 208 | 209 | 210 |

In the above Table, R' corresponds to a Fragment as previously defined in FIG. 6, C corresponds to a Fragment as previously defined in FIG. 8, and n indicates the number of linker groups separating Groups R' and C in the respective compounds. Groups I, II each have a methyl group and Groups I*, II* each have a hydrogen, respectively, in the position designated R in Fragment C of FIG. 8.

In further preferred embodiments of the invention herein, the compounds of the present invention correspond to the structures set out in Structure 122. For those compounds that correspond to Structure 122, n is an integer of from 1 to 12, from 3 to 10, more preferably from 5 to 9, and still more preferably from 6 to 9.1In further embodiments, the compounds herein correspond to Structure 122, as further set out in Table 122.

STRUCTURE 122:

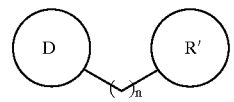

TABLE 122

SUBSTITUENT GROUPS FOR COMPOUNDS 211–226

| R' | n = 3 | 5 | 7 | 9 |
|---|---|---|---|---|
| I | 211 | 212 | 213 | 214 |
| I* | 215 | 216 | 217 | 218 |
| II | 219 | 220 | 221 | 222 |
| III* | 223 | 224 | 225 | 226 |

In the above Table, R' corresponds to a Fragment as previously defined in FIG. 6, D corresponds to a Fragment as previously defined in FIG. 8, and n indicates the number of linker groups separating Groups. R' and D in the respective compounds. Groups I, II each have a methyl group and Groups I, III each have a hydrogen, respectively, in the position designated R in Fragment D of FIG. 8.

In further preferred embodiments of the invention herein, the compounds of the present invention correspond to the structures set out in Structure 124. For those compounds that correspond to Structure 124, n is an integer of from 1 to 12, from 3 to 10, more preferably from 5 to 9, and still more preferably from 6 to 9. In further embodiments, the compounds herein correspond to Structure 124, as further set out in Table 124.

STRUCTURE 124:

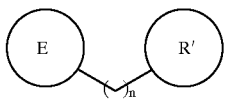

TABLE 124

SUBSTITUENT GROUPS FOR COMPOUNDS 227–242

| R' | n = 3 | 5 | 7 | 9 |
|---|---|---|---|---|
| I | 227 | 228 | 229 | 230 |
| I* | 231 | 232 | 233 | 234 |
| II | 235 | 236 | 237 | 238 |
| III* | 239 | 240 | 241 | 242 |

In the above Table, R' corresponds to a Fragment as previously defined in FIG. 6, E corresponds to a Fragment as previously defined in FIG. 8, and h indicates the number of linker groups separating Groups R' and E in the respective compounds. Groups I, II each have a methyl group and Groups I*, III* each have a hydrogen, respectively, in the position designated R in Fragment E of FIG. 8.

In further preferred embodiments of the invention herein, the compounds of the present invention correspond to the structures set out in Structure 126. For those compounds that correspond to Structure 126, n is an integer of from 1 to 12, from 3 to 10, more preferably from 5 to 9, and still more preferably from 6 to 9. In further embodiments, the compounds herein correspond to Structure 126, as further set out in Table 126.

STRUCTURE 126:

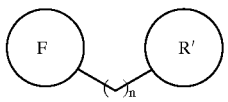

TABLE 126

SUBSTITUENT GROUPS FOR COMPOUNDS 243–258

| R' | n = 3 | 5 | 7 | 9 |
|---|---|---|---|---|
| I | 243 | 244 | 245 | 246 |
| I* | 247 | 248 | 249 | 250 |
| II | 251 | 252 | 253 | 254 |
| III* | 255 | 256 | 257 | 258 |

In the above Table R' corresponds to a Fragment as previously defined in FIG. 6, F corresponds to a Fragment as previously defined in FIG. 8, and n indicates the number of linker groups separating Groups R' and F in the respective compounds. Groups I, II each have a methyl group and Groups I*, III* each have a hydrogen, respectively, in the position designated in Fragment F of FIG. 8.

In further embodiments of the invention herein, the compounds of the present invention corresponds to the structures set out in Structure 128. For those compounds that correspond to Structure 128, n is an integer of from 1 to 12, from 3 to 10, more preferably from 5 to 9, and still more preferably from 6 to 9. In further embodiments, the compounds herein correspond to Structure 128, as further set out in Table 128.

STRUCTURE 128:

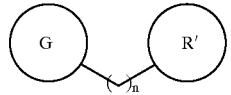

TABLE 128

SUBSTITUENT GROUPS FOR COMPOUNDS 259–274

| R' | n = 3 | 5 | 7 | 9 |
|---|---|---|---|---|
| I | 259 | 260 | 261 | 262 |
| I* | 263 | 264 | 265 | 266 |
| II | 267 | 268 | 269 | 270 |
| III* | 271 | 272 | 273 | 274 |

In the above Table, R' corresponds to a Fragment as previously defined in FIG. 6, G corresponds to, a Fragment as previously defined in FIG. 6, and n indicates the number of linker groups separating Groups R' and G in the respective compounds. Groups I, II each have a methyl group and Groups I*, III* each have a hydrogen, respectively, in the position designated R in Fragment G of FIG. 8.

As used herein, the following terms are defined as follows: Ph: phenyl; 1-propyl=isopropyl; OPh=O-Phenyl; and diNO$_2$=dinitric.

In further embodiments, the compounds of the present invention preferably correspond to compounds of the Structure 130 wherein n is an integer of from 1 to 12, more preferably, from 3 to 10, more preferably from 5 to 9 and, still more preferably from 6 to 9. Further preferred embodiments of the compounds corresponding to Structure 130 are set out in Table 130.

STRUCTURE 130:

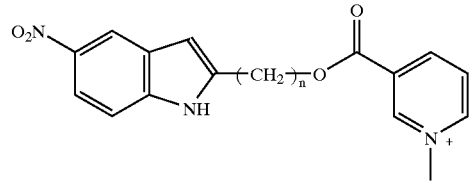

TABLE 130

COMPOUNDS CORRESPONDING TO STRUCTURE 130

| n = 3 | 4 | 5 | 6 | 7 | 8 | 9 |
|---|---|---|---|---|---|---|
| 275 | 276 | 277 | 278 | 279 | 280 | 281 |

In further embodiments, the compounds of the present invention preferably correspond to compounds of the Structure 132 wherein n is an integer of from 1 to 12, more preferably, from 3 to 10, more preferably from 5 to 9 and, still more preferably from 6 to 9 and wherein and R is 5-H, 6-CF$_3$, 5-CH$_3$, 5,7-diF, 5,7-diNO$_2$, 5-Butyl, 5-iPropyl, 5-Phenyl, 5-NO$_2$, 5-Trityl, 5-F, 5-OPh, 5-COPh, 5-CF$_3$, 5-COCH$_3$, 5-OCH$_3$, 5-COOCH, or 5-COOH.

Further preferred embodiments of the compounds corresponding to Structure 132 are set out in Table 132.

STRUCTURE 132:

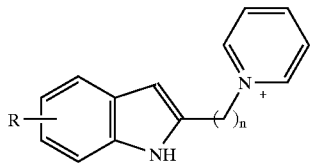

TABLE 132

COMPOUNDS 282–389 CORRESPONDING TO STRUCTURE 132

| R | n = 3 | 4 | 5 | 6 | 7 | 8 |
|---|---|---|---|---|---|---|
| 5-H | 282 | 283 | 284 | 285 | 286 | 287 |
| 6-CF$_3$ | 288 | 289 | 290 | 291 | 292 | 293 |
| 5-CH$_3$ | 294 | 295 | 296 | 297 | 298 | 299 |
| 5,7-diF | 300 | 301 | 302 | 303 | 304 | 305 |
| 5,7-diNO$_2$ | 306 | 307 | 308 | 309 | 310 | 311 |
| 5-Butyl | 312 | 313 | 314 | 315 | 316 | 317 |
| 5-iPropyl | 318 | 319 | 320 | 321 | 322 | 323 |
| 5-Phenyl | 324 | 325 | 326 | 327 | 328 | 329 |
| 5-NO$_2$ | 330 | 331 | 332 | 333 | 334 | 335 |
| 5-Trityl | 336 | 337 | 338 | 339 | 340 | 341 |
| 5-F | 342 | 343 | 344 | 345 | 346 | 347 |
| 5-OPh | 348 | 349 | 350 | 351 | 352 | 353 |
| 5-COPh | 354 | 355 | 356 | 357 | 358 | 359 |
| 5-CF$_3$ | 360 | 361 | 362 | 363 | 364 | 365 |
| 5-COCH$_3$ | 366 | 367 | 368 | 369 | 370 | 371 |
| 5-OCH$_3$ | 372 | 373 | 374 | 375 | 376 | 377 |
| 5-COOCH$_3$ | 378 | 379 | 380 | 381 | 382 | 383 |
| 5-COOH | 384 | 385 | 386 | 387 | 388 | 389 |

In further embodiments, the compounds of the present invention preferably correspond to compounds of the Structure 134 wherein n is an integer of from 1 to 12, more preferably, from 3 to 10, more preferably from 5 to 9 and, still more preferably from 6 to 9 and wherein R is 5-H, 6-CF$_3$, 5-CH$_3$, 5,7-diF, 5,7-diNO$_2$, 5-Butyl, 5-iPropyl, 5-Phenyl, 5-NO$_2$, 5-Trityl, 5-F, 5-OPh, 5-COPh, 5-CF$_3$, 5-COCH$_3$, 5-OCH$_3$, 5-COOCH$_3$, or 5-COOH. Further preferred embodiments of the compounds corresponding to Structure 134 are set out in Table 134.

STRUCTURE 134:

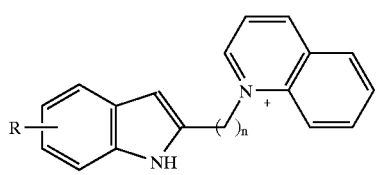

TABLE 134

COMPOUNDS 390–497 CORRESPONDING TO STRUCTURE 134

| R | n = 3 | 4 | 5 | 6 | 7 | 8 |
|---|---|---|---|---|---|---|
| 5-H | 390 | 391 | 392 | 393 | 394 | 395 |
| 6-CF$_3$ | 396 | 397 | 398 | 399 | 400 | 401 |
| 5-CH$_3$ | 402 | 403 | 404 | 405 | 406 | 407 |
| 5,7-diF | 408 | 409 | 410 | 411 | 412 | 413 |
| 5,7-diNO$_2$ | 414 | 415 | 416 | 417 | 418 | 419 |
| 5-Butyl | 420 | 421 | 422 | 423 | 424 | 425 |
| 5-iPropyl | 426 | 427 | 428 | 429 | 430 | 431 |
| 5-Phenyl | 432 | 433 | 434 | 435 | 436 | 437 |
| 5-NO$_2$ | 438 | 439 | 440 | 441 | 442 | 443 |
| 5-Trityl | 444 | 445 | 446 | 447 | 448 | 449 |
| 5-F | 450 | 451 | 452 | 453 | 454 | 455 |
| 5-OPh | 456 | 457 | 458 | 459 | 460 | 461 |
| 5-COPh | 462 | 463 | 464 | 465 | 466 | 467 |
| 5-CF$_3$ | 468 | 469 | 470 | 471 | 472 | 473 |
| 5-COCH$_3$ | 474 | 475 | 476 | 477 | 478 | 479 |
| 5-OCH$_3$ | 480 | 481 | 482 | 483 | 484 | 485 |
| 5-COOCH$_3$ | 486 | 487 | 488 | 489 | 490 | 491 |
| 5-COOH | 492 | 493 | 494 | 495 | 496 | 497 |

In further embodiments, the compounds of the present invention preferably correspond to compounds of the Structure 136 wherein n is an integer of from 1 to 12, more preferably, from 3 to 10, more preferably from 5 to 9 and, still more preferably from 6 to 9 and wherein R is 5-H, 6-CF$_3$, 5-CH$_3$, 5,7-diF, 5,7-diNO$_2$, 5-Butyl, 5-iPropyl, 5-Phenyl, 5-NO$_2$, 5-Trityl, 5-F, 5-OPh, 5-COPh, 5-CF$_3$, 5-COCH$_3$, 5-OCH$_3$, 5-COOCH$_3$, or 5-COOH. Further preferred embodiments of the compounds corresponding to Structure 136 are set out in Table 136.

STRUCTURE 136:

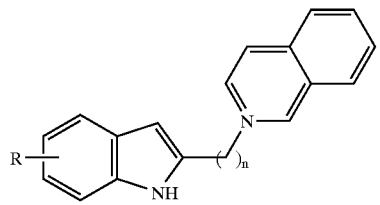

TABLE 136

COMPOUNDS 498–605 CORRESPONDING TO STRUCTURE 136

| R | n = 3 | 4 | 5 | 6 | 7 | 8 |
|---|---|---|---|---|---|---|
| 5-H | 498 | 499 | 500 | 501 | 502 | 503 |
| 6-CF$_3$ | 504 | 505 | 506 | 507 | 508 | 509 |
| 5-CH$_3$ | 510 | 511 | 512 | 513 | 514 | 515 |
| 5,7-diF | 516 | 517 | 518 | 519 | 520 | 521 |
| 5,7-diNO$_2$ | 522 | 523 | 524 | 525 | 526 | 527 |
| 5-Butyl | 528 | 529 | 530 | 531 | 532 | 533 |
| 5-iPropyl | 534 | 535 | 536 | 537 | 538 | 539 |
| 5-Phenyl | 540 | 541 | 542 | 543 | 544 | 545 |
| 5-NO$_2$ | 546 | 547 | 548 | 549 | 550 | 551 |
| 5-Trityl | 552 | 553 | 554 | 555 | 556 | 557 |
| 5-F | 558 | 559 | 560 | 561 | 562 | 563 |
| 5-OPh | 564 | 565 | 566 | 567 | 568 | 569 |
| 5-COPh | 570 | 571 | 572 | 573 | 574 | 575 |
| 5-CF$_3$ | 576 | 577 | 578 | 579 | 580 | 581 |
| 5-COCH$_3$ | 582 | 583 | 584 | 585 | 586 | 587 |
| 5-OCH$_3$ | 588 | 589 | 590 | 591 | 592 | 593 |

TABLE 136-continued

COMPOUNDS 498–605 CORRESPONDING TO STRUCTURE 136

| R | n = 3 | 4 | 5 | 6 | 7 | 8 |
|---|---|---|---|---|---|---|
| 5-COOCH$_3$ | 594 | 595 | 596 | 597 | 598 | 599 |
| 5-COOH | 600 | 601 | 602 | 603 | 604 | 605 |

In further embodiments, the compounds of the present invention preferably correspond to compounds of the Structure 138 wherein n is an integer of from 1 to 12, more preferably, from 3 to 10, more preferably from 5 to 9 and, still more preferably from 6 to 9 and wherein R is 5-CF$_3$, 5-OPh, 5-iPropyl, 5-COCH$_3$, or 5-COPh and Y is 3-N,N-dimethylaminophenyl (3-N,N-diCH$_3$), 4N,N-dimethylaminophenyl (4-N,N-diCH$_3$), or 2-Ph. Further preferred embodiments of the compounds corresponding to Structure 138 are set out in Table 138.

STRUCTURE 138:

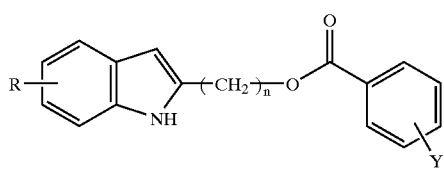

TABLE 138

COMPOUNDS 606–650 CORRESPONDING TO STRUCTURE 138

| R | n = 4 | 7 | 8 | Y |
|---|---|---|---|---|
| 5-CF$_3$ | 606 | 607 | 608 | 3-N,N-DiCH$_3$ |
| 5-CF$_3$ | 609 | 610 | 611 | 4-N,N-DiCH$_3$ |
| 5-CF$_3$ | 612 | 613 | 614 | 2-Ph |
| 5-OPh | 615 | 616 | 617 | 3-N,N-DiCH$_3$ |
| 5-OPh | 618 | 619 | 620 | 4-N,N-DiCH$_3$ |
| 5-OPh | 621 | 622 | 623 | 2-Ph |
| 5-iPropyl | 624 | 625 | 626 | 3-N,N-DiCH$_3$ |
| 5-iPropyl | 627 | 628 | 629 | 4-N,N-DiCH$_3$ |
| 5-iPropyl | 630 | 631 | 632 | 2-Ph |
| 5-COCH$_3$ | 633 | 634 | 635 | 3-N,N-DiCH$_3$ |
| 5-COCH$_3$ | 636 | 637 | 638 | 4-N,N-DiCH$_3$ |
| 5-COCH$_3$ | 639 | 640 | 641 | 2-Ph |
| 5-COPh | 642 | 643 | 644 | 3-N,N-DiCH$_3$ |
| 5-COPh | 645 | 646 | 647 | 4-N,N-DiCH$_3$ |
| 5-COPh | 648 | 649 | 650 | 2-Ph |

In further embodiments, the compounds of the present invention preferably correspond to compounds of the Structure 140 wherein n is an integer of from 1 to 12, more preferably, from 3 to 10, more preferably from 5 to 9 and, still more preferably from 6 to 9 and wherein R is 5-CF$_3$, 5-OPh, 5-iPropyl, 5-COCH$_3$ or 5-COPh, and Z is CH(Ph)$_2$ or 3-Pyridyl. Further preferred embodiments of the compounds corresponding to Structure 140 are set out in Table 140.

STRUCTURE 140:

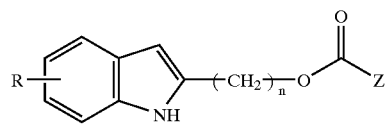

TABLE 140

COMPOUNDS 651–680 CORRESPONDING TO STRUCTURE 140

| R | n = 4 | 7 | 8 | Z |
|---|---|---|---|---|
| 5-CF$_3$ | 651 | 652 | 653 | CH(Ph)$_2$ |
| 5-CF$_3$ | 654 | 655 | 656 | 3-Pyridyl |
| 5-OPh | 657 | 658 | 659 | CH(Ph)$_2$ |
| 5-OPh | 660 | 661 | 662 | 3-Pyridyl |
| 5-iPropyl | 663 | 664 | 665 | CH(Ph)$_2$ |
| 5-iPropyl | 666 | 667 | 668 | 3-Pyridyl |
| 5-COCH$_3$ | 669 | 670 | 671 | CH(Ph)$_2$ |
| 5-COCH$_3$ | 672 | 673 | 674 | 3-Pyridyl |
| 5-COPh | 675 | 676 | 677 | CH(Ph)$_2$ |
| 5-COPh | 678 | 679 | 680 | 3-Pyridyl |

In further embodiments, the compounds of the present invention preferably correspond to compounds of the Structure 142 wherein n is an integer of from 1 to 12, more preferably, from 3 to 10, more preferably from 5 to 9 and, still more preferably from 6 to 9 and wherein R is 6-CF$_3$, 5-OPh, 5-iPropyl, 5-COCH$_3$, or 5-COPh. Further preferred embodiments of the compounds corresponding to Structure 142 are set out in Table 142.

STRUCTURE 142:

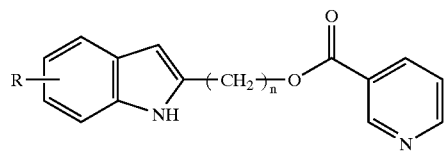

TABLE 142

COMPOUNDS 681–695 CORRESPONDING TO STRUCTURE 142

| R | n = 4 | 7 | 8 |
|---|---|---|---|
| 6-CF$_3$ | 681 | 682 | 683 |
| 5-OPh | 684 | 685 | 686 |
| 5-iPropyl | 687 | 688 | 689 |
| 5-COCH$_3$ | 690 | 691 | 692 |
| 5-COPh | 693 | 694 | 695 |

In further embodiments, the compounds of the present invention preferably correspond to compounds of the Structure 144 wherein n is an integer of from 1 to 12, more preferably, from 3 to 10, more preferably from 5 to 9 and, still more preferably from 6 to 9 and wherein R is 6-CF$_3$, 5-OPh, 5-iPropyl, 5-COCH$_3$, or 5-COPh. Further preferred embodiments of the compounds corresponding to Structure 144 are set out in Table 144.

STRUCTURE 144:

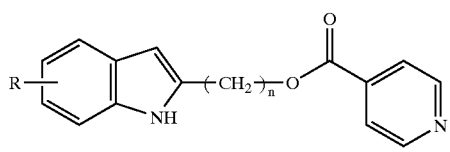

TABLE 144

COMPOUNDS 696–710 CORRESPONDING TO STRUCTURE 144

| | n = | | |
|---|---|---|---|
| R | 4 | 7 | 8 |
| 6-CF₃ | 696 | 697 | 698 |
| 5-OPh | 699 | 700 | 701 |
| 5-iPropyl | 702 | 703 | 704 |
| 5-COCH₃ | 705 | 706 | 707 |
| 5-COPh | 708 | 709 | 710 |

In further embodiments, the compounds of the present invention preferably correspond to compounds of the Structure 146 wherein n is an integer of from 1 to 12, more preferably, from 3 to 10, more preferably from 5 to 9 and, still more preferably from 6 to 9. Further preferred embodiments of the compounds corresponding to Structure 146 are set out in Table 146.

STRUCTURE 146:

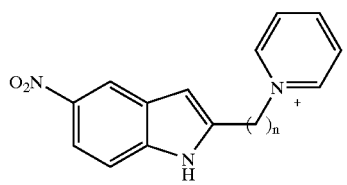

TABLE 146

COMPOUNDS 711–714 CORRESPONDING TO STRUCTURE 146

| n = | | | |
|---|---|---|---|
| 3 | 4 | 5 | 8 |
| 711 | 712 | 713 | 714 |

In further embodiments, the compounds of the present invention preferably correspond to compounds of the Structure 148, as further defined in Table 148.

STRUCTURE 148:

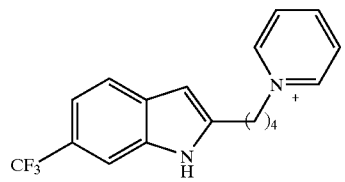

TABLE 148

COMPOUND 715 CORRESPONDING TO STRUCTURE 148

| 715 |
|---|

In further embodiments, the compounds of the present invention preferably correspond to compounds of the Structure 150 wherein n is an integer of from 1 to 12, more preferably, from 3 to 10, more preferably from 5 to 9 and, still more preferably from 6 to 9.

Further preferred embodiments of the compounds corresponding to Structure 150 are set out in Table 150.

STRUCTURE 150:

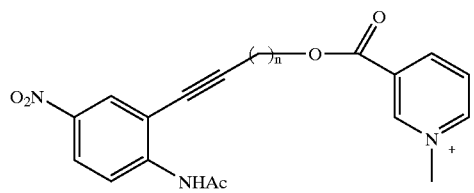

TABLE 150

COMPOUNDS 716–718 CORRESPONDING TO STRUCTURE 150

| n = | | |
|---|---|---|
| 2 | 3 | 4 |
| 716 | 717 | 718 |

In further embodiments, the compounds of the present invention preferably correspond to compounds of the Structure 152 wherein n is an integer of from 1 to 12, more preferably, from 3 to 10, more preferably from 5 to 9 and, still more preferably from 6 to 9.

Further preferred embodiments of the compounds corresponding to Structure 152 are set out in Table 152.

STRUCTURE 152:

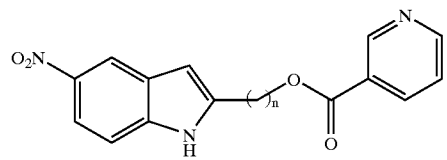

TABLE 152

COMPOUNDS 719–725 CORRESPONDING TO STRUCTURE 152

| n = | | | | | | |
|---|---|---|---|---|---|---|
| 3 | 4 | 5 | 6 | 7 | 8 | 9 |
| 719 | 720 | 721 | 722 | 723 | 724 | 725 |

In further embodiments, the compounds of the present invention preferably correspond to compounds of the Structure 154 wherein n is an integer of from 1 to 12, more preferably, from 3 to 10, more preferably from 5 to 9 and, still more preferably from 6 to 9 and wherein Z is CH(DiPh), 4-(N,N-dimethylamino)phenyl, CH₂CH₂-(3-pyridyl), or (2-phenyl)-phenyl. Further preferred embodiments of the compounds corresponding to Structure 154 are set out in Table 154.

STRUCTURE 154:

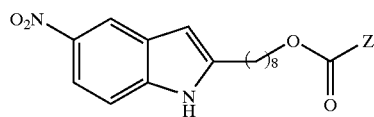

TABLE 154

COMPOUNDS 726–729 CORRESPONDING TO STRUCTURE 154

| Z = | | | |
|---|---|---|---|
| CH(DiPh) | (4-N,N-DiCH$_3$)phenyl | CH$_2$CH$_2$-(3-pyridyl) | (2-phenyl)-phenyl |
| 726 | 727 | 728 | 729 |

In further embodiments, the compounds of the present invention preferably correspond to compounds of the Structure 156 wherein n is an integer of from 1 to 12, more preferably, from 3 to 10, more preferably from 5 to 9 and, still more preferably from 6 to 9 and wherein R is —OCH$_3$ or —OCH$_2$Ph. Further preferred embodiments of the compounds corresponding to Structure 156 are set out in Table 156.

STRUCTURE 156:

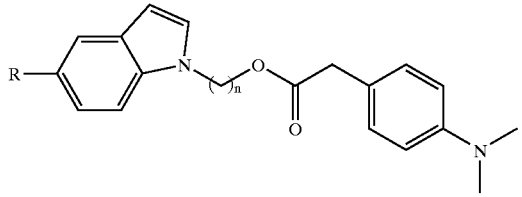

TABLE 156

COMPOUNDS 730–739 CORRESPONDING TO STRUCTURE 156

| | n = | | | | |
|---|---|---|---|---|---|
| R | 4 | 5 | 6 | 7 | 8 |
| —OCH$_3$ | 730 | 731 | 732 | 733 | 734 |
| —OCH$_2$Ph | 735 | 736 | 737 | 738 | 739 |

In further embodiments, the compounds of the present invention preferably correspond to compounds of the Structure 158 wherein n is an integer of from 1 to 12, more preferably, from 3 to 10, more preferably from 5 to 9 and, still more preferably from 6 to 9 and wherein R is —OCH$_3$ or —OCH$_2$Ph. Further preferred embodiments of the compounds corresponding to Structure 158 are set out in Table 158.

STRUCTURE 158:

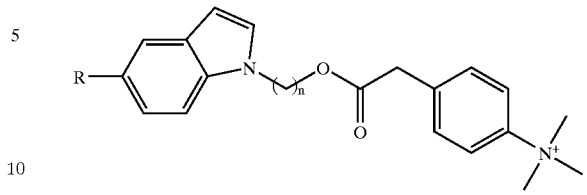

TABLE 158

COMPOUNDS 740–749 CORRESPONDING TO STRUCTURE 158

| | n = | | | | |
|---|---|---|---|---|---|
| R | 4 | 5 | 6 | 7 | 8 |
| —OCH$_3$ | 740 | 741 | 742 | 743 | 744 |
| —OCH$_2$Ph | 745 | 746 | 747 | 748 | 749 |

In further embodiments, the compounds of the present invention preferably correspond to compounds of the Structure 160 wherein n is an integer of from 1 to 12, more preferably, from 3 to 10, more preferably from 5 to 9 and, still more preferably from 6 to 9 and wherein R is —OCH$_3$ or —OCH$_2$Ph. Further preferred embodiments of the compounds corresponding to Structure 160 are set out in Table 160.

STRUCTURE 160:

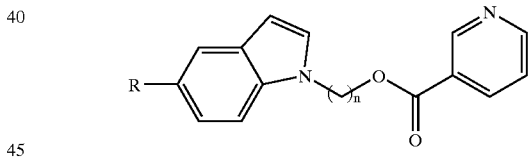

TABLE 160

COMPOUNDS 750–759 CORRESPONDING TO STRUCTURE 160

| | n = | | | | |
|---|---|---|---|---|---|
| R | 4 | 5 | 6 | 7 | 8 |
| —OCH$_3$ | 750 | 751 | 752 | 753 | 754 |
| —OCH$_2$Ph | 755 | 756 | 757 | 758 | 759 |

In further embodiments, the compounds of the present invention preferably correspond to compounds of the Structure 162 wherein n is an integer of from 1 to 12, more preferably, from 3 to 10, more preferably from 5 to 9 and, still more preferably from 6 to 9 and wherein R is —OCH$_3$ or —OCH$_2$Ph. Further preferred embodiments of the compounds corresponding to Structure 162 are set out in Table 162.

STRUCTURE 162:

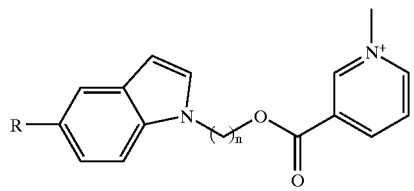

TABLE 162

COMPOUNDS 760–769 CORRESPONDING TO STRUCTURE 162

| | n = | | | | |
|---|---|---|---|---|---|
| R | 4 | 5 | 6 | 7 | 8 |
| —OCH$_3$ | 760 | 761 | 762 | 763 | 764 |
| —OCH$_2$Ph | 765 | 766 | 767 | 768 | 769 |

In further embodiments, the compounds of the present invention preferably correspond to compounds of the Structure 164 wherein n is an Integer of from 1 to 12, more preferably, from 3 to 10, more preferably from 5 to 9 and, still more preferably from 6 to 9 and wherein R is —OCH$_3$ or —OCH$_2$Ph. Further preferred embodiments of the compounds corresponding to Structure 164 are set out in Table 164.

STRUCTURE 164:

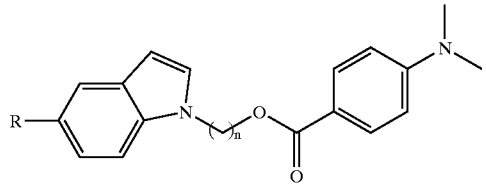

TABLE 164

COMPOUNDS 770–779 CORRESPONDING TO STRUCTURE 164

| | n = | | | | |
|---|---|---|---|---|---|
| R | 4 | 5 | 6 | 7 | 8 |
| —OCH$_3$ | 770 | 771 | 772 | 773 | 774 |
| —OCH$_2$Ph | 775 | 776 | 777 | 778 | 779 |

In further embodiments, the compounds of the present invention preferably correspond to compounds of the Structure 166 wherein n is an integer of from i to 12, more preferably, from 3 to 10, more preferably from 5 to 9 and, still more preferably from 6 to 9 and wherein R is —OCH, or —OCH$_2$Ph. Further preferred embodiments of the compounds corresponding to Structure 166 are set out in Table 166.

STRUCTURE 166:

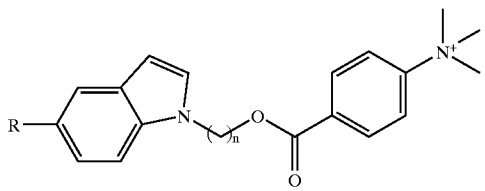

TABLE 166

COMPOUNDS 780–789 CORRESPONDING TO STRUCTURE 166

| | n = | | | | |
|---|---|---|---|---|---|
| R | 4 | 5 | 6 | 7 | 8 |
| —OCH$_3$ | 780 | 781 | 782 | 783 | 784 |
| —OCH$_2$Ph | 785 | 786 | 787 | 788 | 789 |

In further embodiments, the compounds of the present invention preferably correspond to compounds of the Structure 168 wherein n is an integer of from 1 to 12, more preferably, from 3 to 10, more preferably from 5 to 9 and, still more preferably from 6 to 9 and wherein R is —OCH$_3$ or —OCH$_2$Ph. Further preferred embodiments of the compounds corresponding to Structure 168 are set out in Table 168.

STRUCTURE 168:

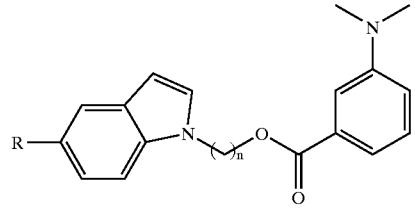

TABLE 168

COMPOUNDS 790–799 CORRESPONDING TO STRUCTURE 168

| | n = | | | | |
|---|---|---|---|---|---|
| R | 4 | 5 | 6 | 7 | 8 |
| —OCH$_3$ | 790 | 791 | 792 | 793 | 794 |
| —OCH$_2$Ph | 795 | 796 | 797 | 798 | 799 |

In further embodiments, the compounds of the present invention preferably correspond to compounds of the Structure 170 wherein n is an integer of from 1 to 12, more preferably, from 3 to 10, more preferably from 5 to 9 and, still more preferably from 6 to 9 and wherein R is —OCH$_3$ or —OCH$_2$Ph. Further preferred embodiments of the compounds corresponding to Structure 170 are set out in Table 170.

STRUCTURE 170:

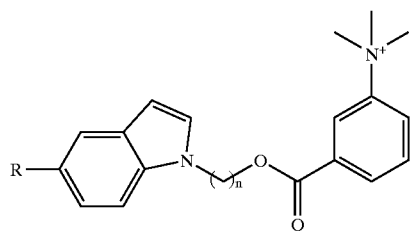

TABLE 170

COMPOUNDS 800–809 CORRESPONDING TO STRUCTURE 170

| | n = | | | | |
|---|---|---|---|---|---|
| R | 4 | 5 | 6 | 7 | 8 |
| —OCH$_3$ | 800 | 801 | 802 | 803 | 804 |
| —OCH$_2$Ph | 805 | 806 | 807 | 808 | 809 |

In further embodiments, the compounds of the present invention preferably correspond to compounds of the Structure 172 wherein n is an integer of from 1 to 12, more preferably, from 3 to 10, more preferably from 5 to 9 and, still more preferably from 6 to 9 and wherein R is —OCH$_3$ and —OCH$_2$ Ph. Further preferred embodiments of the compounds corresponding to Structure 172 are set out in Table 172.

STRUCTURE 172:

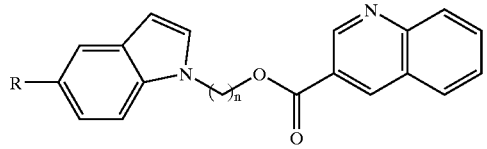

TABLE 172

COMPOUNDS 810–819 CORRESPONDING TO STRUCTURE 172

| | n = | | | | |
|---|---|---|---|---|---|
| R | 4 | 5 | 6 | 7 | 8 |
| —OCH$_3$ | 810 | 811 | 812 | 813 | 814 |
| —OCH$_2$Ph | 815 | 816 | 817 | 818 | 819 |

In further embodiments, the compounds of the present invention preferably correspond to compounds of the Structure 174 wherein n is an integer of from 1 to 12, more preferably, from 3 to 10, more preferably from 5 to 9 and, still more preferably from 6 to 9 and wherein R is —OCH$_3$ and —OCH$_2$ Ph. Further preferred embodiments of the compounds corresponding to Structure 174 are set out in Table 174.

STRUCTURE 174:

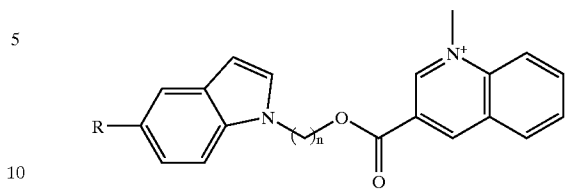

TABLE 174

COMPOUNDS 820–829 CORRESPONDING TO STRUCTURE 174

| | n = | | | | |
|---|---|---|---|---|---|
| R | 4 | 5 | 6 | 7 | 8 |
| —OCH$_3$ | 820 | 821 | 822 | 823 | 824 |
| —OCH$_2$Ph | 825 | 826 | 827 | 828 | 829 |

In further embodiments, the compounds of the present invention preferably correspond to compounds of the Structure 176 wherein n is an integer of from 1 to 12, more preferably, from 3 to 10, more preferably from 5 to 9 and, still more preferably from 6 to 9 and wherein Z is 3-quinoline, 3-(N,N-dimethylamino)phenyl, or 44N,N-dimethylamino)phenyl. Further preferred embodiments of the compounds corresponding to Structure 176 are set out in Table 176.

STRUCTURE 176:

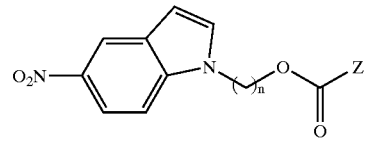

TABLE 176

COMPOUNDS 830–847 CORRESPONDING TO STRUCTURE 176

| | n = | | | | | |
|---|---|---|---|---|---|---|
| Z | 4 | 5 | 6 | 7 | 8 | 9 |
| 3-quinoline | 830 | 831 | 832 | 833 | 834 | 835 |
| 3-(N,N-diCH$_3$)phenyl | 836 | 837 | 838 | 839 | 840 | 841 |
| 4-(N,N-diCH$_3$)phenyl | 842 | 843 | 844 | 845 | 846 | 847 |

In further embodiments, the compounds of the present invention preferably correspond to compounds of the Structure 178 wherein n is an integer of from 1 to 12, more preferably, from 3 to 10, more preferably from 5 to 9 and, still more preferably from 6to 9.

Further preferred embodiments of the compounds corresponding to Structure 178 are set out in Table 178.

STRUCTURE 178:

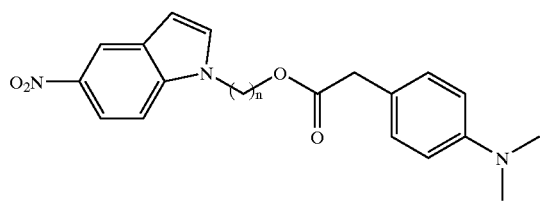

TABLE 178

COMPOUNDS 848–853 CORRESPONDING TO STRUCTURE 178

| N = | | | | | |
|---|---|---|---|---|---|
| 4 | 5 | 6 | 7 | 8 | 9 |
| 848 | 849 | 850 | 851 | 852 | 853 |

In further embodiments, the compounds of the present invention preferably correspond to compounds of the Structure 180 wherein n is an integer of from 1 to 12, more preferably, from 3 to 10, more preferably from 5 to 9 and, still more preferably from 6 to 9.

Further preferred embodiments of the compounds corresponding to Structure 180 are set out in Table 180.

STRUCTURE 180:

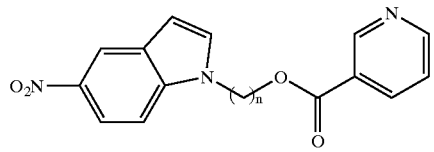

TABLE 180

COMPOUNDS 854–860 CORRESPONDING TO STRUCTURE 180

| n = | | | | | | |
|---|---|---|---|---|---|---|
| 2 | 3 | 4 | 5 | 6 | 7 | 8 |
| 854 | 855 | 856 | 857 | 858 | 859 | 860 |

In further embodiments, the compounds of the present invention preferably correspond to compounds of the Structure 182 wherein n is an integer of from 1 to 12, more preferably, from 3 to 10, more preferably from 5 to 9 and, still more preferably from 6 to 9.

Further preferred embodiments of the compounds corresponding to Structure 182 are set out in Table 182.

STRUCTURE 182:

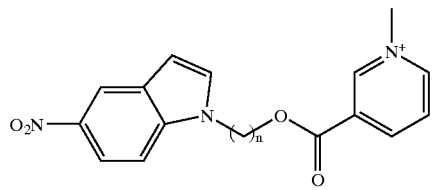

TABLE 182

COMPOUNDS 861–867 CORRESPONDING TO STRUCTURE 182

| n = | | | | | | |
|---|---|---|---|---|---|---|
| 2 | 3 | 4 | 5 | 6 | 7 | 8 |
| 861 | 862 | 863 | 864 | 865 | 866 | 867 |

In further embodiments, the compounds of the present invention preferably correspond to compounds of the Structure 184 wherein n is an integer of from 1 to 12, more preferably, from 3 to 10, more preferably from 5 to 9 and, still more preferably from 6 to 9 and wherein and R is 6-$CF_3$, 5-OPh, 5-$CH(CH_3)_2$, 5-COCH, or 5-COPh. Further preferred embodiments of the compounds corresponding to Structure 184 are set out in Table 184.

STRUCTURE 184:

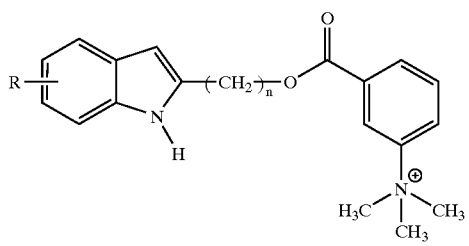

TABLE 184

COMPOUNDS 868–882 CORRESPONDING TO STRUCTURE 184

| R | n = | | |
|---|---|---|---|
| | 4 | 7 | 8 |
| 6-$CF_3$ | 868 | 869 | 870 |
| 5-OPh | 871 | 872 | 873 |
| 5-$CH(CH_3)_2$ | 874 | 875 | 876 |
| 5-$COCH_3$ | 877 | 878 | 879 |
| 5-COPh | 880 | 881 | 882 |

In further embodiments, the compounds of the present invention preferably correspond to compounds of the Structure 186 wherein n is an integer of from 1 to 12, more preferably, from 3 to 10, more preferably from 5 to 9 and, still more preferably from 6 to 9 and wherein R is 6-$CF_3$, 5-OPh, 5-$CH(CH_3)_2$, 5-COCH, or 5-COPh. Further preferred embodiments of the compounds corresponding to Structure 186 are set out in Table 186.

STRUCTURE 186:

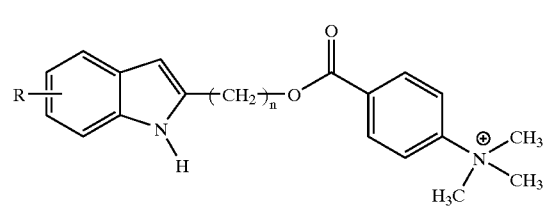

TABLE 186

COMPOUNDS 883–897 CORRESPONDING TO STRUCTURE 186

| | n = | | |
|---|---|---|---|
| R | 4 | 7 | 8 |
| 6-CF$_3$ | 883 | 884 | 885 |
| 5-OPh | 886 | 887 | 888 |
| 5-CH(CH$_3$)$_2$ | 889 | 890 | 891 |
| 5-COCH$_3$ | 892 | 893 | 894 |
| 5-COPh | 895 | 896 | 897 |

In further embodiments, the compounds of the present invention preferably correspond to compounds of the Structure 188 wherein n is an integer of from 1 to 12, more preferably, from 3 to 10, more preferably from 5 to 9 and, still more preferably from 6 to 9 and wherein and R is 6-CF$_3$, 5-OPh, 5-CH(CH$_3$)$_2$, 5-COCH$_3$ or 5-COPh. Further preferred embodiments of the compounds corresponding to Structure 188 are set out in Table 188.

STRUCTURE 188:

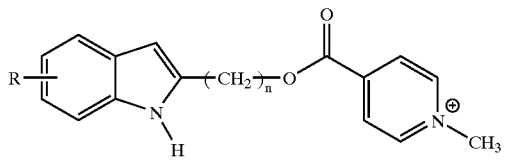

TABLE 188

COMPOUNDS 898–912 CORRESPONDING TO STRUCTURE 188

| | n = | | |
|---|---|---|---|
| R | 4 | 7 | 8 |
| 6-CF$_3$ | 898 | 899 | 900 |
| 5-OPh | 901 | 902 | 903 |
| 5-CH(CH$_3$)$_2$ | 904 | 905 | 906 |
| 5-COCH$_3$ | 907 | 908 | 909 |
| 5-COPh | 910 | 911 | 912 |

In further embodiments, the compounds of the present invention preferably correspond to compounds of the Structure 190 wherein n is an integer of from 1 to 12, more preferably, from 3 to 10, more preferably from 5 to 9 and, still more preferably from 6 to 9 and wherein R is 6-CF$_3$, 5-OPh, 5-CH(CH$_3$)$_2$, 5-COCH$_3$ or 5-COPh. Further preferred embodiments of the compounds corresponding to Structure 190 are set out in Table 190.

STRUCTURE 190:

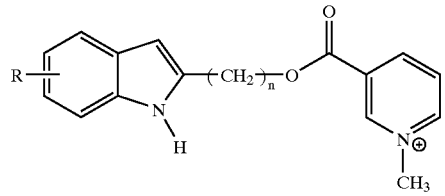

TABLE 190

COMPOUNDS 913–927 CORRESPONDING TO STRUCTURE 190

| | n = | | |
|---|---|---|---|
| R | 4 | 7 | 8 |
| 6-CF$_3$ | 913 | 914 | 915 |
| 5-OPh | 916 | 917 | 918 |
| 5-CH(CH$_3$)$_2$ | 919 | 920 | 921 |
| 5-COCH$_3$ | 922 | 923 | 924 |
| 5-COPh | 925 | 926 | 927 |

In further embodiments, the compounds of the present invention preferably correspond to compounds of the Structure 192 wherein n is an integer of from 11 to 12, more preferably, from 3 to 10, more preferably from 5 to 9 and, still more preferably from 6 to 9 and wherein and R is 6-CF$_3$, 5-OPh, 5-CH(CH$_3$)$_2$, 5-COCH$_3$ or 5-COPh. Further preferred embodiments of the compounds corresponding to Structure 192 are set out in Table 192.

STRUCTURE 192:

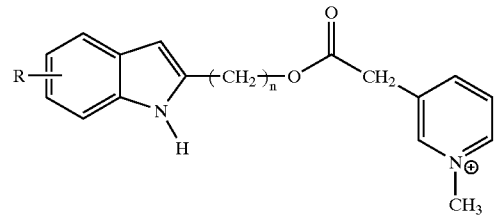

TABLE 192

COMPOUNDS 928–942 CORRESPONDING TO STRUCTURE 192

| | n = | | |
|---|---|---|---|
| R | 4 | 7 | 8 |
| 6-CF$_3$ | 928 | 929 | 930 |
| 5-OPh | 931 | 932 | 933 |
| 5-CH(CH$_3$)$_2$ | 934 | 935 | 936 |
| 5-COCH$_3$ | 937 | 938 | 939 |
| 5-COPh | 940 | 941 | 942 |

In further embodiments, the compounds of the present invention preferably correspond to compounds of the Structure 194 wherein n is an integer of from 1 to 12, more preferably, from 3 to 10, more preferably from 5 to 9 and, still more preferably from 6 to 9 and R$^1$ is an H or —OCH$_2$Ph and R$^2$ is H or COOCH$_3$. Further preferred embodiments of the compounds corresponding to Structure 194 are set out in Table 194.

STRUCTURE 194:

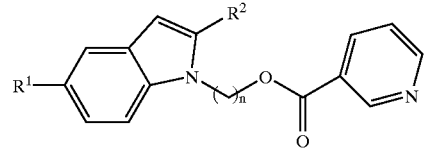

TABLE 194

COMPOUNDS 943–954 CORRESPONDING TO STRUCTURE 194

| | | n = | | | |
|---|---|---|---|---|---|
| $R^1$ | $R^2$ | 6 | 7 | 8 | 9 |
| H | H | 943 | 944 | 945 | 946 |
| H | COOCH$_3$ | 947 | 948 | 949 | 950 |
| —OCH$_2$Ph | COOCH$_3$ | 951 | 952 | 953 | 954 |

In further embodiments, the compounds of the present invention preferably correspond to compounds of the Structure 196 wherein n is an integer of from 1 to 12, more preferably, from 3 to 10, more preferably from 5 to 9 and, still more preferably from 6 to 9 and wherein $R^1$ is an H or a —OCH$_2$Ph and $R^2$ is H or COOCH$_3$. Further preferred embodiments of the compounds corresponding to Structure 196 are set out in Table 196.

STRUCTURE 196:

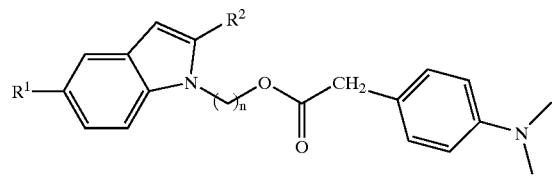

TABLE 196

COMPOUNDS 955–966 CORRESPONDING TO STRUCTURE 196

| | | n = | | | |
|---|---|---|---|---|---|
| $R^1$ | $R^2$ | 6 | 7 | 8 | 9 |
| H | H | 955 | 956 | 957 | 958 |
| H | COOCH$_3$ | 959 | 960 | 961 | 962 |
| —OCH$_2$Ph | COOCH$_3$ | 963 | 964 | 965 | 966 |

In further embodiments, the compounds of the present invention preferably correspond to compounds of the Structure 198 wherein n is an integer of from 1 to 12, more preferably, from 3 to 10, more preferably from 5 to 9 and, still more preferably from 6 to 9 and wherein $R^1$ is an H, —OCHPh or —OCPh$_3$ and $R^2$ is H, or COOCH$_3$. Further preferred embodiments of the compounds corresponding to Structure 198 are set out in Table 198.

STRUCTURE 198:

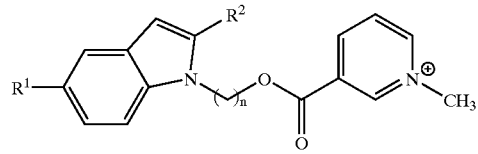

TABLE 198

COMPOUNDS 967–978 CORRESPONDING TO STRUCTURE 198

| | | n = | | | |
|---|---|---|---|---|---|
| $R^1$ | $R^2$ | 6 | 7 | 8 | 9 |
| H | H | 967 | 968 | 969 | 970 |
| H | COOCH$_3$ | 971 | 972 | 973 | 974 |
| —OCH$_2$Ph | COOCH$_3$ | 975 | 976 | 977 | 978 |
| —OCPh$_3$ | COOCH$_3$ | | | 1106 | |

In further embodiments, the compounds of the present invention preferably correspond to compounds of the Structure 200 wherein n is an integer of from 1 to 12, more preferably, from 3 to 10, more preferably from 5 to 9 and, still more preferably from 6 to 9 and wherein $R^1$ is H or a —OCH$_7$Ph and $R^2$ is H or COOCH$_3$. Further preferred embodiments of the compounds corresponding to Structure 200 are set out in Table 200.

STRUCTURE 200:

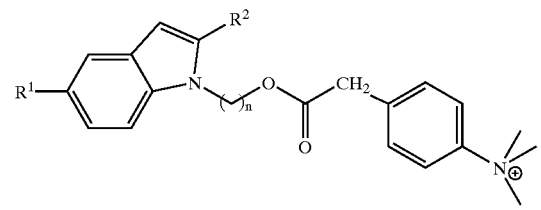

TABLE 200

COMPOUNDS 979–990 CORRESPONDING TO STRUCTURE 200

| | | n = | | | |
|---|---|---|---|---|---|
| $R^1$ | $R^2$ | 6 | 7 | 8 | 9 |
| H | H | 979 | 980 | 981 | 982 |
| H | COOCH$_3$ | 983 | 984 | 985 | 986 |
| OCH$_2$Ph | COOCH$_3$ | 987 | 988 | 989 | 990 |

In further embodiments, the compounds of the present invention preferably correspond to compounds of the Structure 202A.

STRUCTURE 202A:

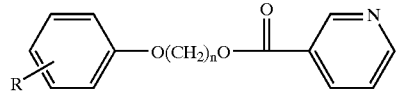

In further embodiments, the compounds of the present invention preferably correspond to compounds of the Structure 202A wherein n is an integer of from 1 to 12, more preferably, from 3 to 10, more preferably from 5 to 9 and, still more preferably from 6 to 9 and wherein R is H; 4-NO$_2$; 2-CONHPh; 2-NO$_2$; 4-[1'(4'-acetylpiperazine)]; 2-COCH$_3$; 3-OCOCH$_3$; 3-OCH$_3$; 4-COCH$_3$; 3-OCOPh; 2-CONH$_2$; 4-CH=CHCOCH$_3$; 4-OCOPh; 4-CH=CHCOPh; 4-{CO-3'[2'-butylbenzo(b)furan]}; 3-NO$_2$; 4-[5'(5'-phenylhydantoin)]; 2-CH=CHCOPh; 2-OCH$_3$; 4-COPh; 4-CONH$_2$; 3-COCH$_3$; 4-OPh; 4-(N-Phthalimide); 3-(N-Morpholine); 2-(N-pyrrolidie); 2-(N-Morpholine); or 4-OCH$_2$Ph. Further preferred embodiments of the compounds corresponding to Structure 202 are set out in Table 202.

TABLE 202

COMPOUNDS 991–1021 CORRESPONDING TO STRUCTURE 202A

| R = | n = 4 | n = 7 | n = 8 |
|---|---|---|---|
| H | 991 | 993 | |
| 4-NO$_2$ | 992 | 994 | 995 |
| 2-CONHPh | | | 996 |
| 2-NO$_2$ | | | 997 |
| 4-[1'(4'-acetylpiperazine)] | | | 998 |
| 2-COCH$_3$ | | | 999 |
| 3-OCOCH$_3$ | | | 1000 |
| 3-OCH$_3$ | | | 1001 |
| 4-COCH$_3$ | | | 1002 |
| 3-OCOPh | | | 1003 |
| 2-CONH$_2$ | | | 1004 |
| 4-CH=CHCOCH$_3$ | | | 1005 |
| 4-OCOPh | | | 1006 |
| 4-CH=CHCOPh | | | 1007 |
| 4-{CO-3'[2'-butylbenzo(b)furan]} | | | 1008 |
| 3-NO$_2$ | | | 1009 |
| 4-[5'-(5'-phenylhydantoin)] | | | 1010 |
| 2-CH=CHCOPh | | | 1011 |
| 2-OCH$_3$ | | | 1012 |
| 4-COPh | | | 1013 |
| 4-CONH$_2$ | | | 1014 |
| 3-COCH$_3$ | | | 1015 |
| 4-OPh | | | 1016 |
| 4-(N-phthalimide) | | | 1017 |
| 3-(N-morpholine) | | | 1018 |
| 2-(N-pyrrolidine) | | | 1019 |
| 2-(N-morpholine) | | | 1020 |
| 4-OCH$_2$Ph | | | 1021 |

In further embodiments, the compounds of the present invention preferably correspond to compounds of the Structure 204A wherein n is an integer of from 1 to 12, more preferably, from 3 to 10, more preferably from 5 to 9 and, still more preferably, from 6 to 9 and wherein R is 4-NO$_2$; 2-CONHPh; 2-NO$_2$; 4-[1'(4'-acetylpiperazine)]; 2-COCH$_3$; 3-OCOCH$_3$; 3-OCH$_3$; 4-COCH$_3$; 3-OCOPh; 2-CONH$_2$; 4-CH=CHCOCH$_3$; 4-OCOPh; 4-CH=CHCOPh; 4-{CO-3'[2'-butylbenzo(b)furan]}; 3-NO$_2$; 4-[5'-(5'-phenylhydantoin)]; 4-CH=CHCOPh; 2-OCH$_3$; 4-COPh; 4-CONH$_2$; 3-COCH$_3$; 4OPh; 4-(N-phthalimide); 3-(N-morpholine); 2-(N-pyrrolidine); 2-(N-morpholine); or 4-OCH$_2$Ph. Further preferred embodiments of the compounds corresponding to Structure 204 are set out in Table 204.

STRUCTURE 204A:

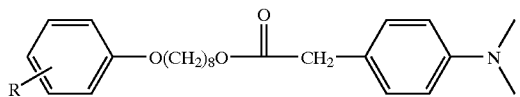

TABLE 204

COMPOUNDS 1022–1048 CORRESPONDING TO STRUCTURE 204A

| R = | |
|---|---|
| 4-NO$_2$ | 1022 |
| 2-CONHPh | 1023 |
| 2-NO$_2$ | 1024 |

TABLE 204-continued

COMPOUNDS 1022–1048 CORRESPONDING TO STRUCTURE 204A

| R = | |
|---|---|
| 4-[1'(4'-acetylpiperazine)] | 1025 |
| 2-COCH$_3$ | 1026 |
| 3-OCOCH$_3$ | 1027 |
| 3-OCH$_3$ | 1028 |
| 4-COCH$_3$ | 1029 |
| 3-OCOPh | 1030 |
| 2-CONH$_2$ | 1031 |
| 4-CH=CHCOCH$_3$ | 1032 |
| 4-OCOPh | 1033 |
| 4-CH=CHCOPh | 1034 |
| 4-{CO-3'[2'-butylbenzo(b)furan]} | 1035 |
| 3-NO$_2$ | 1036 |
| 4-[5'-(5'-phenylhydantoin)] | 1037 |
| 2-CH=CHCOPh | 1038 |
| 2-OCH$_3$ | 1039 |
| 4-COPh | 1040 |
| 4-CONH$_2$ | 1041 |
| 3-COCH$_3$ | 1042 |
| 4-OPh | 1043 |
| 4-(N-phthalimide) | 1044 |
| 3-(N-morpholine) | 1045 |
| 2-(N-pyrrolidine) | 1046 |
| 2-(N-morpholine) | 1047 |
| 4-OCH$_2$Ph | 1048 |

In further embodiments, the compounds of the present invention preferably correspond to compounds of the Structure 206 wherein n is an integer of from 1 to 12, more preferably, from 3 to 10, more preferably from 5 to 9 and, still more preferably, from 6 to 9 and wherein R is H; 4-NO$_2$; 2-CONHPh; 2-NO$_2$; 2-COCH$_3$; 3-OCH$_3$; 4-COCH$_3$; 3-OCOPh; 2-CONH$_2$; 4-CH=CHCOCH$_3$; 4-OCOPh; 4-CH=CHCOPh; 4-{CO-3'[2'-butylbenzo(b)furan]}; 3-NO$_2$; 2-CH=CHCOPh; 2-OCH$_3$; 4-COPh; 3-COCH$_3$; 4-OPh; 4-(N-phthalimide); or 4-OCH$_2$Ph. Further preferred embodiments of the compounds corresponding to Structure 206 are set out in Table 206.

STRUCTURE 206:

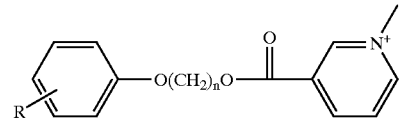

TABLE 206

COMPOUNDS 1049–1068 CORRESPONDING TO STRUCTURE 206

| R = | n = 4 | n = 7 | n = 8 |
|---|---|---|---|
| H | 1049 | 1051 | |
| 4-NO$_2$ | 1050 | 1052 | 1053 |
| 2-CONHPh | | | 3054 |
| 2-NO$_2$ | | | 1055 |
| 2-COCH$_3$ | | | 1056 |
| 3-OCH$_3$ | | | 1057 |
| 4-COCH$_3$ | | | 1058 |
| 3-OCOPh | | | 1059 |
| 2-CONH$_2$ | | | 1060 |
| 4-CH=CHCOCH$_3$ | | | 1061 |
| 4-OCOPh | | | 1062 |
| 4-CH=CHCOPh | | | 1063 |
| 4-{CO-3'[2'-butylbenzo(b)furan]} | | | 1064 |
| 3-NO$_2$ | | | 1065 |

TABLE 206-continued

COMPOUNDS 1049–1068 CORRESPONDING TO STRUCTURE 206

| R = | n = 4 | n = 7 | n = 8 |
|---|---|---|---|
| 2-CH=CHCOPh | | | 1066 |
| 2-OCH$_3$ | | | 1067 |
| 4-COPh | | | 1068 |
| 3-COCH$_3$ | | | 1069 |
| 4-OPh | | | 1070 |
| 4-(N-phthalimide) | | | 1071 |
| 4-OCH$_2$Ph | | | 1072 |

In further embodiments, the compounds of the present invention preferably correspond to compounds of the Structure 208 wherein, n is an integer of from 1 to 12, more preferably, from 3 to 10, more preferably from 5 to 9 and, still more preferably, from 6 to 9 and wherein R is 4-NO$_2$; 2-CONHPh; 2-NO$_2$; 2-COCH$_3$; 3-OCH$_3$; 4-OCOPh; 2-CONH$_2$; 4-CH=CHCOCH$_3$; 4-OCOPh; 4-CH=CHCOPh; 4-{CO-3'[2'-butylbenzo(b)furan]}; 3-NO$_2$; 2-CH=CHCOPh; 2-OCH$_3$; 4-COPh; 3-COCH$_3$; 4-OPh; 4-(N-phthalimide); 3(N-morpholine); 2-(N-morpholine); or 4-OCH$_2$Ph. Further preferred embodiments of the compounds corresponding to Structure 208 are set out in Table 208.

STRUCTURE 208:

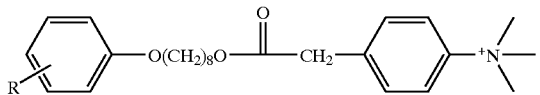

TABLE 208

COMPOUNDS 1073–1094 CORRESPONDING TO STRUCTURE 208

| R = | |
|---|---|
| 4-NO$_2$ | 1073 |
| 2-CONHPh | 1074 |
| 2-NO$_2$ | 1075 |
| 2-COCH$_3$ | 1076 |
| 3-OCH$_3$ | 1077 |
| 4-COCH$_3$ | 1078 |
| 3-OCOPh | 1079 |
| 2-CONH$_2$ | 1080 |
| 4-CH=CHCOCH$_3$ | 1081 |
| 4-OCOPh | 1082 |
| 4-CH=CHCOPh | 1083 |
| 4-{CO-3'[2'-butylbenzo(b)furan]} | 1084 |
| 3-NO$_2$ | 1085 |
| 2-CH=CHCOPh | 1086 |
| 2-OCH$_3$ | 1087 |
| 4-COPh | 1088 |
| 3-COCH$_3$ | 1089 |
| 4-OPh | 1090 |
| 4-(N-phthalimide) | 1091 |
| 3-(N-morpholine) | 1092 |
| 2-(N-morpholine) | 1093 |
| 4-OCH$_2$Ph | 1094 |

In further embodiments, the compounds of the present invention preferably correspond to compounds of the Structure 210 wherein R is NH$_2$; NMe2; NMe$_3$.I; NH$_2$.HCl; NME$_2$.HCl. Further preferred embodiments of the compounds corresponding to Structure 210 are set out in Table 210.

STRUCTURE 210:

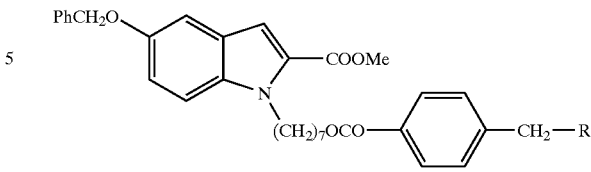

TABLE 210

COMPOUNDS 1095–1099 CORRESPONDING TO STRUCTURE 210

| R = | |
|---|---|
| NH$_2$ | 1095 |
| NMe$_2$. | 1096 |
| NMe$_3$.I— | 1097 |
| NH$_2$.HCl | 1098 |
| NMe$_2$.HCl | 1099 |

In further embodiments, the compounds of the present invention preferably correspond to compounds of the Structure 212 wherein R$^1$ is PhCONH or Ph$_3$C and R" is H or COOCH$_3$. Further preferred embodiments of the compounds corresponding to Structure 212 are set out in Table 212.

STRUCTURE 212:

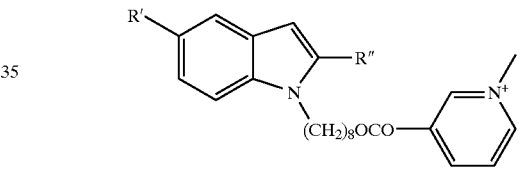

TABLE 212

COMPOUNDS 1100–1101 CORRESPONDING TO STRUCTURE 212

| R' = | R" = | |
|---|---|---|
| PhCONH | H | 1100 |
| Ph$_3$C | COOCH$_3$ | 1101 |

In further embodiments, the compounds of the present invention preferably correspond to compounds of the Structure 214 wherein R is 4-hydroxyphenyl or 3-hydroxy-4-methylphenyl. Further preferred embodiments of the compounds corresponding to Structure 214 are set out in Table 214.

STRUCTURE 214:

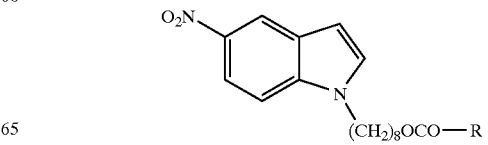

TABLE 214

COMPOUNDS 1102–1103 CORRESPONDING TO STRUCTURE 214

R =

| | |
|---|---|
| 4-hydroxyphenyl | 1102 |
| 3-hydroxy-4-methylphenyl | 1103 |

In further embodiments, the compounds of the present invention preferably correspond to compounds of Structure 216 wherein R' is PhCONH and and R" is H or COOCH$_3$ and n=7 or 8. Further preferred embodiments of the compounds corresponding to Structure 216 are set out in Table 216.

Structure 216:

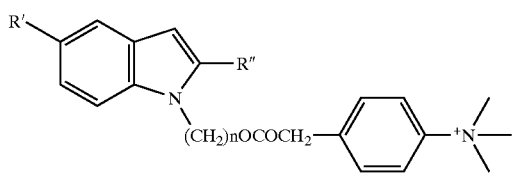

TABLE 216

COMPOUNDS 1104–1105 CORRESPONDING TO STRUCTURE 216

| R' = | R" = | n = | |
|---|---|---|---|
| PhCONH | H | 8 | 1104 |
| PhCH$_2$O | COOCH$_3$ | 7 | 1105 |

In a particularly preferred embodiment of the invention herein, the present invention comprises compounds of the structures in Table 301 below.

TABLE 301

A FIRST GROUPING OF BACTERIAL NAD SYNTHETASE INHIBITOR LEAD COMPOUNDS

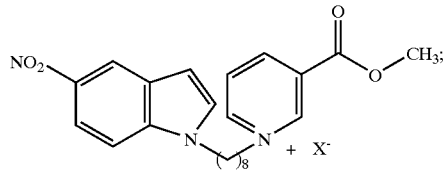

13

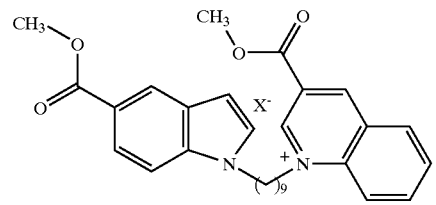

174

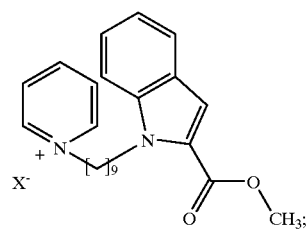

182

TABLE 301-continued
A FIRST GROUPING OF BACTERIAL NAD SYNTHETASE
INHIBITOR LEAD COMPOUNDS
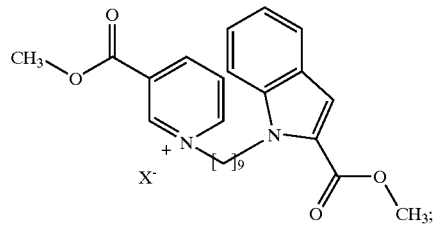
190
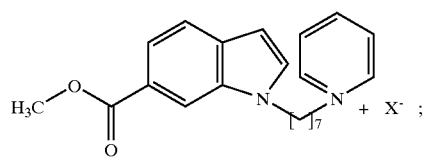
213
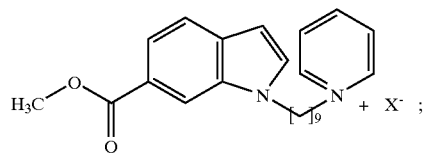
214
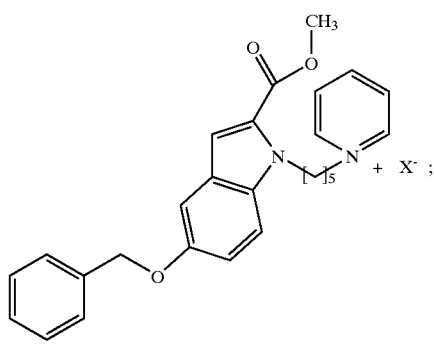
228
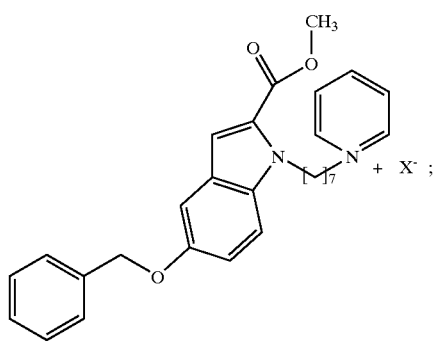
229

TABLE 301-continued
A FIRST GROUPING OF BACTERIAL NAD SYNTHETASE INHIBITOR LEAD COMPOUNDS
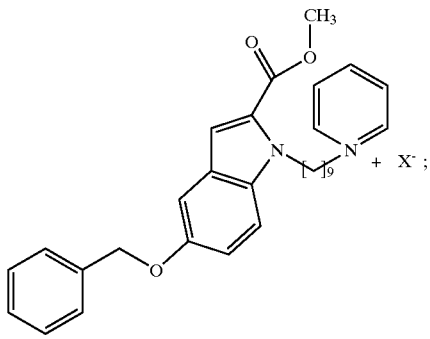
229
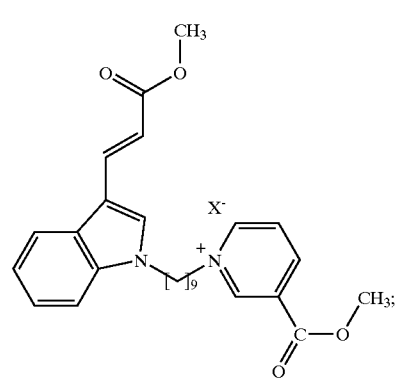
270
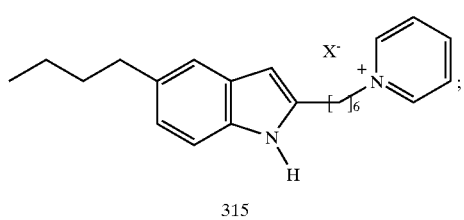
315
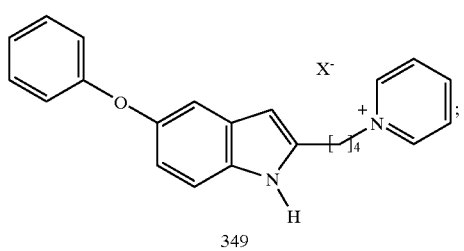
349
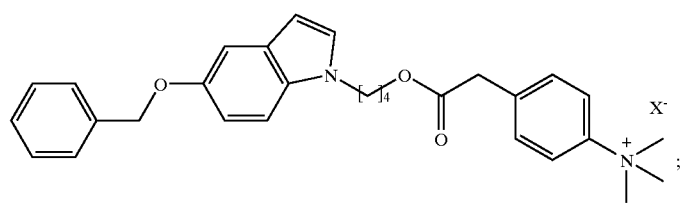
745

TABLE 301-continued
A FIRST GROUPING OF BACTERIAL NAD SYNTHETASE
INHIBITOR LEAD COMPOUNDS
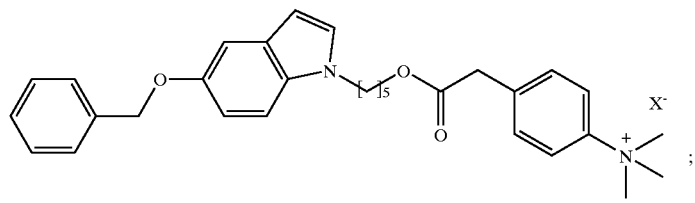
746
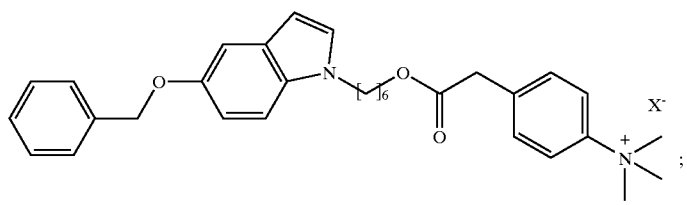
747
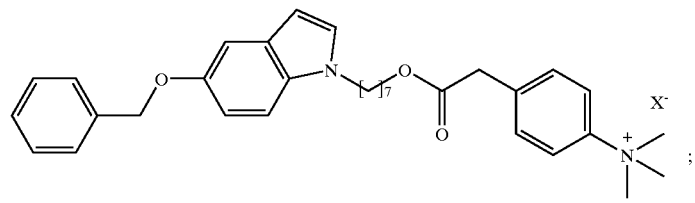
748
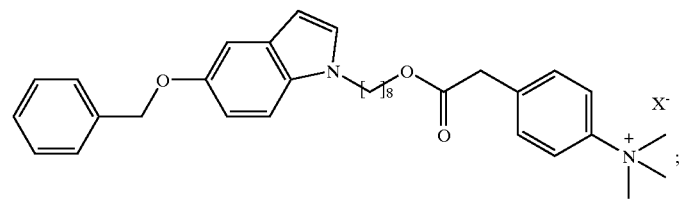
749
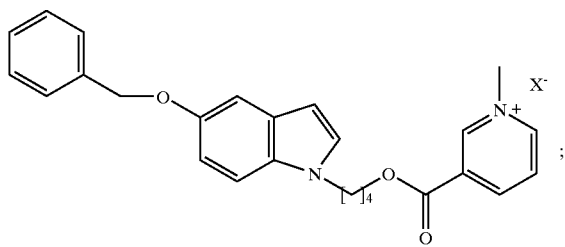
765
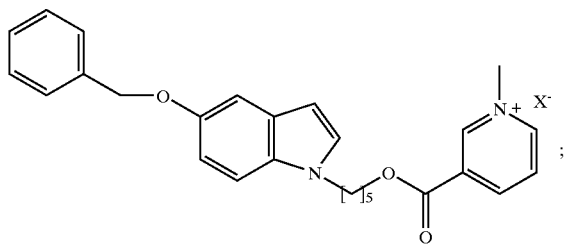
766

TABLE 301-continued
A FIRST GROUPING OF BACTERIAL NAD SYNTHETASE
INHIBITOR LEAD COMPOUNDS
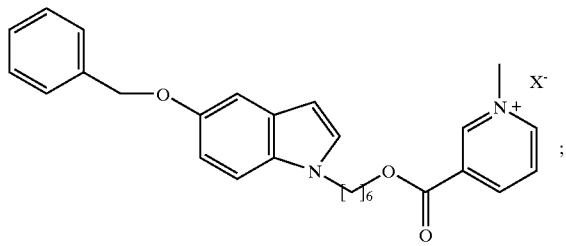
767
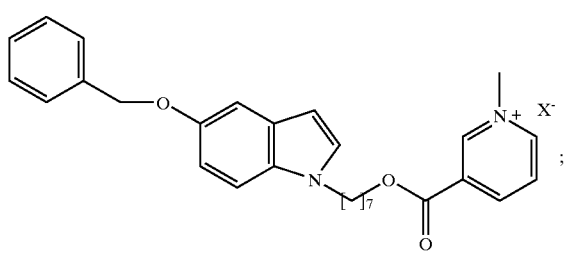
768
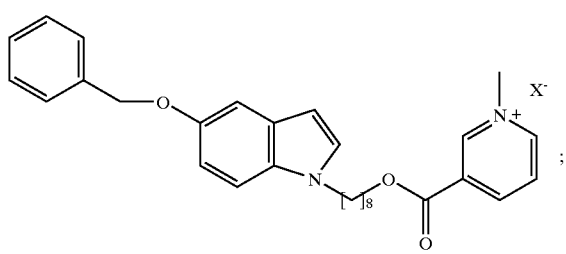
769
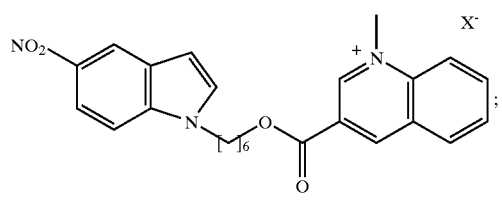
832
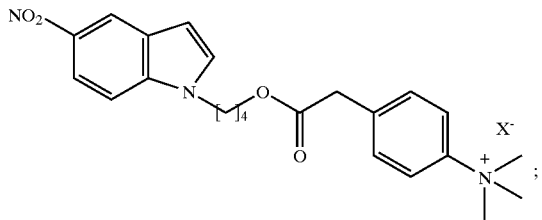
848

TABLE 301-continued
A FIRST GROUPING OF BACTERIAL NAD SYNTHETASE
INHIBITOR LEAD COMPOUNDS
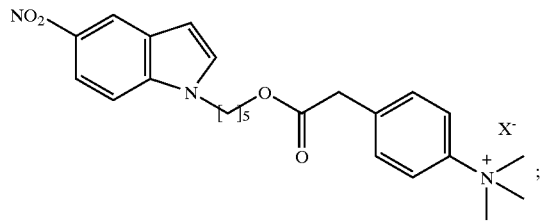
849
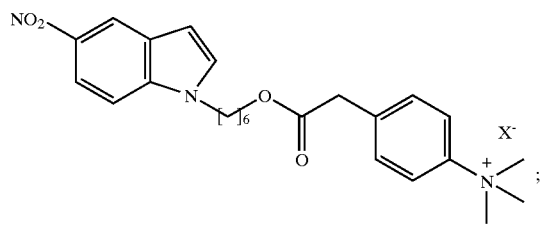
850
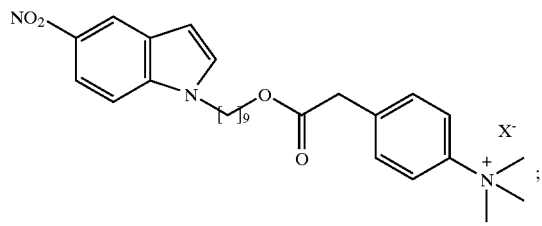
853
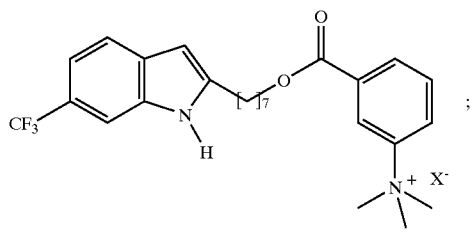
869
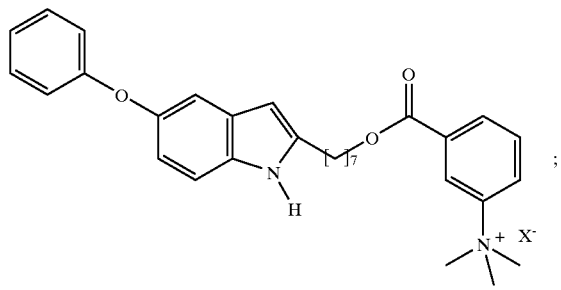
872

TABLE 301-continued
A FIRST GROUPING OF BACTERIAL NAD SYNTHETASE
INHIBITOR LEAD COMPOUNDS
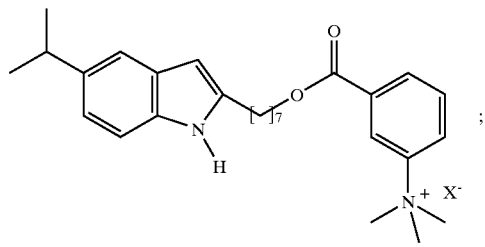
875
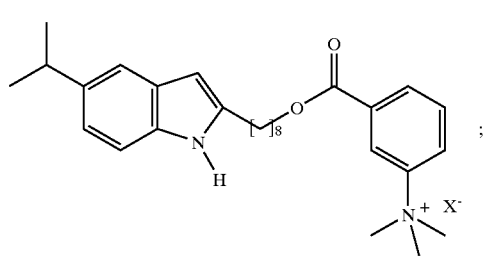
876
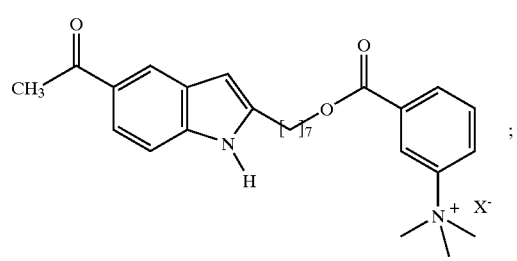
878
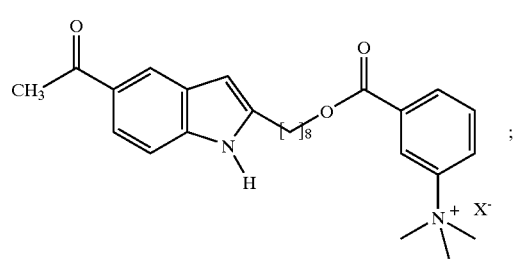
879
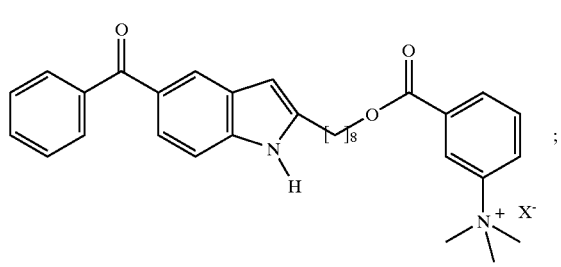
882

TABLE 301-continued
A FIRST GROUPING OF BACTERIAL NAD SYNTHETASE
INHIBITOR LEAD COMPOUNDS
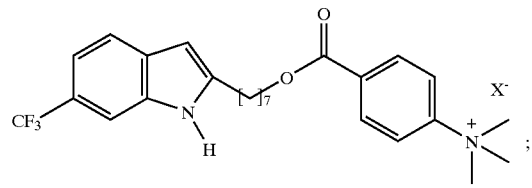
884
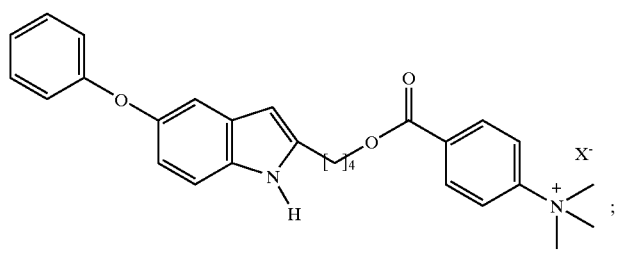
886
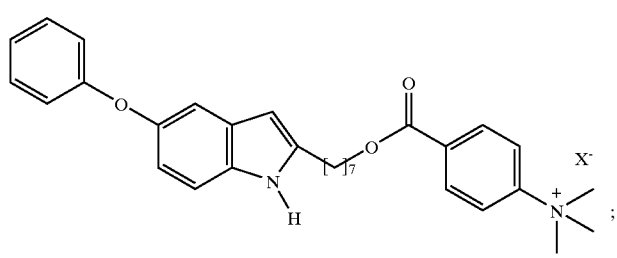
887
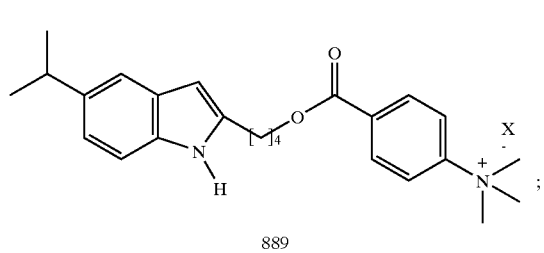
889
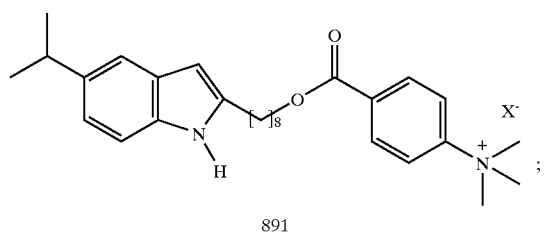
891
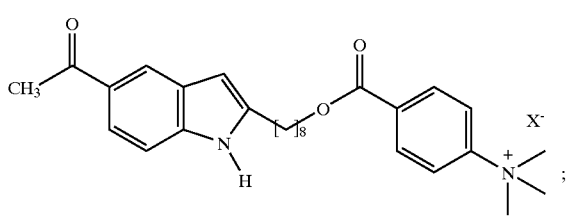
894

TABLE 301-continued
A FIRST GROUPING OF BACTERIAL NAD SYNTHETASE
INHIBITOR LEAD COMPOUNDS
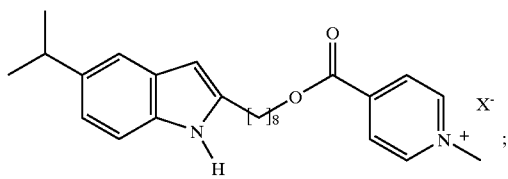
906
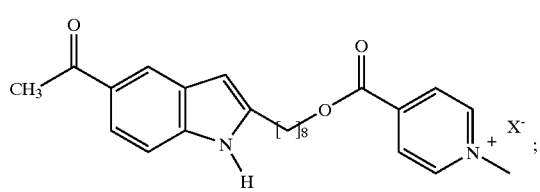
909
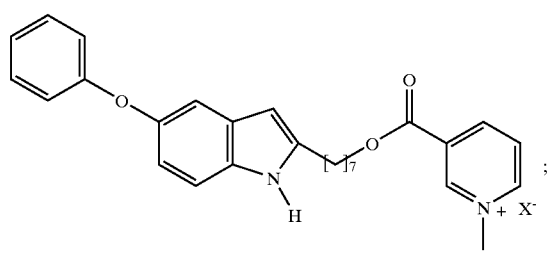
917
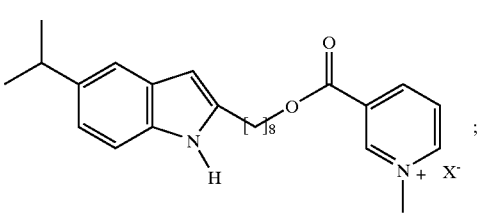
921
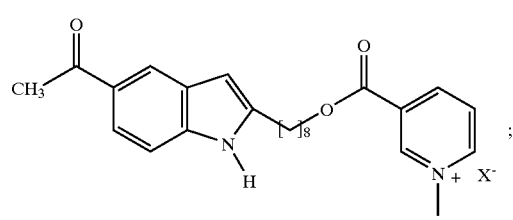
924
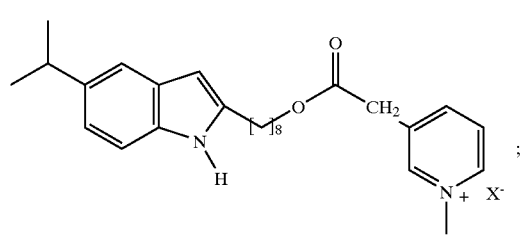
936

TABLE 301-continued
A FIRST GROUPING OF BACTERIAL NAD SYNTHETASE
INHIBITOR LEAD COMPOUNDS
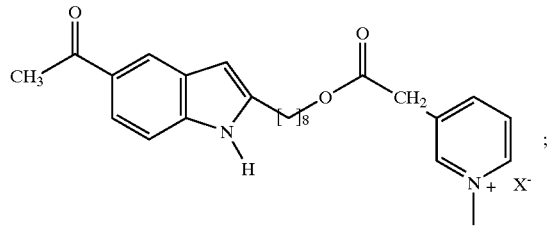
939
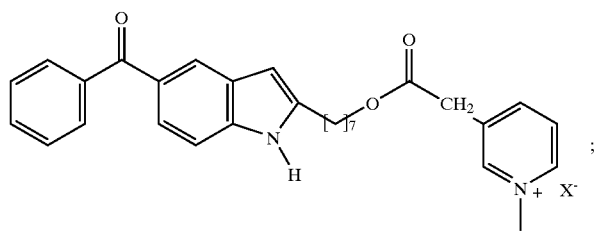
941
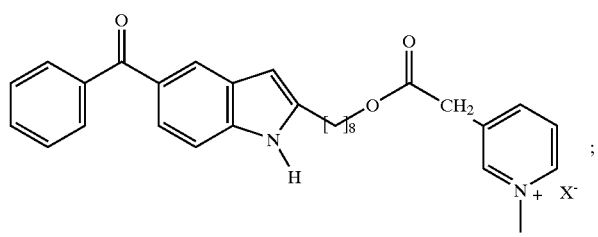
942
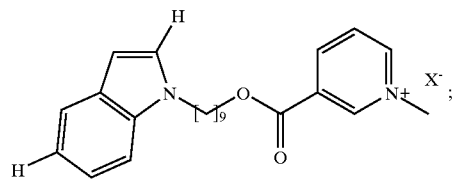
970
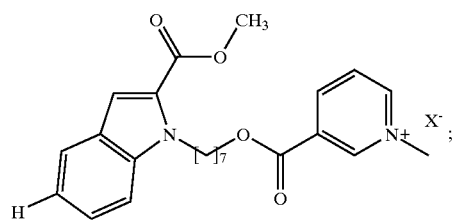
972

TABLE 301-continued
A FIRST GROUPING OF BACTERIAL NAD SYNTHETASE
INHIBITOR LEAD COMPOUNDS
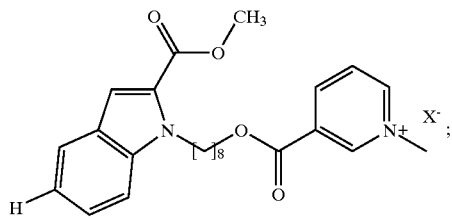
973
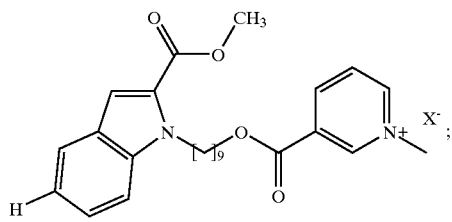
974
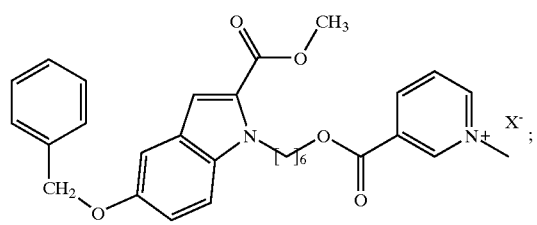
975
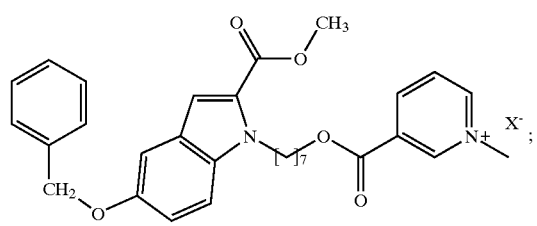
976
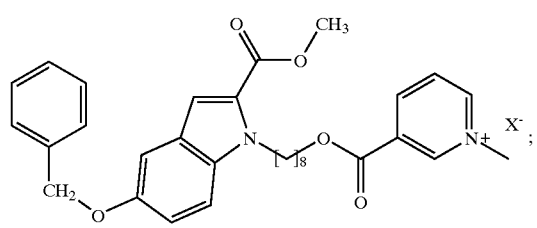
977

TABLE 301-continued
A FIRST GROUPING OF BACTERIAL NAD SYNTHETASE
INHIBITOR LEAD COMPOUNDS
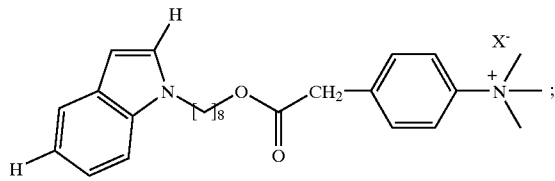
981
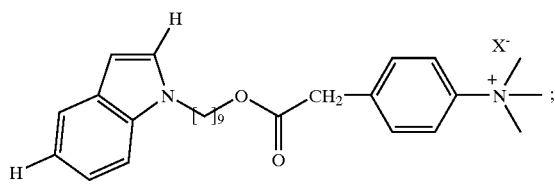
982
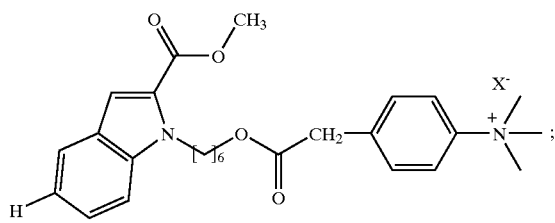
983
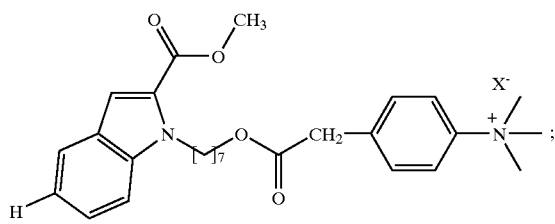
984
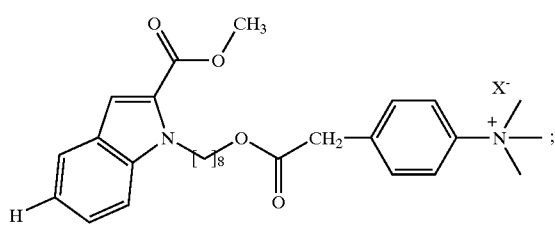
985

TABLE 301-continued
A FIRST GROUPING OF BACTERIAL NAD SYNTHETASE
INHIBITOR LEAD COMPOUNDS
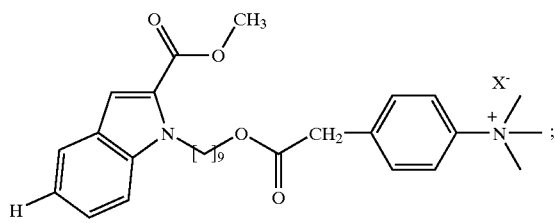
986
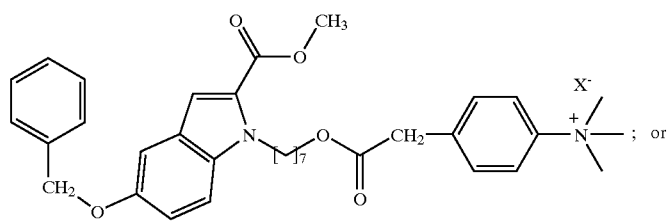
988
or
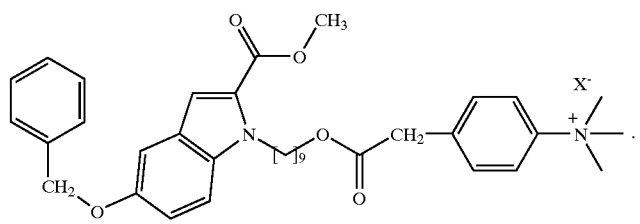
990
In a further preferred embodiment, the present invention comprises one or more compounds from Table 302, below.
TABLE 302
A SECOND GROUPING OF BACTERIAL NAD SYNTHETASE
INHIBITOR LEAD COMPOUNDS
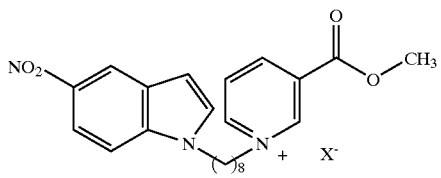
13

TABLE 302-continued
A SECOND GROUPING OF BACTERIAL NAD SYNTHETASE
INHIBITOR LEAD COMPOUNDS
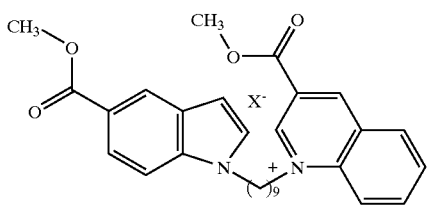
174
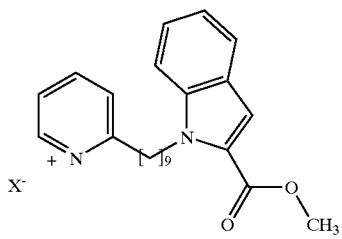
182
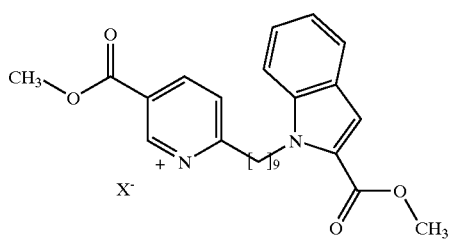
190
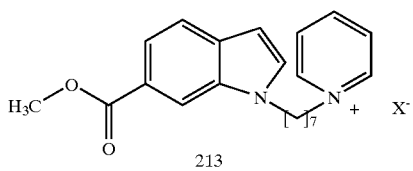
213
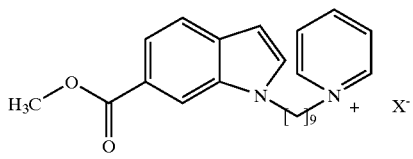
214
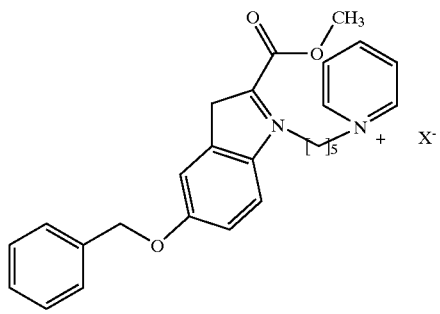
228

TABLE 302-continued
A SECOND GROUPING OF BACTERIAL NAD SYNTHETASE
INHIBITOR LEAD COMPOUNDS
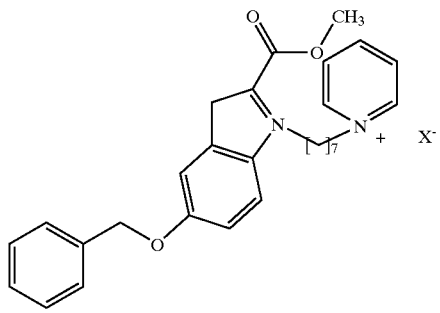
229
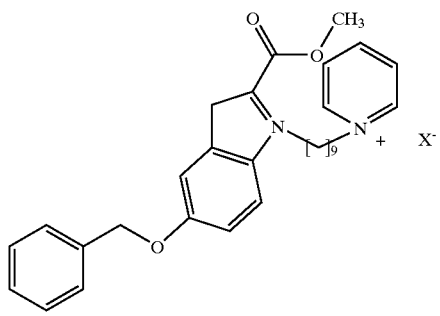
230
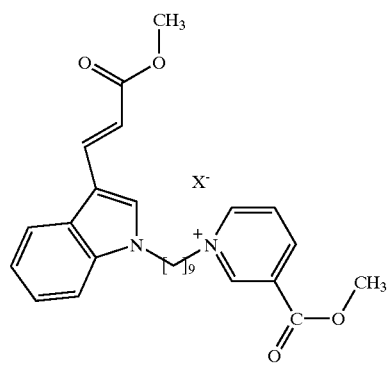
270
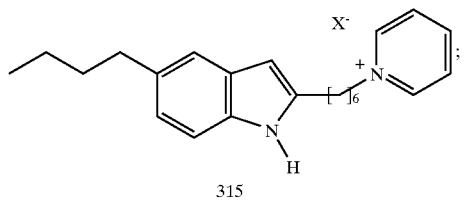
315

TABLE 302-continued
A SECOND GROUPING OF BACTERIAL NAD SYNTHETASE
INHIBITOR LEAD COMPOUNDS
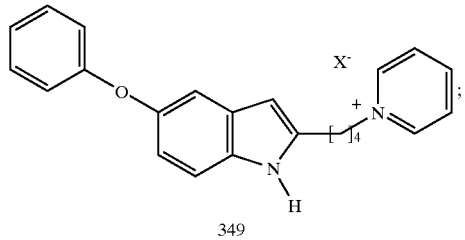
349
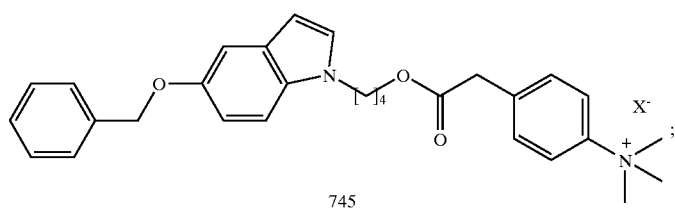
745
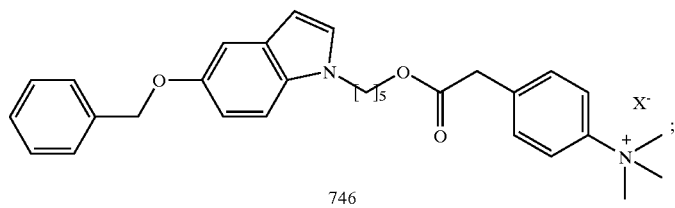
746
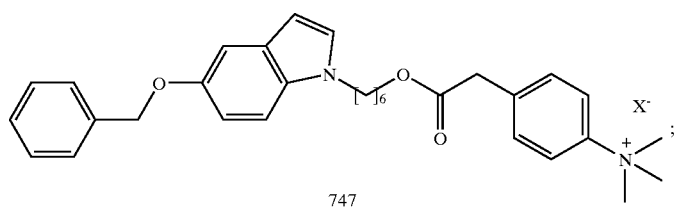
747
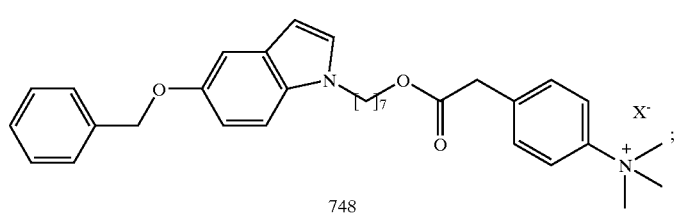
748
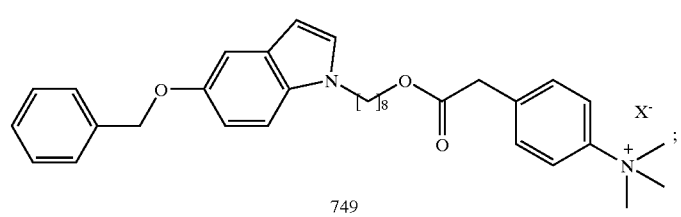
749

TABLE 302-continued
A SECOND GROUPING OF BACTERIAL NAD SYNTHETASE
INHIBITOR LEAD COMPOUNDS
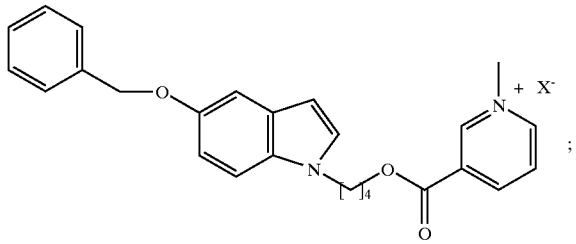
765
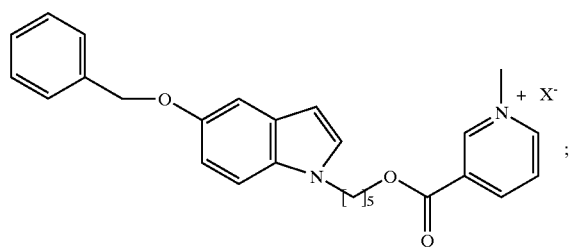
766
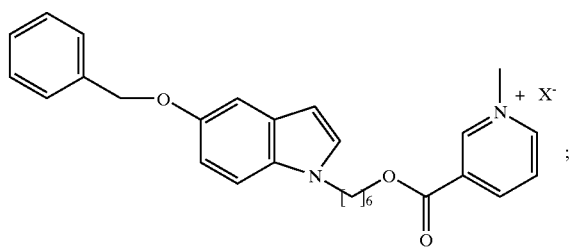
767
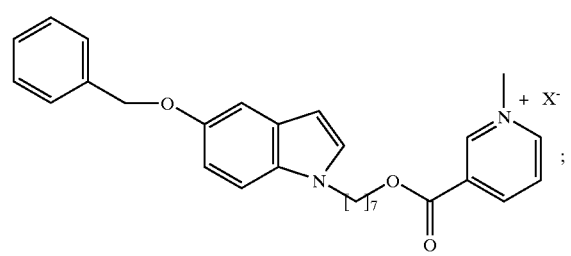
768
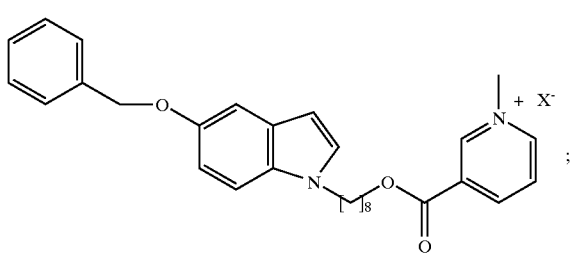
769

TABLE 302-continued
A SECOND GROUPING OF BACTERIAL NAD SYNTHETASE
INHIBITOR LEAD COMPOUNDS
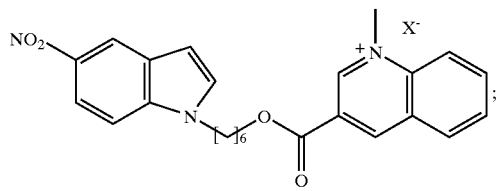
832
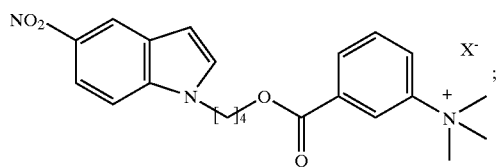
848
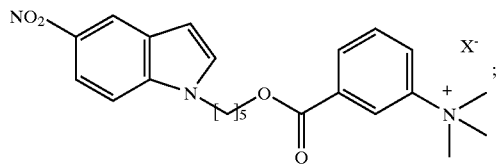
849
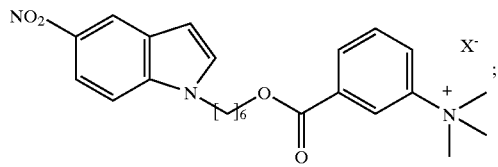
850
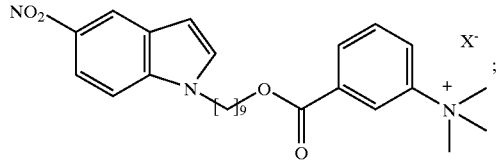
853
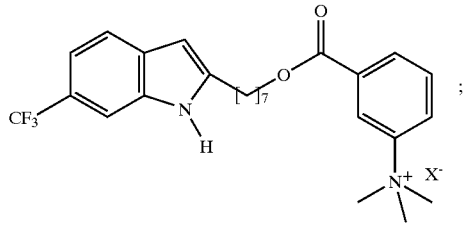
869

TABLE 302-continued
A SECOND GROUPING OF BACTERIAL NAD SYNTHETASE
INHIBITOR LEAD COMPOUNDS
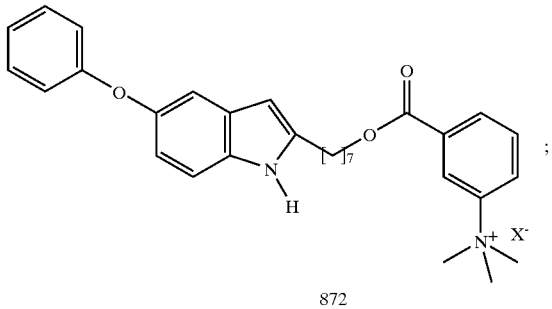
872
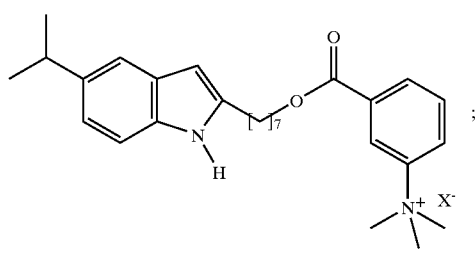
875
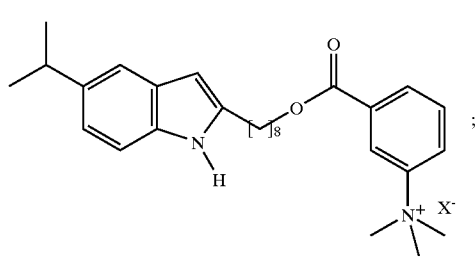
876
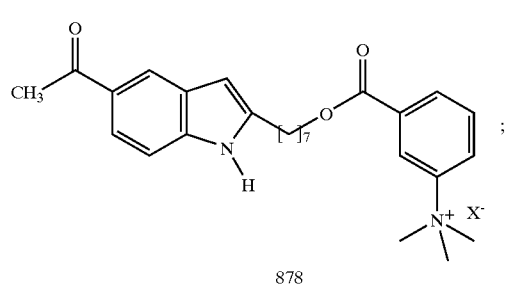
878
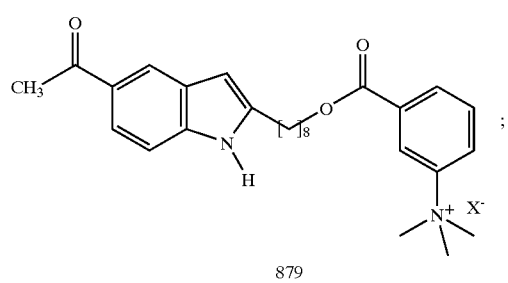
879

TABLE 302-continued
A SECOND GROUPING OF BACTERIAL NAD SYNTHETASE
INHIBITOR LEAD COMPOUNDS
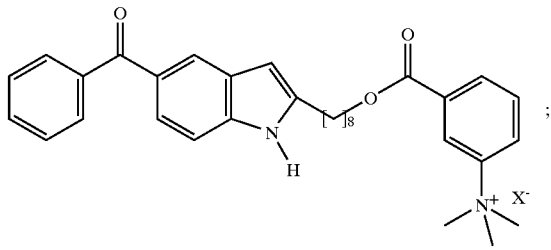
882
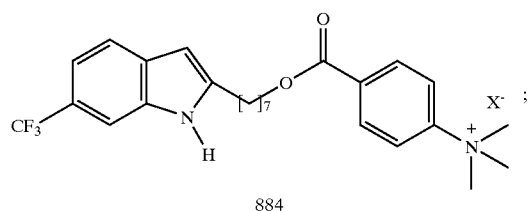
884
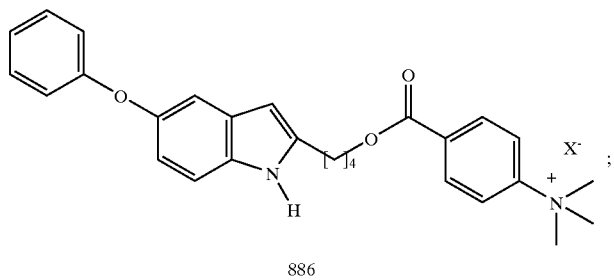
886
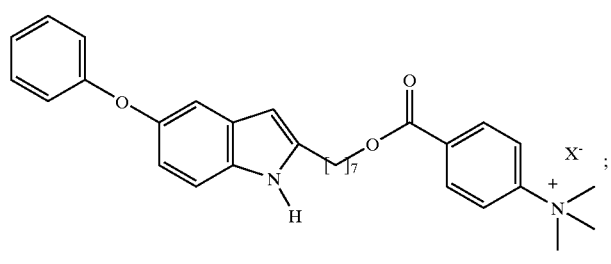
887
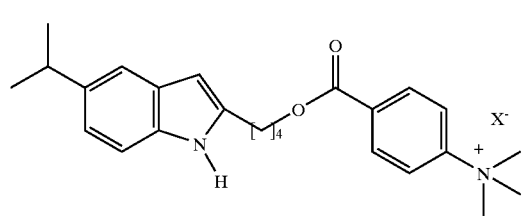
889

TABLE 302-continued
A SECOND GROUPING OF BACTERIAL NAD SYNTHETASE
INHIBITOR LEAD COMPOUNDS
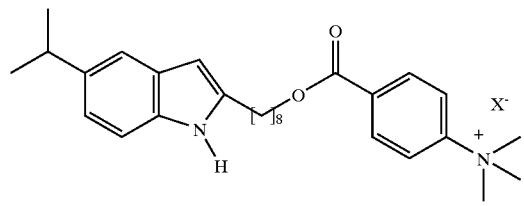
891
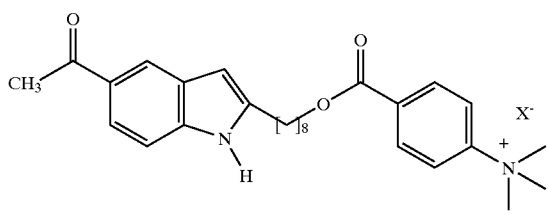
894
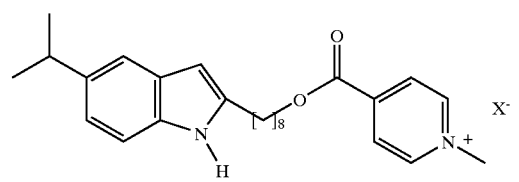
906
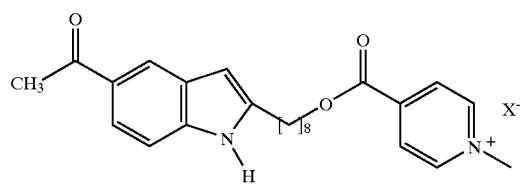
909
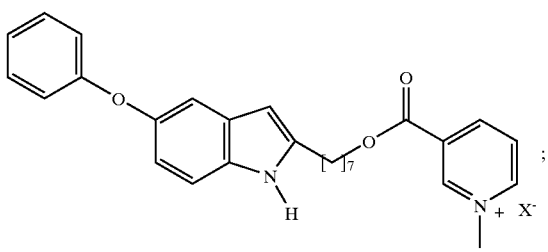
917
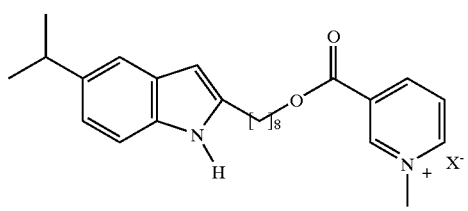
921

TABLE 302-continued
A SECOND GROUPING OF BACTERIAL NAD SYNTHETASE INHIBITOR LEAD COMPOUNDS
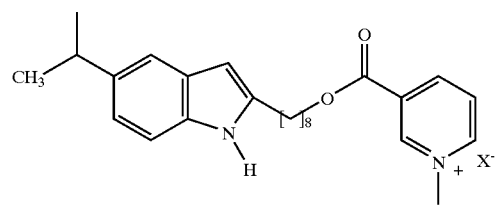
924
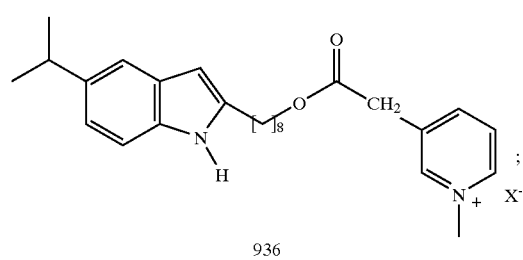
936
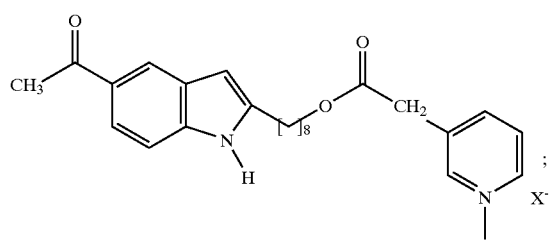
939
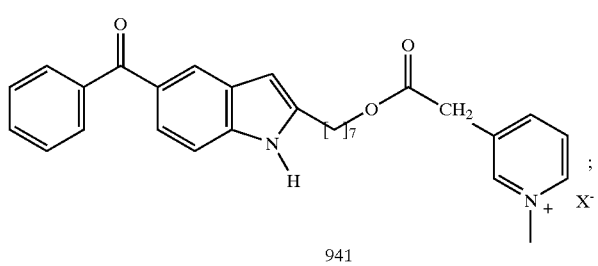
941
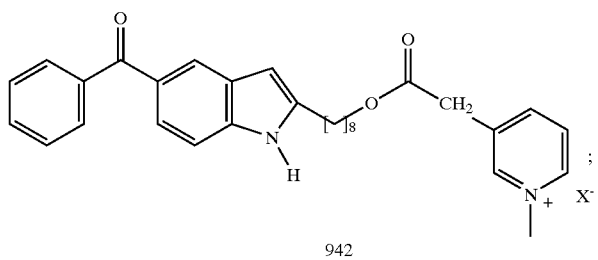
942
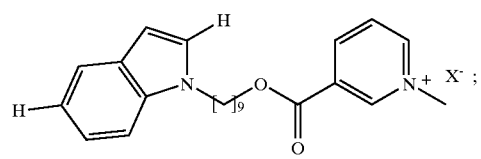
970

TABLE 302-continued
A SECOND GROUPING OF BACTERIAL NAD SYNTHETASE
INHIBITOR LEAD COMPOUNDS
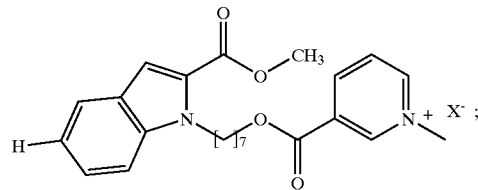
972
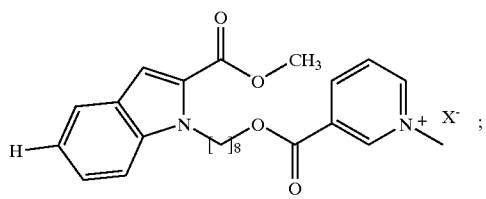
973
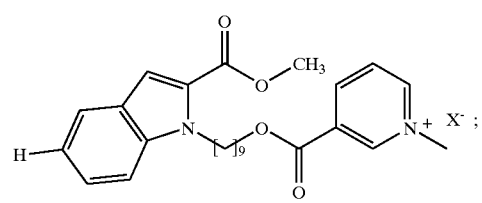
974
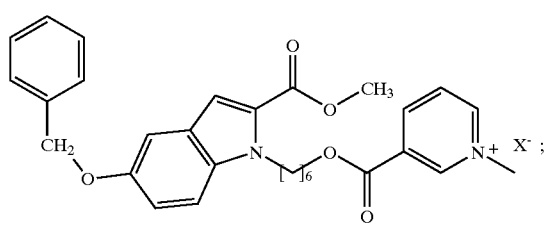
975
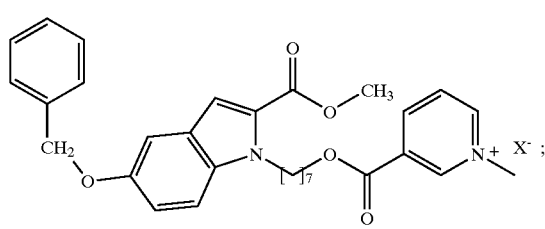
976

TABLE 302-continued
A SECOND GROUPING OF BACTERIAL NAD SYNTHETASE
INHIBITOR LEAD COMPOUNDS
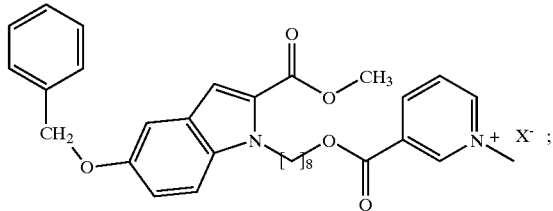
977
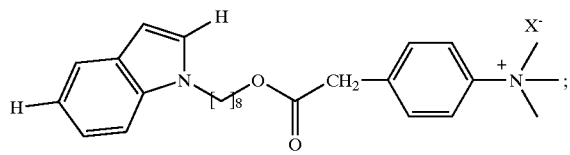
981
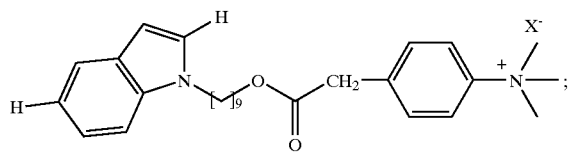
982
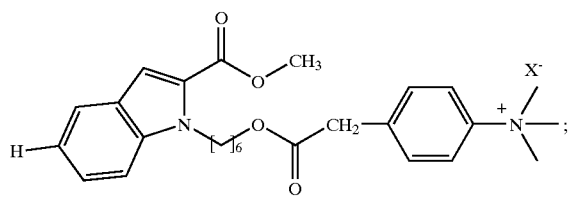
983
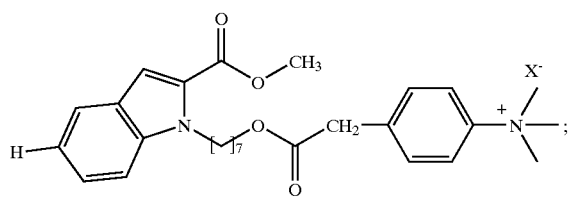
984
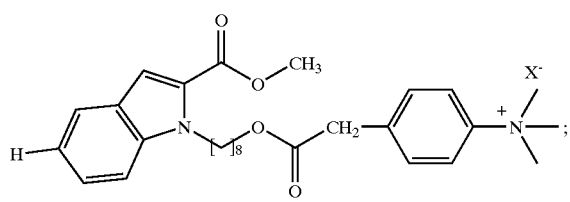
985

TABLE 302-continued
A SECOND GROUPING OF BACTERIAL NAD SYNTHETASE
INHIBITOR LEAD COMPOUNDS
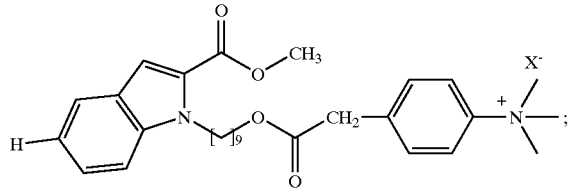
986
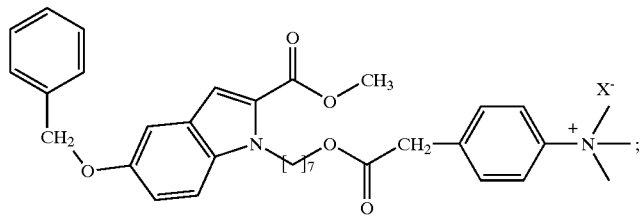
988
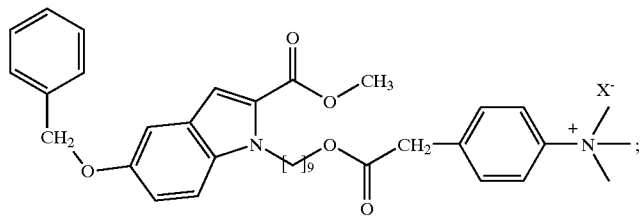
990
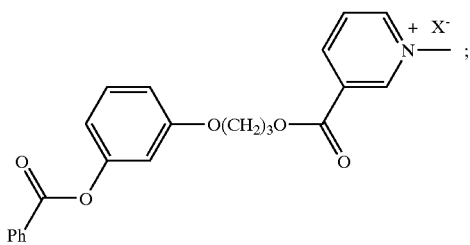
1059
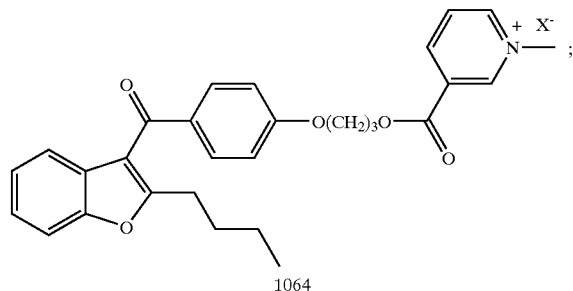
1064

TABLE 302-continued
A SECOND GROUPING OF BACTERIAL NAD SYNTHETASE
INHIBITOR LEAD COMPOUNDS
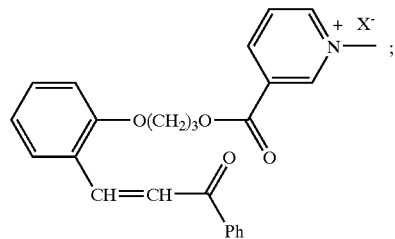
1066
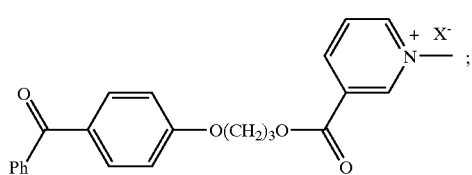
1068
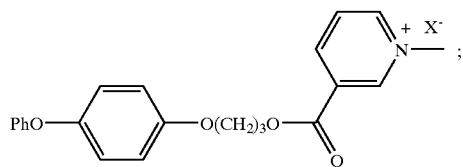
1070
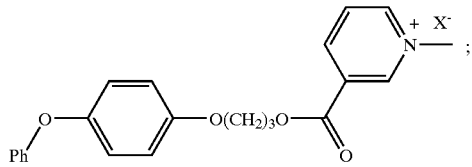
1072
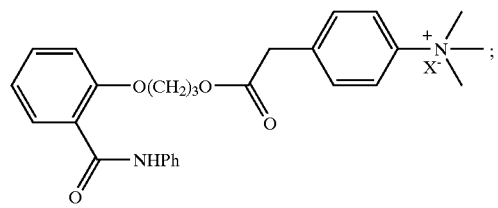
1074
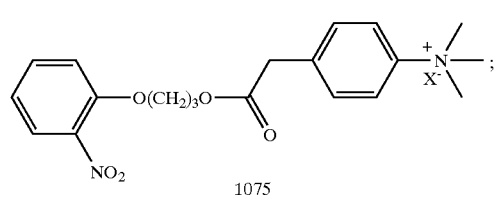
1075

TABLE 302-continued
A SECOND GROUPING OF BACTERIAL NAD SYNTHETASE INHIBITOR LEAD COMPOUNDS
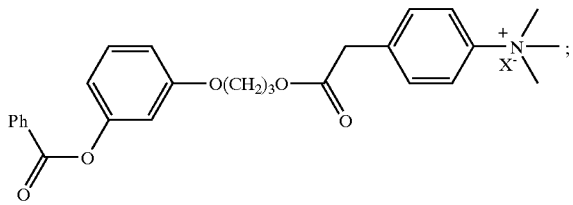
1079
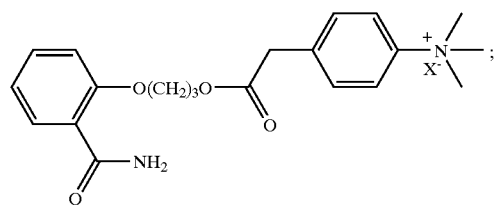
1080
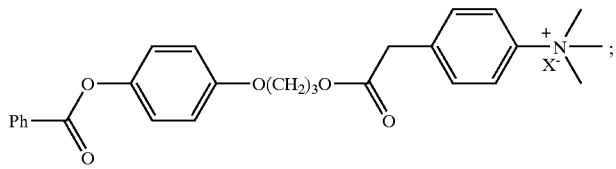
1082
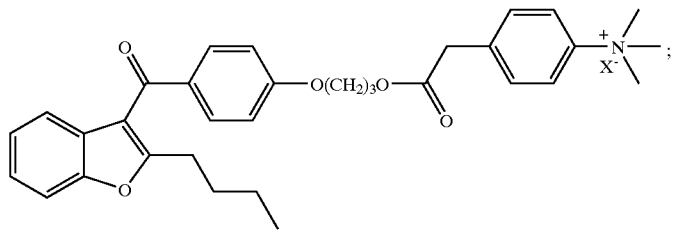
1084
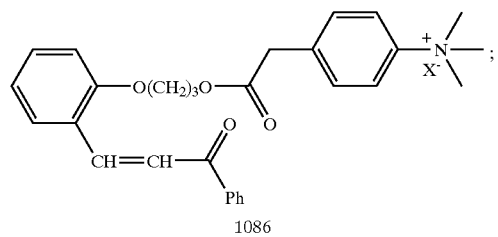
1086
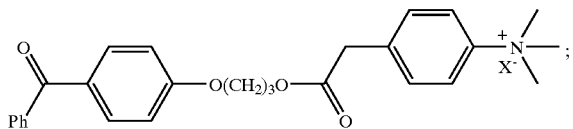
1088

TABLE 302-continued
A SECOND GROUPING OF BACTERIAL NAD SYNTHETASE
INHIBITOR LEAD COMPOUNDS
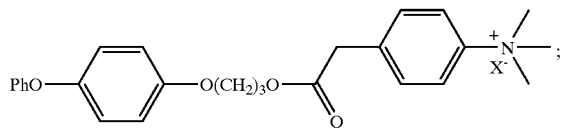
1090
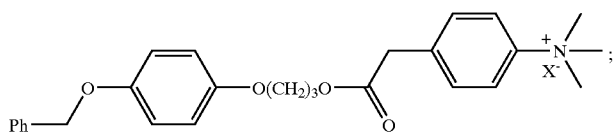
1094
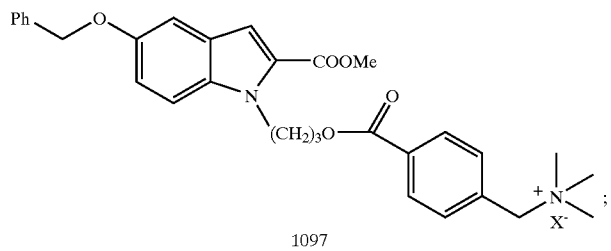
1097
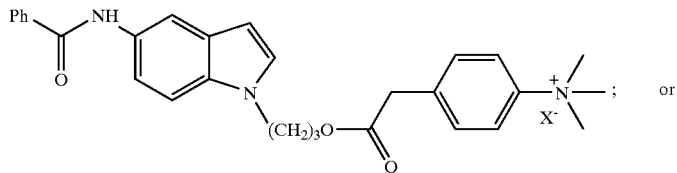
1104
or
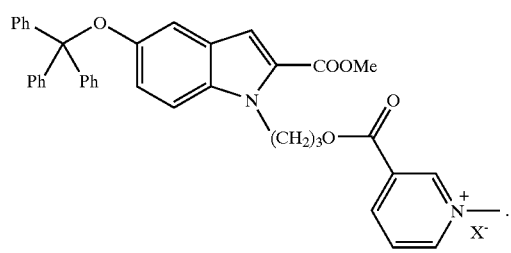
1106

In a further preferred embodiment, the present invention comprises one or more compounds from Table 303, below.
TABLE 303
A THIRD GROUPING OF BACTERIAL NAD SYNTHETASE
INHIBITOR LEAD COMPOUNDS
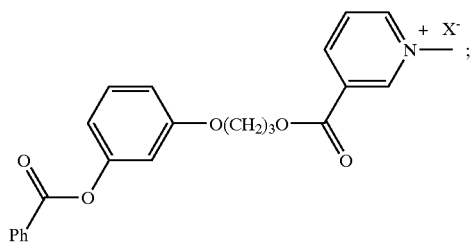
1059
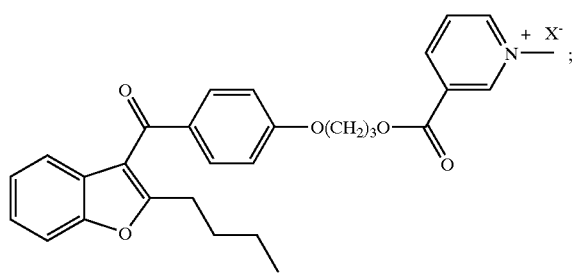
1064
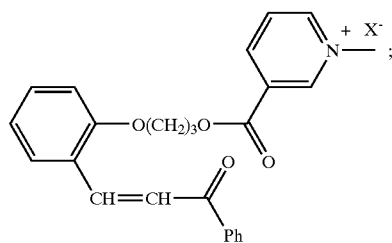
1066
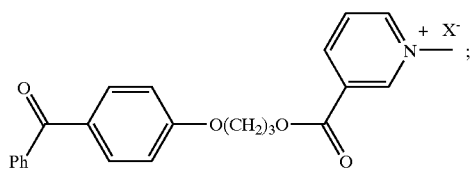
1068
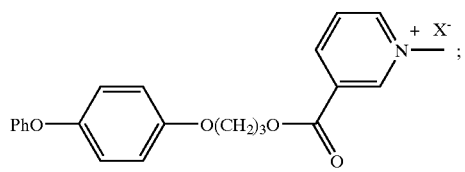
1070

TABLE 303-continued
A THIRD GROUPING OF BACTERIAL NAD SYNTHETASE
INHIBITOR LEAD COMPOUNDS
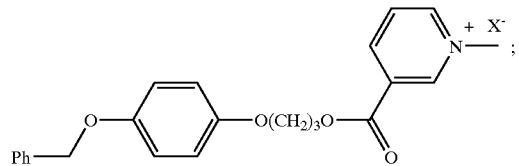
1072
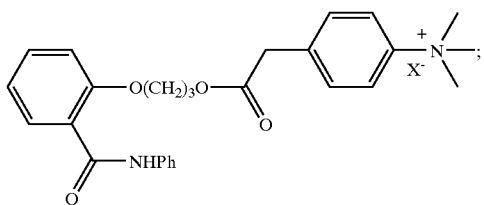
1074
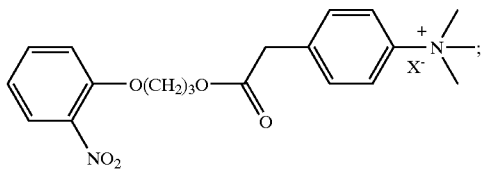
1075
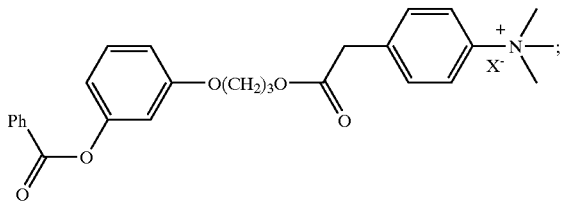
1079
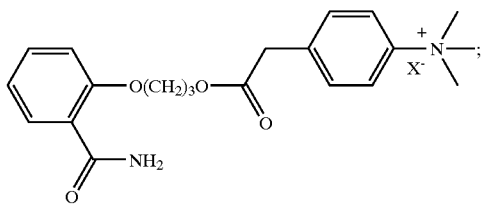
1080
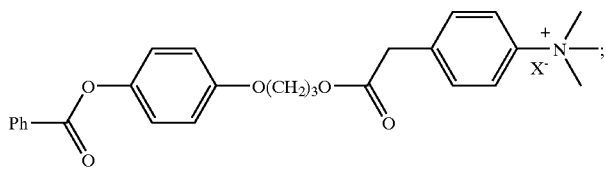
1082

TABLE 303-continued
A THIRD GROUPING OF BACTERIAL NAD SYNTHETASE
INHIBITOR LEAD COMPOUNDS
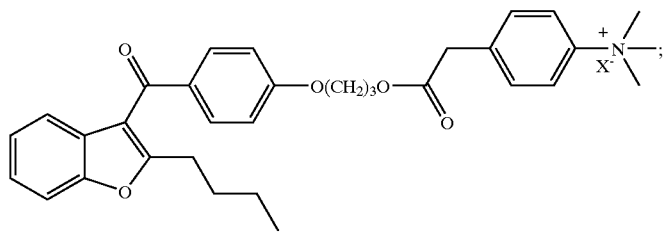
1084
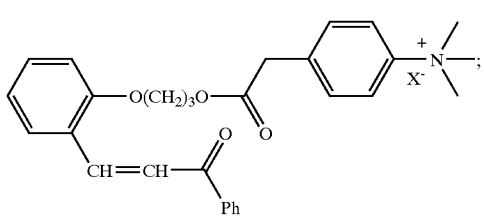
1086
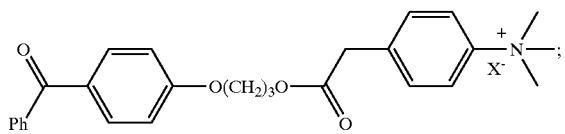
1088
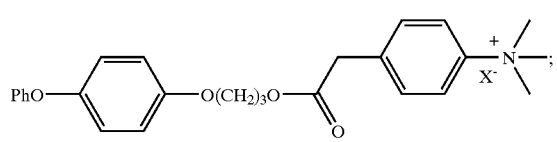
1090
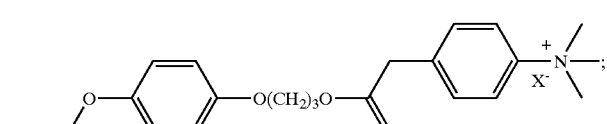
1094
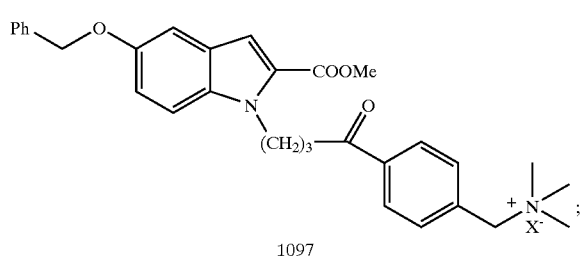
1097

TABLE 303-continued

A THIRD GROUPING OF BACTERIAL NAD SYNTHETASE INHIBITOR LEAD COMPOUNDS

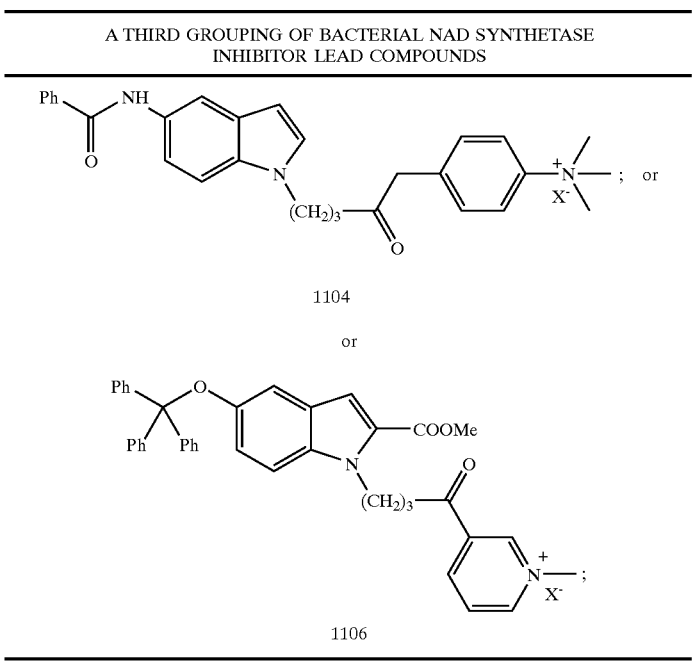

The compounds of the invention may be readily synthesized using techniques generally known to synthetic organic chemists. Suitable experimental methods for making and derivatizing aromatic compounds are described, for example, methods for making specific and preferred compounds of the present invention are described in detail in Examples 1 to 4 below.

This invention preferably further provides a method of generating a library comprising at least one bacterial NAD synthetase enzyme inhibitor compound comprising the steps of:

a. obtaining the crystal structure of a bacterial NAD synthetase enzyme;
b. identifying one or more sites of catalytic activity on the NAD synthetase enzyme;
c. identifying the chemical structure of the catalytic sites on the NAD synthetase enzyme;
d. selecting one or more active molecule compounds that will demonstrate affinity for at least one of the catalytic sites on the NAD synthetase enzyme;
e. synthesizing one or more dimeric compounds comprised of at least one active molecule wherein the active molecule compound are joined by means of n linker compounds and wherein n is an integer of from 1 to 12, and
f. screening the one or more compounds for NAD synthetase inhibitor activity.

The library further comprises one or more compounds set forth in Table 301 above. In one embodiment, a library of compounds according to the invention herein preferably includes compounds of the structures set out in structures 1 to 1106 above. Further preferably, the library comprises a compound of Structure 2, still preferably, Structure 4, further preferably, Structure 6, and further preferably, Structure 7. In further preferred embodiments, the library comprises at least one compound of Structure 8, Structure 10, Structure 12, Structure 16 or Structure 18.

In another preferred embodiment of the invention herein, the one or more dimeric compounds comprise at least two active molecules. Still preferably, the active molecules are the same. Alternatively, it is preferable that the active molecules are different.

In the invention herein, a software program that predicts the binding affinities of molecules to proteins is utilized in the active molecule selection step. Further preferably, a software program that evaluates the chemical and geometric complementarity between a small molecule and macromolecular binding site is utilized in the active molecule selection step.

In yet another preferred embodiment, the compounds are synthesized utilizing a rapid, solution phase parallel synthesis and wherein the compounds are generated in a combinatorial fashion.

In a preferred embodiment, the invention provides a method of treating or preventing a microbial infection in a mammal comprising administering to the mammal a treatment effective or treatment preventive amount of a bacterial NAD synthetase enzyme inhibitor compound. In a particularly preferred embodiment, the compound administered in the method is a compound as set out previously in Table 301. In another embodiment, invention herein preferably includes compounds 1 to 1106 above. Further preferably, the compound administered comprises at least one compound of Structure 2, still preferably, Structure 4, further preferably, Structure 6. In further preferred embodiments, the compounds administered in the method comprise compounds of Structure 8, Structure 10, Structure 12, Structure 16 or Structure 18.

In a preferred embodiment, the invention provides administering a broad spectrum antibiotic to a mammal in need of such treatment or prevention. In a further preferred embodiment, the microbial infection is a bacterial infection. In yet another embodiment of the invention, the bacterial infection is caused by a bacterium that is a gram negative or gram positive bacteria The bacterial infection may preferably be caused by an antibiotic resistant strain of bacteria.

Further provided by the invention herein is preferably a method of killing a prokaryote with an amount of prokaryotic NAD synthetase enzyme inhibitor compound to reduce or eliminate the production of NAD whereby the prokaryote is killed. A method of decreasing prokaryotic growth, comprising contacting the prokaryote with an amount of a prokaryotic NAD synthetase enzyme inhibitor effective to reduce or eliminate the production of NAD whereby prokaryotic growth is decreased is also provided. In the method of killing a prokaryote, as well as in the method of decreasing prokaryotic growth, the compound comprises one or more compounds of Table 301, Table 302 or Table 303. Still preferably, the invention comprises one or more of compounds 1 to 1106 above. Further preferably, the compound administered is a compound of Structure 2, still preferably, a compound of Structure 4, further preferably, Structure 6. In further preferred embodiments, the compounds administered in the methods compounds of Structure 7, Structure 8, Structure 10, Structure 12, Structure 16 or Structure 18.

In the method of killing a,prokaryote, as well as in the method of decreasing prokaryotic growth, the prokaryote is a bacterium. Further preferably, the bacterium is a gram negative or a gram positive bacteria. Still preferably, the prokaryote is an antibiotic resistant strain of bacteria.

Also in the method of killing a prokaryote, as well as in the method of decreasing prokaryotic growth, the NAD synthetase enzyme inhibitor is a compound that selectively binds with catalytic sites or subsites on a bacterial NAD synthetase enzyme to reduce or eliminate the production of NAD by the bacteria.

In the methods discussed above, the compound is preferably administered by oral, rectal, intramuscular, intravenous, intravesicular or topical means of administration. The compounds of this invention can be administered to a cell of a subject either in vivo or ex vivo. For administration to a cell of the subject in vivo, as well as for administration to the subject, the compounds of this invention can be administered orally, parenterally (e.g., intravenously), by intramuscular injection, by intraperitoneal injection, subcutaneous injection, transdermally, extracorporeally, topically, mucosally or the like.

Depending on the intended mode of administration, the compounds of the present invention can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected composition, possibly in combination with a pharmaceutically acceptable carrier and, In addition, may include other medicinal agents, pharmaceutical agents, carriers, adjuvants, diluents, etc.

Parenteral administration of the compounds of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous and intratracheal routes. One approach for parenteral administration involves use of a slow release or sustained release system such that a constant dosage is maintained. See e.g., U.S. Pat. No. 3,610,795, which is incorporated by reference herein. These compounds can be present in a pharmaceutically acceptable carrier, which can also include a suitable adjuvant. By "pharmaceutically acceptable," it is meant a material that is not biologically or otherwise undesirable, i.e., the material may be administered to an individual along with the selected compound without causing substantial deleterious biological effects or interacting in a deleterious manner with any of the other components of the composition in which it is contained.

Routes of administration for the compounds herein are preferably in a suitable and pharmacologically acceptable formulation. When administered to a human or an animal subject, the bacterial NAD synthetase enzyme inhibitor compounds of the libraries herein are preferably presented to animals or humans orally, rectally, intramuscularly, intravenously, intravesicularly or topically (including inhalation). The dosage preferably comprises between about 0.1 to about 15g per day and wherein the dosage is administered from about 1 to about 4 times per day. The preferred dosage may also comprise between 0.001 and 1 g per day, still preferably about 0.01, 0.05, 0.1, and 0.25, 0.5, 0.75 and 1.0 g per day. Further preferably, the dosage may be administered in an amount of about 1, 2.5, 5.0, 7.5,10.0, 12.5 and 15.0 g per day. The dosage may be administered at a still preferable rate of about 1, 2, 3, 4 or more times per day. Further, in some circumstances, it may be preferable to administer the compound of the invention continuously, as with, for example, intravenous administration. The exact amount of the compound required will vary from subject to subject, depending on the species, age, weight and general condition of the subject, the particular compound used, its mode of administration and the like. Thus, it is not possible to specify an exact amount for every compound. However, an appropriate amount can be determined by one of ordinary skill in the art using only routine experimentation given the teachings herein.

If ex vivo methods are employed, cells or tissues can be removed and maintained outside the subject's body according to standard protocols well known in the art. The compounds of this invention can be introduced into the cells via known mechanisms for uptake of small molecules into cells (e.g., phagocytosis, pulsing onto class I MHC-expressing cells, liposomes, etc.). The cells can then be infused (e.g., in a pharmaceutically acceptable carrier) or transplanted back into the subject per standard methods for the cell or tissue type. Standard methods are known for transplantation or infusion of various cells into a subject.

It is further provided a method of disinfecting a material contaminated by a microbe, comprising contacting a contaminated material with a bacterial NAD synthetase enzyme inhibitor compound in an amount sufficient to kill or deactivate the microbe. In yet another embodiment, the compound utilized for contacting comprises one or more compounds of Table 301, Table 302 or Table 303. The compounds utilized for contacting may also comprise one or more of compounds 1 to 1106. Further preferably, the compound utilized for contacting is a compound of Structure2, still preferably, a compound of Structure 4, further preferably, Structure 6. In further preferred embodiments, the compounds utilized for contacting in the method comprise compounds of Structure 7, Structure 8, Structure 10, Structure 12, Structure 16 or Structure 18.

In yet a further embodiment of the invention herein, the compounds of the present invention are effective as disinfectant materials for, for example, hard or soft surfaces, fabrics, and other contaminated materials such as those in hospitals, households, schools, nurseries, and any other location. In yet another embodiment, the invention provides a method for disinfecting comprising contacting a bacterial contaminated material with a bacterial NAD synthetase enzyme inhibitor compound.

In a further aspect of the invention, an in vitro "one-at-a-time" method of screening compounds for bacterial NAD synthetase enzyme inhibitory activity is provided. In a preferred embodiment, this in vitro method of screening compounds for such activity comprises the steps of preparing a solution comprising pure bacterial NAD synthetase enzyme, contacting the solution with the compounds set out herein, and determining the rate of the enzyme-catalyzed reaction. Preferably, measurement of the rate of enzyme-catalyzed reaction comprises a measure of NAD synthetase inhibitory activity. In a further embodiment the rate of enzyme-catalyzed reaction comprises a measure of antibacterial activity. In a still further embodiment, the rate of enzyme-catalyzed reaction corresponds to a measure of antimicrobial activity.

Preferably, the method of preparing the bacterial enzyme solution for use in the in vitro screening method comprises utilizing molecular biological methods to over-express bacterial NAD synthetase enzyme, for example from *B. subtilis*, in *E. coli*. One of skill in the art will recognize techniques useful for such a process. A particularly preferable method comprises: a) cloning the Out B gene encoding NAD synthetase enzyme and over-expressing the gene in *E. coli*; b) purifying the cloned and over-expressed gene by ion-exchange; c) purifying further the enzyme material from step b using ion-exchange methods; d) further purifying the material from step c using size exclusion chromatography wherein the bacterial NAD synthetase enzyme is essentially pure; and e) preparing an assay solution in quantities of about 10 to 15 mg pure bacterial NAD synthetase enzyme per liter of fermentation-broth. As used herein, "essentially pure" means greater than about 90% purity, more preferably, greater than about 95% purity and, still more preferably, greater than about 99% purity.

In one embodiment of the in vitro screening method, the following procedure is utilized to measure the rate of enzyme catalyzed reaction. A solution of HEPPS, pH 8.5, with KCl is prepared containing the following species: ATP, NaAD, MgCl$_2$, NH$_4$Cl, ADH, and ETOH. A stock solution of test inhibitors is then prepared by dissolving solid samples into 100% DMSO. The test compound stock solution is then added to the mixture to give the final test compound concentrations. NAD synthetase enzyme solution is added, the mixture is mixed three times, and the absorbance at 340 nm is then monitored kinetically using an UV-Vis spectrophotometer. The initial kinetics trace after enzyme addition is then fit to a straight line using linear regression, with this rate is then compared to that of a control containing no inhibitor, using the following formula to calculate % Inhibition: {(Vo−V)/Vo}*100%, where Vo is the rate of the reaction with no test compound present and V is the rate of the reaction with test the test compound added. Each compound is tested in triplicate, and the resulting values for % inhibition were averaged to give the listed value. IC$_{50}$ (concentration needed to inhibit 50% of the test bacteria) values were obtained for select compounds by assaying six different concentrations of test compound, in triplicate, at concentrations between 0.0 and 2.0 mM, and plotting the resulting % inhibition values against the −LOG of the test compound dose to reveal the concentration at which 50% inhibition is observed.

Preferably, the in vitro method can also be adapted to allow screening for compounds with bacterial NAD synthetase enzyme inhibitory activity in other forms of bacteria, as well as other types of microbes. For example, the above-described procedure can be adapted to screen for inhibitory activity in at least the following bacteria types:

| BACTERIUM | STRAIN |
|---|---|
| *Escherichia coli* K-12 | MG1655 (CGSC#6300) |
| *Escherichia coli* K-12 | W3110 (CGSC#4474) |
| *Salmonella typhimurium* | LT2 TT366 |
| *Streptococcus pneumonia* | D39 |
| *Streptococcus pneumoniae* | WU2 |
| *Bacillus subtilis* | A700 |

In a further embodiment of the in vitro screening method, the method can be used to screen existing compounds e.g., commercially available compounds, such as 5-nitroindole and N-methyl nicotinic acid. One of skill in the art will recognize the manner in which the designing and screening methods herein can be utilized to identify commercially available compounds, such as the previous non-exhaustive list, that will exhibit NAD synthetase enzyme inhibitory activity, both in bacteria and other microbes.

In order to test a library of NAD synthetase enzyme inhibitor compounds, such as those of the present invention, it is particularly preferable to utilize a method of rapid (high throughput) screening. To this end, the potential inhibitory activity of the library of synthetic compounds in one embodiment is assessed via a coupled enzymatic assay. The coupled assay involves two steps as summarized below.

Step 1

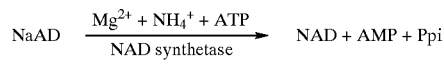

Step 2

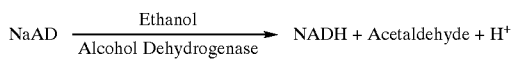

In order to rapidly measure the inhibitory activities of the compounds in the library, the invention provides a high through-put screening system (HTS system). The HTS system preferably utilizes an integrated robotic system that coordinates the functions of a liquid handler and a spectrophotometer. The robotic station is preferably responsible for the movement of all hardware and the integration of multiple stations on the work surface. The liquid handler is preferably programmed to perform all phases of liquid dispensing and mixing. The spectrophotometer is preferably equipped to monitor absorbance in a 96-well plate format.

In one embodiment, the assay is designed for a 96-well plate format reaction buffer containing HEPPS buffer, pH 8.5, MgCl$_2$, NH$_4$Cl$_2$, KCl, NAAD, n-Octyl-D-Glucopyranoside, ethanol, NAD synthetase, and yeast alcohol dehydrogenase. At the next stage, the liquid handler dispenses DMSO (with or without inhibitor) into the reaction well. The liquid handler mixes these components utilizing a predefined mixing program. The reaction is initiated by the addition of a solution of ATP dissolved in buffer. The reaction is monitored by measuring the increase in absorbance at 340 nm. The linear portion of the reaction is monitored for a period of time. The initial velocity is determined using the software supplied with the spectrophotometer.

The compounds of the library herein are supplied as a stock with a concentration dissolved in 100% DMSO. An initial screen is conducted on all compounds using a 2 or 3 concentration screen. The 2 panel screen used concentrations of 0.2 mM and 0.1 mM for the compounds. The 3 panel screen used concentrations of 0.2 mM, 0.1 mM, and 0.05 mM. From the initial screen, "lead compounds" e.g., those compounds which demonstrated the greatest inhibitory capacity, are then preferably subjected to a wider screen of -concentrations (0.1 mM to 0.001 mM) to determine the apparent IC-50 values for each compound.

In still a further preferred embodiment of the invention herein, the high through-put method is utilized to screen commercially available compounds for bacterial NAD synthetase enzyme inhibitory activity. In an additional embodiment, the NAD synthetase enzyme inhibitor compounds are tested as inhibitors of bacterial growth against a variety of bacteria types.

In a further embodiment of the invention, compounds within the libraries of NAD synthetase inhibitor compounds are evaluated for antibacterial and antimicrobial activity. In one embodiment, compounds are preferably evaluated for their potential to inhibit the growth of *Bacillus subtilis, Pseudomonas aeruginosa*, and *Staphylococcus epidermitis*. The inhibitors are preferably initially screened in duplicate at one concentration The test inhibitor compounds are prepared by dissolving the solid samples in DMSO. Aliquots from the inhibitor stocks are placed in sterile 96-well plates by the liquid handler discussed previously. Cultures of *B. subtilis, P. aeruginosa* and *S. epidermitis* are prepared in liquid broth (LB) media and incubated in an orbital shaker overnight. Dilutions (with LB media) of the overnight cultures are added to the 96-well plates containing the inhibitors. The plates are incubated and the absorbance measured at 595 nm in a plate reader.

In this embodiment of the invention, a diluted overnight culture without inhibitors serves as one of three controls in the experiments. A positive control, which includes an identical concentration of the drug Tobramycin as the inhibitors being tested, and a DMSO control are also performed during each inhibitor screen. The DMSO control was included for comparison with the control that contained no inhibitors.

Percent inhibition of each inhibitor was calculated by the following formula: $\{(A_D-A_I)/A_D\}*100$; where AD=the absorbance at 595 nm of the DMSO control and $A^I$=the absorbance of the inhibitor at 595 nm.

In a further embodiment, dose responses are performed on the compounds that inhibited greater than 85% in the initial screen. The dose responses consisted of 5 different concentrations (from 100 mM–0.1 mM) of each inhibitor and the positive control Tobramycin. The cultures are prepared and grown in the same manner as the inhibitor screens and the same controls were included. The absorbance is measured every hour and a half during the six hours of growth. Percent inhibitions are calculated again for each concentration tested. The lowest concentration that resulted in an 85% inhibition or higher is termed the Minimum Inhibitory Concentration that inhibited bacterial growth 85% ($MICe_5$).

When a NAD synthetase enzyme inhibitor compound of a library herein are to be administered to a humans or an animal e.g., a mammal, it is preferable that the compounds show little or no toxicity to the patient. Therefore, in one embodiment of the invention herein, the toxicities of the NAD-synthetase enzyme inhibitors are evaluated using human epithelial cells as set out in Example 11 below.

EXAMPLES

The following examples are set forth so as to provide those of ordinary skill in the art with a complete disclosure and description of how the compositions and methods claimed herein are made and evaluated and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Experimental Procedure for Preparing Compounds Singly in Scheme 3 (N=6).

The following Example 1 describes one embodiment of the invention herein for compounds prepared according to the synthetic pathway set out in Scheme 3, described previously. For this particular Example, the linker length e.g., n, is equal to 6. Compounds prepared according this embodiment were prepared, individually, i.e., not using parallel solution phase synthesis methods. One of skill in the art will readily recognize the manner in which the following Example may be varied to obtain the linker lengths within the scope of the present invention.

A. Alkylation of 5-nitroindole with 6-bromohexyl acetate. A solution of 5-nitroindole (1.00 g, 6.22 mmol) in DME (2.0 mL) was added dropwise using an addition funnel to the suspension of NaH (0.24 g, 0.01 mmol in 2.0 mL DME), previously washed with DME (3×3.0 mL). The sides of the addition funnel were rinsed with an additional 2.0 mL of DME. During the addition, an instantaneous gas evolution occurred. The reaction flask was then immersed into a preheated oil bath at 80° C. and allowed to gently reflux for 15 minutes. The flask was then cooled to ambient temperature and a solution of 5-bromohexyl acetate (1.39 g, 6.22mmol) dissolved in DME (2.0 mL) was added dropwise using the addition funnel. The sides of the funnel were washed with an additional portion of DME (2.0 mL). The reaction flask was then immersed into a preheated oil bath set at 80° C. and allowed to reflux for 18 hours. Workup consisted of quenching the reaction using saturated $NH_4Cl$ (25 mL) and extracting the aqueous layer with ethyl acetate (4×25 mL). The organic layers were combined, dried over anhydrous $Na_2SO_4$, filtered, and evaporated to dryness under reduced pressure. The product was then purified by flash chromatography on silica gel using hexane-acetone (9:3) to afford the product (0.39 g) and deacetylated product (1.11 g, for a combined yield 91.2%). The acetylated product was isolated as a yellow colored viscous oil.

The acetylated product from Step A was analyzed, yielding the following confirmatory data: IR (KBr) 1735 (C=O) $cm^{-1}$; $^1$H-NMR (300 MHz) δ 8.59 (d, 1H, H-4, J=2.2 Hz), 8.12 (dd, 1H, H-6, J=9.1, 2.2 Hz), 7.35 (d, 1H, H-7, J=9.1 Hz), 7.26 (d, 1H, H-2, J=3.2 Hz), 6.68 (d, 1H, H-3, J=3.2 Hz); 4.17 (t, 2H, N—C$\underline{H}_2$, J=7.1 Hz), 4.04 (t, 2H, O—C$\underline{H}_2$, J=6.6 Hz), 2.03 (s, 3H, acetate), 1.90 (quintet, 2H, N—CH$_2$—C$\underline{H}_2$, 2H, J=7.2, 7.5 Hz), 1.61 (quintet, 2H, O—CH$_2$—C$\underline{H}_2$, J=6.8, 7.1 Hz), 1.37 (m, 4H, N—CH$_2$—CH$_2$—C$\underline{H}_2$); $^{13}$C-NMR (75 MHz) δ 170.8 (acetate), 141.0 (C-5), 138.5, 130.7, 127.4, 117.8, 116.7, 108.9, 103.6, 63.9 (O—C$\underline{H}_2$), 46.4 (N—C$\underline{H}_2$), 29.8, 28.1, 26.2 (CH$_3$, acetate), 25.3, 20.7; MS (ES, m/z) 327 amu (M +Na$^+$) (100), 305 (M+H$^+$); Anal. Calcd. for $C_{16}H_{20}N_2O_4$: C,63.14; H, 6.65; N, 9.20. Found: C, 63.09; H, 6.61; N, 9.14.

B. Transesterification of 6-[N5-nitroindolyl)]hexyl acetate. The indole acetate from Step A (1.07 g, 3.52 mmol) was dissolved in methanol (25 mL) and anhydrous $K_2CO_3$ (1.46 g, 10.57 mmol) was added. Water (8.0 mL) was then added to this suspension. The contents in the reaction flask were stirred for 20 hours at ambient temperature. The reaction was worked up by evaporation of the solvent under reduced pressure. The residue was then taken up in water (30 mL) and extracted successively with ethyl acetate (2×30 mL) and ether (3×30 mL). The combined extracts were dried over anhydrous $Na_2SO_4$, filtered, and evaporated under reduced pressure. The crude product was purified using flash chromatography on silica gel using ethyl acetate: hexane (6:4) to give Compound 862 as a pale yellow solid (0.85 g, 91.6%).

The material from Step B was analyzed yielding the following confirmatory data:

m.p. 78.3–78.7° C. IR (KBr) 3733 (OH) $cm^{-1}$; $^1$H-NMR (300 MHz) 8.60 (d, 1H, H-4, J=2.2 Hz), 8.12 (dd, 1H, H-6, J=9.1, 2.2 Hz), 7.36 (d, 1H, H-7, J=9,1 Hz), 7.25 (d, 1H, H-2, J=3.3 Hz), 6.68 (d, 1H, H-3, J=3.3 Hz), 4.18 (t, 2H, N—C$\underline{H}_2$, J=7.1 Hz), 3.63 (q, 2H, O—C$\underline{H}_2$, J=6.1, 11.6 Hz), 1.88 (quintet, 2H, N—CH$_2$—C$\underline{H}_2$, 2H, J=7.2, 7.5 Hz), 1.56 (quintet, 2H, O—CH$_2$—C$\underline{H}_2$, J=6.8, 7.1 Hz), 1.40 (m, 2H, N—CH$_2$—CH$_2$—C$\underline{H}_2$), 1.25 (t 1H, OH, J=5.4 Hz); $^{13}$C-NMR (75 Mz) 141.0 (C-5), 138.5, 130.9, 127.4, 118.0, 116.8, 109.0, 103.7, 62.4 (O—$\underline{C}H_2$), 46.6 (N—$\underline{C}H_2$), 32.3, 29.9, 26.5, 25.2, ; MS (ES, m/z) 263 amu (M+H$^+$) (100), 280 (M+NH$_4^+$), 285 (M+Na$^+$); Anal. Calcd. for $C_{14}H_{18}N_2O3$: C,64.10; H, 6.91; N, 10.68. Found: C, 64.21; H, 6.91; N, 10.69.

C. Esterification of 6-[N-(5-nitroindolyl)]hexan-1-ol using nicotinic acid. The alcohol from Step B (0.350 g, 1.37 mmol), nicotinic acid (0.210 g, 1.69 mmol), DCC (0.310 g, 1.51 mmol) and DMAP (17.0 mg, 0.140 mmol) were dissolved in dichloromethane (12.0 mL). The suspension was stirred at ambient temperature and monitored by TLC. After 20 hours the reaction was worked up by filtering off the white solid, washing the filter with dichloromethane (15.0 mL), and washing the organic filtrate with brine (3×25 mL). The filtrate was then dried over anhydrous $Na_2SO_4$ and evaporated to dryness. Purification of the product was done by flash chromatography on silica gel using ethyl acetate-hexane (6:4) to give the product as a yellow colored solid (0.45 g, 90%).

The material from Step C was analyzed yielding the following confirmatory data:

m.p. ° C.; IR (KBr) 1717 (C=O) $cm^{-1}$; $^1$H-NMR (300 MHz) δ 9.13 (d, 1H, H-2', J=1.9 Hz), 8.71 (dd, 1H, H-6', J=4.8, 1.5, Hz), 8.51 (d, 1H, H-4, J=2.2 Hz), 8.20 (dt, 1H, H-4', J=2.0, 6.0 Hz), 8.03 (dd, 1H, H-6, J=9.1, 2.2 Hz), 7.32 (dd, 1H, H-5', J=4.8, 1.1 Hz 7.29 (d, 1H, H-7, J=9.1 Hz), 7.17 (d, 1H, H-2, J=3.2 Hz), 6.60 (d, 1H, H-3, J=3.2 Hz); 4.25 (t, 2H, N—CH$_2$, J=6.5 Hz), 4.11 (t, 2H, O—C$\underline{H}_2$, J=7.0 Hz), 1.83 (quintet, 2H, N—CH$_2$—C$\underline{H}_2$, 2H, J=7.2, 7.5 Hz), 1.70 (quintet, 2H, O—CH$_2$—C$\underline{H}_2$, J=6.8, 7.1 Hz), 1.36 (m, 2H,N—CH$_2$-CH$_2$—C$\underline{H}_2$); $^{13}$C-NMR (75 MHz) δ 164.9 (nicotinate C=O), 153.1 (C-2'), 150.5 (C-6'),141.5 (C-5), 138.4(C-7), 136.7 (C4'), 130.8 (C-2), 127.3 (C-3'), 125.8 (C-3), 123.1 (C-5'), 117.8 and 116.8 (C-4,6), 108.9 (C-7), 103.6 (C-3), 64.9 (O—$\underline{C}H_2$), 46.5 (N—$\underline{C}H_2$), 29.7 (O—CH$_2$ $\underline{C}H_2$, 28.2 (N—CH$_2$ $\underline{C}H_2$), 26.3 (O—CH$_2$CH$_2$—$\underline{C}H_2$), 25.4; MS (ES, m/z) 368 amu (M+H$^+$) (100).

D. N-Methylation of 6-[N-(5-nitroindolyl)]hexyl nicotinate. The ester from Step C (0.104 g, 0.294 mmol) was mixed with iodomethane (0.036 mL, 0.589 mmol). The reaction was heated in an oil bath to 60° C. overnight (18 hours). The work-up consisted of evaporating the solvent under reduced pressure then recrystallization of the residue using 2-propanol to give a yellow colored solid (0.120 g, 82.3%).

The material from Step D was analyzed yielding the following confirmatory data:

m.p. 109.1–109.90° C.; IR (KBr) 1717 (C=O) $cm^{-1}$; $^1$H-NMR (300 MHz) δ 9.42 (sm 1H,H-2'), 9.11 (d, 1H, H-6', J=6.1 Hz), 8.63 (d, 1H, H-4', J=8 Hz), 8.50 (d, 1H, H-4, J=2.0 Hz), 8.19 (dt, 1H, H-6, J=6.3, 7.9 Hz), 8.01 (dd, 1H, H-5', J=2.3, 9.1 Hz), 7.56 (d, 1H, H-7, J=9.1 Hz), 7.50 (d, 1H, H-2, J=3.1 Hz); 6.69 (d, 1H, H-3, J=330 Hz); 4.50 (s, 3H, N$^+$—CH$_3$); 4.42 (t, 2H, N—C$\underline{H}_2$, J=6.4 Hz), 4.31 (t, 2H, O—C$\underline{H}_2$, J=6.9 Hz), 1.95 (quintet, 2H, N—CH$_2$—C$\underline{H}_2$, 2H, J=7.2, 7.5 Hz), 1.84 (quintet, 2H, O—CH$_2$—C$\underline{H}_2$, J=6.8, 7.1 Hz), 1.46 (m, 2H, N—CH$_2$—CH$_2$—C$\underline{H}_2$); $^{13}$C-NMR (75 MHz) δ 162.7 (nicotinate C=O), 149.8 (C-), 148.2 (C-), 142.7 (C-5), 140.5 (C-7), 133.2 (C-4'), 132.2 (C-2), 129.4 (C-3'), 129.3 (C-3), 118.8 and 117.8 (C-4,6), 111.1 (C-7), 104.8 (C-3), 67.7 (O—$\underline{C}H_2$), 49.6 (N$^+$—CH$_3$), 47.5 (N—$\underline{C}H_2$), 30.9 (O—CH$_2$ $\underline{C}H_2$, 29.2 (N—CH$_2$ $\underline{C}H_2$), 24.2 (O—CH$_2$CH$_2$—$\underline{C}H_2$); MS (ES, m/z) 368 amu (M+) (100), 127 (I$^-$) (100); Anal. Calcd. for $C_{20}H_{24}N_3O_4I$: C, 48.50; H, 4.48; N, 8.48. Found: C, 48.36; H, 4.46; N, 8.34.

The synthetic procedures described below with respect to Schemes 4–6 were developed for use as combinatorial chemical methods using, for example, parallel solution phase synthesis techniques. One of skill in the art would recognize the meaning of these terms.

Example 2

General Experimental Procedures Used for Preparing Solution Phase Combinational Libraries Described in Scheme 4

The following Example 2 describes a preferred embodiment of the invention herein for compounds prepared according to the synthetic pathway set out in Scheme 4, described previously. One of skill in the art will recognize that many possible variations of this embodiment exist that will not result in deviation from the novel and unobvious aspects of the invention. A. Alkylation of 5-nitroindole with the bromoalkyl acetate and conversion of the indole alkyl acetate to the alcohol. A solution of 5-nitroindole (1 g, 6.17 mmol) in DMF (10.0 mL) was prepared in 4 dram vials (size 28×57 mm) This solution was then transferred to a second 4 dram vial containing a suspension of NaH (0.22 g, 9.25 mmol) in DMF (8.0 mL). During the addition, an instantaneous gas evolution was observed and a nitrogen inlet was used to prevent gas pressure build up. The robotic synthesizer was then used to dispense 3.0 mL of the indole sodium salt solution into 5 culture tubes (16×125 mm) in a synthesizer block. The bromoalkyl acetate (1.36 mmol) was dissolved in DMF (8 mL total volume, 1.36M solution) in a 4 drain vial, 1 mL of this solution was transferred into designated test tubes using the robotic synthesizer. After allowing the reaction to block shake for 15 hours at ambient temperature, tris(2-aminoethyl)amine resin (0.15 g, 0.329 mmol) was added and the reaction was shaken for 12 hours with heating at 55° C. The resin was filtered using 3cc syringes each with a cotton plug and connected to a 24-port manifold and a water aspirator provided vacuum suction The filtrate was collected in culture tubes (16×125 mm) and the resin was washed using MeOH (3.0 mL). Prior to placing the tubes in the reaction block a catalytic amount of NaH (10–12 mg) was added to each tube and allowed to shake at ambient temperature for 12 hours. Work-up consisted of adding ethyl acetate (4.0 mL) and water (3.0 mL) to each sample, shaking and removing the organic layer then subsequently washing the organic layer using brine (2×3.0 mL). The organic layer was dried over anhydrous $Na_2SO_4$, filtered vide supra, and the solvent was transferred to 4 dram vials evaporated using a speed vac to give the alcohol as a solid residue whose weight range was from 100 mg to 226 mg.

B. Formation of the indole alkyl ester. The alcohol (0.100 g, 0.381 mmol) was purged with argon and dissolved in dichloromethane (5.0 mL), 1 mL aliquots were transferred to 5 culture tubes (13×100 mm), triethylamine (106 μL) was added to each tube, and the tubes were then capped and placed in an ice bath for 15 minutes. Methanesulfonyl chloride (38 μL) was then added to each vial, then shaken by hand for 10 seconds and placed in the refrigerator at 1.8° C. for 12 hours. Each sample was worked up by the addition of ethyl acetate (5 mL), and washed with water (2×3 mL) and brine (3 mL). The organic layer was dried by passing it through a B-D 3 cc syringe containing anhydrous $NaSO_4$ using the manifold described above and collecting the filtrate in culture test tubes (16×125 mm). The solvent was then transferred to 4 dram vials and evaporated vide supra to give residue weights of 0.128 g to 0.159 g. The residue in the vials (0.128 g, 0.498 mmol) was then purged with argon and dissolved in anhydrous DMF (3mL). This solution was then transferred to culture tubes (13×100 mm) containing 2 equiv. of nicotinic acid (457 mg, 1.72 mmol) and 1 equiv. $K_2CO_3$ (120 mg, 0.858 mmol) in DMT (5 mL). The tubes were shaken and heated in a digitally controlled heating block at 50° C. for 15 hours. The reactions were worked up by pouring the contents of the tubes into 4 dram vials containing ethyl acetate (5 mL), and this was washed with water (2×5 mL) and brine (2×5 mL). The organic layer was dried by passing it through a 3 cc syringe containing anhydrous $Na2SO_4$ vide supra. The filtrate was collected into culture tubes (16×125 mm) and transferred to 4 dram vials and evaporated under reduced pressure to give the ester as a residue whose weight range was 27 mg to 59 mg.

C. N-Methylation. The ester from Step B above, (32 mg, 0.108 mmol) was transferred into culture tubes (13×100 mm) and dissolved in DME (1.5 mL) then followed by the addition of 5 equiv. of iodomethane (36 μL, 0.077 mmol). The tubes were shaken and heated in a digital heating block at 50° C. for 12 hours. Work-up consisted of transferring the contents of the tubes into 1 dram vials and evaporating the solvent under reduced pressure to give the N-methyl derivative as a solid product (weight range 17 mg to 39 mg) which was isolated by filtration.

Example 3

General Experimental Procedures Used for Preparing Solution Phase Combinatorial Libraries Described in Scheme 5

The following Example 3 describes a preferred embodiment of the invention herein for compounds prepared according to the synthetic pathway set out in Scheme 5, described previously. One of skill in the art will recognize that many possible variations on this embodiment exist that will not result in deviation from the novel and unobvious aspects of the invention.

A. Methyl and benzyl esters of indole carboxylates. Potassium carbonate (0.55 eq) was added to indole carboxylic acid (6.1 mmol) stirred in dry DMF (10 mL) at r.t. After 10 min., the alkyl iodide (benzyl or methyl) (1.1 eq) was added. This was worked up after 24 hours in 30 mL centrifuge tubes by taking the RM, diluting in EtOAc (25 mL), and washing with $NaHCO_3$ (2×10 mL), $H_2O$ (2×10 mL), and brine (10 mL). The resulting solution was dried ($Na_2SO_4$), evaporated to dryness, and recrystallized from EtOAc-hexanes.

B. N-Alkylation of indole esters with bromoalkyl acetates. NaH (2.93 mmol) was washed with dry DMF (4 mL), re-suspended in dry DMF (7 mL) and cooled at 0° C. under a nitrogen atmosphere. A solution of the dry indolecarboxylate ester (1.95 mmol) in dry DMF (7 mL) was slowly added, dropwise, to the NaH suspensions contained in 20 mL vials. This was under mixed on an orbital shaker and warmed to r.t. After 1 hour, 2 mL of each 14 mL solution was dispensed into 7 100×13 cultures tubes (7×7=49 tubes containing 0.285 mmol each).

For each linker size (e.g., n=5 to 9), the bromoalcohol acetate (7.7 eq) was diluted to to 3.5 mL with dry DMF. A portion of this solution (0.5 mL, 1.1 eq., 0.313 mmol) was slowly added to the reaction mixture containing the indole anions. The mixtures were shaken at r.t. for 15 hours. TLC for product revealed Rf=0.3 to 0.7 (3:7 EtOAc-hexanes).

Each culture tube was treated with a polymer supported trapping resin, tris(2-aminoethyl)amine (0.16 eq, 0.046 mmol), and the tubes were shaken at 50° C. for 6.5 hours. The mixture was filtered through cotton in 1 mL syringes using a 24 port manifold, the. filter was washed with dry MeOH (2 mL), and the filtrate was collected and concentrated in 100×13 mm culture tubes to provide the product.

C. Formation of the alcohol from the indolealkyl acetate. For the methyl esters, a MeOH—MeONa solution was prepared as follows: NaH (2.85 mmol) was washed with dry DMF (2×2 mL), suspended in dry DMF (2 mL), cooled at 0° C., and dry MeOH (8 mL) was slowly added. The resulting mixture was then shaken for 30 min at r.t. A portion (0.2 mL, 0.2 eq) of this solution was dispensed to each tube containing the indolealkyl acetate, and the resulting mixture was shaken at r.t. for 16 hours. The mixtures were diluted with EtOAC (6 mL) and extracted with $H_2O$ (5 mL) in 30 mL centrifuge tubes. The aqueous washes were re-extracted with EtOAc (3×2 mL). The combined EtOAc layers were washed with $H_2O$ (2×4 mL) and brine (2 mL), dried ($Na_2SO_4$), and filtered into 20 mL vials. The solvent was removed in a speed-vac under reduced pressure to provide the product: Rf=0.05 to 0.35 (3:7 EtOAc-hexanes).

For the benzyl esters, a 1 N NaOH solution (5 eq) was added to the indolealkyl acetate and the mixture was shaken for 2 days at r.t. The mixtures were diluted with EtOAC (6 mL) and extracted with $H_2O$ (5 mL) in 30 mL centrifuge tubes. The aqueous washes were re-extracted with EtOAc (3×2 mL). The combined EtOAc layers were washed with $H_2O$ (2×4 mL) and brine (2 mL), dried ($Na_2SO_4$), and filtered into 20 mL vials. The solvent was removed in a speed-vac under reduced pressure to provide the product: Rf=0.05 to 0.35 (3:7 EtOAc-hexanes).

D. Coupling of the indole alcohol with aromatic amines. To the alcohol (0.1 mmol) in dry $CH_2Cl_2$ (1 mL) was added the aromatic amine (10 eq. pyridine, quinoline, isoquinoline, or methyl nicotinate; 4 eq. benzyl 3-quinolinecarboxylate). The resulting mixture was cooled at 0° C. and trifluoromethanesulfonic anhydride (1.3 eq.) was slowly added. The mixture was shaken for 2 hours at 0° C., and then at r.t. for 14 hours. The reaction mixture was diluted with EtOAc (3 mL) and washed with 1 N HCl (3×1 mL), water (2×1 mL) and brine (1 mL). The solution was dried ($Na_2SO_4$) and concentrated on the speed-vac under reduced pressure to provide the product.

E. Conversion of the methyl and benzyl indolecarboxylates to the carboxylic acids. For methyl esters, the methyl indolecarboxylate (0.1 mmol) was solubilized in MeOH—$H_2O$ (3:1, 0.8 mL) and 1 N NaOH (7 eq for diesters, 5 eq for monoesters) was added. The reaction mixture was then heated at 45° C. on an orbital platform shaker for 14 hours. The solution was evaporated to dryness on a speed-vac and the residue dissolved in DMSO for biological evaluation.

Benzyl esters (0.04–0.09 mmol) were solubilized in a mixture of MeOH—$CH_2Cl_2$—$H_2O$ (8:1:1) (1.5 mL) were hydrogenated using Pd/C (10%) (50 mg) in 100×13 mm culture tubes containing 10 glass beads (diameter=3 mm) under 40 psi $H_2$ at r.t. for 8 hours. Under these conditions, 14 tubes could be placed in a 500 mL PAR apparatus bottle. Filtration through a celite pad and concentration on a speed-vac under reduced pressure afforded the carboxylic acids. Products containing the reduced pyridinium ring were also produced.

Example 4

General Experimental Procedures Used for Preparing Solution Phase Combinatorial Libraries Described in Scheme 6

The following Example 4 describes a preferred embodiment of the invention herein for compounds prepared according to the synthetic pathway set out in Scheme 6, described previously. One of skill in the art will recognize that many possible variations on this embodiment exist that will not result in deviation from the novel and unobvious aspects of the invention.

A. Bromination of anilines. An anhydrous dimethyl formamide (DMF) solution (40 mL) of a commercially available aniline (0.02 mol) was treated with N-bromosuccinimide (NBS, 1.1 eq.) at room temperature overnight. The resulting mixture was quenched by pouring it onto ice and extracted with ethyl acetate (EtOAc, 2×30 mL). The combined organic layers were washed with water (30 mL), brine (30 mL), dried over $MgSO_4$, filtered and concentrated to give the product.

B. Heck coupling. To an anhydrous triethylamine solution (TEA, 3 mL) of 2-bromo-R'-substituted-aniline (0.006 mol) (1 eq), in 10×1.3 cm test tubes, was added bis-triphenylphosphine palladium chloride (2 mol %) at room temperature followed by the addition of copper iodide (2 mol %). To this heterogeneous mixture, the corresponding terminal alkynol (1.5 eq.) and glass beads were added. The resulting mixture was allowed to react for 6 h at 80° C. under vigorous vortex shaking. Upon cooling, the reaction mixture was filtered through a celite bed (in 5 mL disposable syringes). Concentration under high vacuum (speed-vac) afforded the product.

C. Cyclization to form indoles. To an anhydrous acetonitrile (3 mL) solution of alkyne-substituted aniline in 10×1.3 cm test tubes at room temperature was added palladium chloride (2 mol %) followed by the addition of glass beads. The resulting mixture was heated to 60° C. for 1 h under vigorous vortex shaking. Upon cooling, the reaction mixture was filtered through a bed of celite (in 5 mL disposable syringes). The solvent was evaporated under high vacuum (speed-vac) to afford the products.

D. Quaternization with amines. To a cooled (0° C.) solution of the indole alcohol in aromatic amine (pyridine, quinoline, or isoquinoline) (2 mL) under a nitrogen atmosphere in 10×1.3 cm test tubes, was added trifluoromethanesulfonic anhydride ($Tf_2O$) (1.3 eq.). The resulting solution was allowed to react for 6 h. The reaction mixture was quenched by the addition of an ice-cold 1.5N HCl solution (3 mL) followed by the addition of EtOAc (4 mL). The organic layer was washed with water (3 mL), brine (3 mL), dried over $MgSO_4$, and filtered through a silica gel column (1×2 cm, in 5 mL syringes) in order to remove unreacted organic materials. The column was then flushed with a dichloromethane methanol (19:1) solution (4 mL). This extract was concentrated to afford the products.

E. Formation of isolated mesylate. To an anhydrous DCM solution (2 mL) of the indole alcohol was added TEA (1.5 eq.) at room temperature in 10×1.3 cm test tubes. The resulting solution was cooled to 0° C. and treated with methanesulfonyl chloride (1.1 eq.) for 1 h. The reaction mixture was quenched by the addition of water (3 mL), followed by DCM (3 mL). The organic layer was washed with brine (3 mL), dried over $MgSO_4$, filtered through a celite bed (in 5 mL disposable syringes) and concentrated under high vacuum (speed-vac) to give the indole mesylates.

F. Formation of ester. To an anhydrous DMF solution (2 mL) of the indole mesylate (1 eq.) in 10×1.3 cm test tubes was added the corresponding carboxylic acid ($R_3$—COOH, 2 eq.) followed by $K_2CO_3$ (2 eq.) and glass beads at room temperature. The resulting suspension was heated to 55° C. for 16 h under vigorous vortex shaking. Upon cooling the reaction mixture was quenched by adding water (3 mL) followed by ethyl acetate (3 mL). The organic layer was washed with brine (4 mL), dried under $MgSO_4$, filtered through a cotton bed (in 5 mL disposable syringes) and concentrated under high vacuum (speed-vac) to give the final ester.

Example 5

General Experimental Procedures Used for Preparing Libraries Described in Scheme 7

A. Experimental Procedure for Preparing Compounds Singly in Scheme 7 (n=7)

A. Alkylation of Phenol With 7-Bromo-1-heptanol

Phenol (0.098 g, 1.04 mmol) and 7-bromo-1-heptanol (0.243 g, 1.246 mmol) were dissolved in acetone (25 mL) in a 50 mL round bottomed flask. Potassium carbonate (0.86 g, 6.23 mmol) was added to this solution and the flask was fitted with a condenser and refluxed using an oil bath at 70° C. for a period of 26 hours. The reaction flask was then cooled to room temperature. The contents of the flask was then filtered through a fluted filter paper and washed with acetone (10 mL). The combined filtrate was then evaporated to dryness under reduced pressure. The residue obtained was dissolved in ethyl acetate (25 mL). The ethyl acetate solution was then washed with 1N. NaOH (3×5 mL), water (2×5 mL) and brine (2×5 mL). The organic layer was dried over $Na_2SO_4$. Removal of solvent from the dried extract under reduced pressure afforded the product. The product was then purified by flash chromatography (Si gel, 12×2.5 cm) using ethyl acetate: hexane (1:1) to afford the pure 7-(phenyloxy)-1-heptanol (0.22 g, quantitative yield). The product alcohol from step A was analyzed yielding the following confirmatory data: $^1$H-NMR (CDCl$_3$) δ 1.31–1.52 (m, 6H), 1.52–1.63 (m, 2H), 1.73–1.89 (m, 2H), 1.97 (bs, 1H), 3.61 (t, 2H, J=6.57 Hz), 3.93 (t, 2H, J=6.50 Hz), 6.80–6.97 (m, 3H) and 7.20–7.28 (m, 2H); $_{13}$C-NMR (CDCl$_3$) δ 25.5, 25.8, 29.0, 29.1, 32.4, 62.5, 67.7, 114.3, 120.3, 129.2 and 158.8; IR (neat): 3348 cm$^{-1}$; MS (ES$^+$): 209 (M+1).

B. Mesylation of 7-(Phenyloxy)-1-heptanol

A solution of 7-(phenyloxy)-1-heptanol (0.21 g, 1.01 mmol) in anhydrous methylene chloride (20 mL), taken in a 50 mL round bottomed flask was cooled to 0° C. using an ice bath. Methanesulfonyl chloride (0.177 g, 1.55 mmol) was added to this followed by a dropwise addition of triethylamine (0.28 mL, 2.11 mmol). The reaction mixture was then stirred at 0° C. for 1 hour and allowed to attain room temperature in 2 hours. It was then quenched with 1N. HCl (10 mL) and diluted with methylene chloride (20 mL). The organic layer was separated and the aqueous layer was extracted with methylene chloride (2×10 mL). The combined organic layer was washed with 1N. HCl (3×10 mL), water (2×10 mL) and brine (2×mL). The organic layer was dried over $Na_2SO_4$. Removal of solvent from the dried extract under reduced pressure afforded the product 7-(phenyloxy)-1-heptyl methanesulfonate (0.25 g, 86.5%). The product from the step B was analyzed yielding the following confirmatory data: $^1$H-NMR (CDCl$_3$) 1.31–1.52 (m, 6H), 1.71–1.84 (m, 4H), 2.98 (s, 3H), 3.94 (t, 2H, J=6.43 Hz), 4.21 (t, 2H, J=6.51 Hz), 6.80–6.94 (m, 3H) and 7.24–7.30 (m, 2H); $^{13}$C-NMR (CDCl$_3$) 25.2, 25.7, 28.6, 28.9, 29.0, 37.1, 67.5, 69.9, 114.3, 120.3, 129.2 and 158.9; IR (neat): 1349 cm$^{-1}$; MS (ES$^+$): 287 (M+1).

C. Esterification of 7-(Phenyloxy)-1-heptyl Methanesulfonate

A solution of 7-(phenyloxy)-1-heptyl methanesulfonate (0.2 g, 0.699 mmol) and nicotinic acid (0.173 g, 1.41 mmol) in anhydrous dimethyl formamide (15 mL) was placed in a 25 mL round bottomed flask. Potassium carbonate (0.097 g, 0.702 mmol) was added to this solution and the reaction mixture was heated at 50–55° C. using an oil bath for a period of 16 hours. It was then allowed to attain room temperature diluted with ethyl acetate (40 mL) and quenched with saturated NH$_4$Cl containing ice (20 mL). The organic layer was separated and the aqueous layer was extracted with ethyl acetate (3×10 mL). The combined organic layer was washed with saturated NAHCO$_3$ (3×10 mL), water (2×10 mL) and brine (2×10 mL). The organic layer was dried over $Na_2SO_4$. Removal of solvent from the dried extract under reduced pressure afforded the product 7-(phenyloxy)-1-heptyl nicotinate (0.176 g, 80.4%). The product ester from step C was analyzed yielding the following confirmatory data: $^1$H-NMR (CDCl$_3$) δ 1.38–1.62 (m, 6H), 1.76–1.92 (m, 4H), 3.95 (t, 2H, J=6.45 Hz), 4.35 (t, 2H, J=6.64 Hz), 6.85–6.98 (m, 3H), 7.22–7.38 (m, 2H), 7.38 (dd, 1H, $J_1$=7.93 Hz, $J_2$=4.93 Hz), 8.29 (dt, 1H, $J_1$=7.91 Hz, $J_2$=1.92 Hz), 8.77 (dd, 1H, $J_1$=4.83 Hz, $J_2$=1.70 Hz) and 9.23 (d, 1H, J=2.00 Hz), $^{13}$C-NMR (CDCl$_3$) δ 25.8, 25.9, 28.5, 28.9, 29.1, 65.4, 67.6, 114.3, 120.4, 123.2, 126.2, 129.3, 136.9, 150.8, 153.2, 158.9 and 165.2; IR (neat): 1712 cm$^{-1}$; MS (ES$^+$): 314 (M+1); Anal. Calcd. for $C_{19}H_{23}NO_3$: C, 72.80; H, 7.40 and N, 4.47. Found: C, 72.94; H, 7.54 and N, 4.51.

D. N-Methylation of 7phenyloxy)-1-heptyl nicotinate 7-(phenyloxy)-1-heptyl nicotinate (0.05 g, 0.159 mmol) was dissolved in anhydrous dimethoxyethane (5 mL) taken in a 10 mL round bottomed flask fitted with a condenser. Methyl iodide (0.2 ml, 3.21 mmol) was added to this and heated at reflux for 16 hours. It was then allowed to attain room temperature. The solid product formed was filtered, washed with hexanes and dried to obtain the product [7-(phenyloxy)-1-heptyl (N-methyl) nicotinate] iodide (0.04 g, 55.3%). The product from the step D was analyzed yielding the following confirmatory data. m.p. 82° C.; $^1$H-NMR (MeOH-d$_4$) δ 1.41–1.58 (m, 6H), 1.76–1.88 (m, 4H), 3.96 (t, 2H, J=6.54 Hz), 4.47 (t, 2H, J=6.74 Hz), 4.51 (s, 3H), 6.82–6.91 (m, 3H), 7.21–7.27 (m, 2H), 8.22 (dd, 1H, $J_1$=7.89 Hz, $J_2$=6.31 Hz), 9.03 (d, 1H, J=8.10 Hz), 9.12 (d, 1H, J=6.09 Hz) and 9.48 (s, 1H)); $^{13}$C-NMR (MeOH-d$_4$) 327.1, 27.2, 29.6, 30.2,30.4, 68.3, 68.9, 115.6, 121.6, 129.4, 130.5, 132.3, 146.4, 148.2, 149.8,160.67 and 162.9; IR (neat): 1719 cm$^{-1}$; MS (ES$^+$): 328 (M+); Anal. Calcd. for $C_{20}H_{26}NO_{31}$: C, 52.74; H, 5.76; N, 3.08. Found: C, 52.51; H, 5.77; N, 2.96.

B. General Experimental Procedures Used for Preparing Solution Phase Combinatorial Libraries Described in Scheme 7 (n=8)

A. General Considerations The solvents used were purchased as anhydrous in Sure-Seal™ bottles from Aldrich chemical company. The starting phenols (A) and reagents were purchased from Aldrich, Lancaster or Acros chemical companies and used as such. Reactions were carried out in an orbital shaker purchased from Digi-Block laboratory devices company. Evaporation of solvents were carried out in 25 ml wide mouthed vials using a Savant SC210 speedvac plus instrument. Parallel filtrations were carried out using a Burdick & Jackson 24-port manifold. Preparative parallel chromatography were performed on Baker flash silica gel (40μ) packed in 5 ml plastic disposable syringes.

B. Synthesis of Alcohols (B)

To the solution of commercially available phenols (A) (1–1.15 mmol) and 8-bromo-1-octanol (1.1 eq) in acetone (5ml) taken in screwcap vials (10 ml capacity), K$_2$CO$_3$ (6 eq) was added. The reaction mixtures were then capped and heated with orbital shaking (225 rpm) at 70° C. in a digiblock orbital shaker for 36 h. They were allowed to attain room temperature and filtered in parallel through syringe tubes fitted with cotton using the filtration manifold and washed with 5 ml of acetone each. The filtrates were concentrated using the speedvac. The residues obtained were dissolved in EtOAc (8 ml) each, washed with 1N. NaOH (2×2 ml), water (2×2 ml) and dried (Na$_2$SO$_4$). These were filtered in parallel through syringe tubes fitted with cotton using the filtration manifold. The filtrates were then evaporated using the speedvac to obtain the product alcohols (B) (70–97% yield).

C. Synthesis of Mesylates (C)

To the solutions of the alcohols (B) and Et$_3$N (2 eq) in CH$_2$Cl$_2$ (6 ml) at 0° C., MsCl (1.5 eq) was added and kept at 0° C. using an ice bath for 3 h with occasional stirring. They were diluted with CH$_2$Cl$_2$ (5 ml) and washed with 1N. HCl (3×2 ml), water (1×1 ml) and brine (1×1 ml) and dried (Na$_2$SO$_4$). These were filtered in parallel through syringe tubes fitted with cotton using the filtration manifold. Evaporation of solvent from the filtrates using the speedvac afforded the mesylates (C) (90–100% yield).

D. Synthesis of Esters (D-I, D-II)

To the solutions of the mesylates (C) and the acid (2 eq) in DMF (6 ml) taken in screwcap vials (10 ml capacity), K$_2$CO$_3$ (1 eq) was added. The reaction mixtures were then capped and heated with orbital shaking (225 rpm) at 55° C. in a digiblock shaker for 24 h. They were diluted with EtOAc (20 ml) and quenched with sat. NH$_4$Cl (5 ml). The organic layers were separated and the aqueous layers were extracted with 10 ml more of EtOAc. The combined organic extracts for each reaction were then washed with sat. NaHCO$_3$ (2×5 ml) and brine (2×5 ml) and dried (Na$_2$SO$_4$). These were filtered in parallel through syringe tubes fitted with cotton using the filtration manifold. Removal of solvent from the filtrates using a speedvac furnished the esters (D-I, D-II) (59–91% yield).

E. Synthesis of the Quaternary Salts (E-I, E-II)

To the solution of the esters (D-I, D-II) in DME (6 ml) in screwcap vials (10 ml capacity), MeI (30 eq) was added. The reaction mixtures were capped and heated with orbital shaking (225 rpm) at 85° C. in a digiblock shaker for 36 h. Then they were allowed to attain room temperature and solvent was completely evaporated using a speedvac. The crude products obtained were purified in parallel chromatography over Si gel columns (5×1 cm). The columns were first eluted with $CH_2Cl_2$ (20 ml), EtOAc (20 ml) and then with 10% MeOH in $CH_2Cl_2$ (30 ml) to obtain the quaternary salts (E-I, E-II) (40–92% yield).

Example 6

General Procedure for Crystallization, Data Collection and Determination of Structural Relationship Between NAD Synthetase Inhibitor Compounds and the NAD Synthetase Enzyme A. Crystallization. Protein was expressed and purified as described in the literature. (Nessi, C., Albertini, A., Speranza, M. L. & Galizzi, A. The out B gene of *Bacillus subtilis* codes for NAD+ synthetase. *J. Biological Chemistry* 270, 6181–6185). Crystals were grown by vapor diffision at 28° C. from 21–23% polyethylene glycol (PEG) 400, 100 mM acetate buffer, pH 5.2, 50 mM $MgCl_2$, 2.5 mM β-mercapto ethanol. Inhibitors were dissolved in minimal volume of PEG 400 and then mixed with crystallization medium to final concentration of 5–10 mM in 23% v/v PEG 400. 10 μl of protein solution (16 mg/ml in crystallization buffer) were mixed with 10 μL of inhibitor in crystallization medium incubated at 28° C. The crystals of NAD synthetase complexed with inhibitors obtained belonged to space group P21 as described previously in the literature. (Rizzi, M., Nessi, C., Matteve, A., Coda, A. & Galizzi, A. Crystal structure of $NH_3$-dependent NAD+ synthetase from *Bacillus subtilis*. *EMBO Journal* 15, 5125–5134 (1996)).

B. Data collection. Diffraction data for the different complexes of NAD synthetase with inhibitors were collected at ambient temperature or at 120° K with use of R-axisII and R-axisIV image plates and a rotating anode X-ray source, using Xstream Cryosystem device. Data were processed with DENZO and SCALEPACK as described. (Otwinowski, Z., & Minor, W. Processing of X-ray data collected in oscillation mode, in Carter C. W Jr. and Sweet M. M (eds.), Methods of Enzymology, v. 76, 307–326, Academic Press, New York (1996)). All subsequent calculations were performed with CCP4 program suite. (CCP4. The SERC (UK) Collaborative Computing Project No. 4, A suite of programs for Protein Crystallography, SERC Daresbury Laboratory, Warrington, UK, 1979.)

C. Refinement. All complexes of NAD synthetase with inhibitors were isomorphous with the recently solved structure NAD synthetase complexed with AMP, PPi, ATP and $Mg^{2+}$ (Rizzi, M., Nessi, C., Bolognesi, M., Coda, A. & Galizzi, A. Crystallization of EVADE synthetase from *Bacillus subtilis*. *Proteins* 26, 236–238 (1996). The coordinates from this structure excluding ligands and water molecules were used as a starting model for the free enzyme at 2.0 A resolution. Rigid-body refinement followed by simulated annealing were carried out with X-PLOR (Brunger, A. T., *X-PLOR Version 3.1. A system for X-ray Crystallography and NMR* (Yale Univ Press, New Haven, Conn., 1992)) until convergence was reached using all reflections to 2.0 A resolution. The model of the free enzyme was subsequently used for phasing and refinement of the complexes of NAD synthetase with inhibitors. The procedure for refinement with X-PLOR of a particular model included first simulated annealing cycle and positional refinement of the protein. Inhibitors were manually built into $(F_o-F_c)\alpha_c$ difference Fourier maps using QUANTA (Molecular Simulations) (Jones, T., Zou, J., Cowan, S. & Kjeldgaard, M. Improved method for building protein models in electron density maps and the location of the errors in these models. *Acta Crystallogr. A* 47, 110–119 (1991)) and O and refinement continued. A bulk solvent correction were then applied and ordered water molecules added following standard criteria.

Example 7

"One-at-a-Time" In-vitro Screening Method

The "one-at-a-time" in vitro bacterial NAD synthetase enzyme activity assay described below was used to test for relative activities of selected active molecules and synthetic dimers. The method was used to test selected NAD synthetase inhibitor compounds of the library herein, as well as commercially available compounds predicted to have bacterial NAD synthetase enzyme activity inhibitor capabilities.

A solution (1014 L) of 60 mM HEPPS pH 8.5 with 20 mM KCl was prepared containing the following species: 0.210 mM ATP, 0.152 mM NaAD, 4 mM $MgCl_2$, 10 mM $NH_4Cl$, 0.21 mg/mL ADH, and 1% ETOH. A stock solution of test inhibitors was then prepared by dissolving solid samples into 100% DMSO. 20 L of the test compound stock solution was then added to the mixture to give the final test compound concentrations listed. To start the enzyme assay, 16 L of a 65 g/mL NAD Synthetase solution were added, the mixture was mixed three times, and the absorbance at 340 nm was then monitored kinetically for 400 s using an Aviv 14DS UV-Vis spectrophotometer. The initial kinetics trace from 30 to approximately 250 seconds after enzyme addition was then fitted to a straight line using linear regression, and this rate was then compared to that of a control containing no inhibitor, using the following formula to calculate % Inhibition: $\{(Vo-V)/Vo\}*100\%$, where Vo is the rate of the reaction with no test compound present and V is the rate of the reaction with test the test compound added. Each compound was tested in triplicate, and the resulting values for % inhibition were averaged to give the listed value. $IC_{50}$ values were obtained for select compounds by assaying six different concentrations of test compound, in triplicate, at concentrations between 0.0 and 2.0 mM, and plotting the resulting % inhibition values against the −LOG of the test compound dose to reveal the concentration at which 50% inhibition was observed.

Example 8

Comparison of Bacterial NAD Synthetase Activity in Different Bacteria Types

To determine initially if a compound found active in the assays, Compound 864, was also an effective inhibitor of a variety of different bacteria, a standard antibiotic assay was performed. The results are summarized in Table 306. In this assay 250 μg of Compound 864 (25 μg/ml in DMSO) was spotted on 6 or 7 mm paper disks. Each disk was placed on separate 30 ml solid-medium plates layered with bacteria Blood agar plates were used for Streptococcus, and minimal-glucose plates were used for the other microorganisms in Table 306. DMSO controls provided negative results.

TABLE 306

INHIBITION OF GRAM +/- BACTERIA BY COMPOUND 864

| BACTERIUM | STRAIN | GRAM + OR − | ZONE OF INHIBITION (mm) |
|---|---|---|---|
| Escherichia coli K-12 | MG1655 (CGSC#6300) | − | 9.5 |
| Escherichia coli K-12 | W3110 (CGSC#4474) | − | 9.5 |
| Salmonella typhimurium | LT2 TT366 | − | 10 |
| Streptococcus pneumonia | D39 | + | 12 |
| Streptococcus pneumoniae | WU2 | + | 15 |
| Bacillus subtilis | A700 | + | 19.5 |

Compound 864 demonstrates inhibitory activity from which bacterial NAD synthetase inhibitory activity in a variety of bacteria may be extrapolated. Further, it is evident from this data that inhibition of bacterial NAD synthetase enzyme corresponds to inhibition of both gram positive and gram negative bacteria. Such data also demonstrates the effectiveness of the compounds herein as bacteriacidal agents, antimicrobial agents and disinfectants.

Example 9

Adaptation of Enzyme Assay to High Through-put Screening of Inhibitors

The enzyme kinetics assay for bacterial NAD synthetase enzyme inhibitory activity utilized as the primary biological screen, discussed previously as the "one-at-a-time" in vitro assay, was adapted to a microtiter plate format so that many compounds could be screened in a short time i.e., in a high-throughput system.

The final reaction mixture included 0.2 ml of 60 mM HEPPS buffer, pH 8.5, 10 mM $MgCl_2$, 19 mM $NH_4Cl_2$, 20 mM KCl, 0.1 mM NaAD, 0.3% n-Octyl-D-Glucopyranoside, 1% ethanol, 1 g/ml NAD synthetase, 62.5 g/ml yeast alcohol dehydrogenase, 0.2 mM ATP and 2.5% DMSO.

The measurement of inhibitory activities of the test compounds-was conducted using a high through-put screening system (HTS system). The HTS system utilizes an integrated Sagian 2M ORCA robotic system coordinating the functions of a Beckmnan Biomek 2000 liquid handler and a Molecular Devices SpectraMax Plus spectrophotometer. The 2M ORCA robotic station was responsible for the movement of all hardware and the integration of multiple stations on the worksurface. The Biomek 2000 is programmed to perform all phases of liquid dispensing and mixing. The SpectraMax Plus spectrophotometer was equipped to monitor absorbance in a 96-well plate format.

The present assay was designed for a 96-well plate format and begun with the dispensing of 0.170 ml of reaction buffer containing 60 mM HEPPS buffer, pH 8.5, 10 mM $MgCl_2$, 19 mM $NH_4Cl_2$, 20 mM KCl, 0.118 mM NaAD, 0.3% n-Octyl-D-Glucopyranoside, 1.18% ethanol, 1.18 g/ml NAD synthetase, and 73.75 g/ml yeast alcohol dehydrogenase. Once the Biomek 2000 has completed this stage of the liquid handling, a 0.005 ml volume of test compound in 100% DMSO or a 0.005 ml of DMSO was dispensed in the reaction well. The Biomek 2000 mixed these components utilizing a predefined mixing program. The reaction was initiated by the addition of 0.025 ml of a solution of 1.6 mM ATP dissolved in 60 mM HEPPS buffer, pH 8.5, 10 mM $MgCl_2$, 19 mM $NH_4Cl_2$, 20 mM KCl, 2.5% DMSO, and 0.3% n-Octyl-D-Glucopyranoside. The reactions were monitored by measuring the increase in absorbance at 304 nm. The linear portion of the reaction was monitored for 180 sec. The initial velocity was determined using Softmax Pro, the software supplied with the Molecular Devices SpectraMax Plus spectrophotometer.

The compounds were supplied as a stock with a concentration of 50 mM dissolved in 100% DMSO. An initial screen was conducted on all compounds using a 2 or 3 concentration screen. The 2 panel screen used concentrations of 0.2 mM and 0.1 MM for the compounds. The 3 panel screen used concentrations of 0.2 mM, 0.1 mM, and 0.05 mM. From the initial screen, lead compounds which indicated the greatest inhibitory capacity were then subjected to a wider screen of concentrations (0.1 mM to 0.005 mM) to determine the apparent IC-50 values for each compound.

Double reciprocal plots of initial velocities have yielded the kinetic parameters given in the following table for the 2 mL cuvette assay. Also included in the table are the Km values obtained in the 0.2 mL microtiter plate assay. In this latter assay, a Beckianan/Sagian automated robotic system was applied in for high through-put screening in one preferred embodiment of the method.

TABLE 308

KINETIC DATA FOR HIGH THROUGH-PUT SCREENING METHOD

| | 2 mL Assay | | 0.2 mL Assay |
|---|---|---|---|
| Substrate | Km (mM) | Vmax (nM/sec) | Km (mM) |
| $Mg^{+2}$ | 2.6 | 120 | 2.9 |
| $NH_3$ | 2.88 | 137 | — |
| ATP | 0.12 | 436 | 0.152 |
| NaAD | 0.075 | 286 | 0.076 |

With the preferred high through-put system and the adapted enzymatic screening assay for bacterial NAD synthetase inhibitory enzyme activity described previously, large numbers of compounds can be screened in a short period.

Example 10

NAD Synthetase Inhibitory Activity of Compounds

Compounds of the libraries herein were screened using the high through-put enzyme kinetics assays described above in Example 9. Tables 310, 312A, 312B, 314 and 316 below present NAD synthetase enzyme inhibition data for a number of compounds of the libraries herein tested at 0.25 mM, 0.2 mM, 0.1 mM and 0.05 mM doses, respectively.

TABLE 310

COMPOUND ACTIVITIES AT 0.25 mM

| COMPOUND NUMBER | % INHIBITION |
|---|---|
| 868 | 13.5 |
| 870 | 63.1 |
| 871 | 81.9 |
| 873 | 98.0 |
| 874 | 97.0 |
| 877 | 98.3 |
| 880 | 96.7 |
| 885 | 98.0 |

TABLE 310-continued

COMPOUND ACTIVITIES AT 0.25 mM

| COMPOUND NUMBER | % INHIBITION |
|---|---|
| 888 | 99.0 |
| 891 | 99.9 |
| 892 | 97.7 |
| 893 | 13.8 |
| 895 | 95.7 |
| 897 | 50.9 |
| 898 | 51.8 |
| 900 | 84.9 |
| 901 | 32.8 |
| 903 | 95.5 |
| 907 | 20.6 |
| 910 | 88.5 |
| 912 | 27.6 |
| 913 | 7.6 |
| 915 | 95.7 |
| 917 | 88.9 |
| 918 | 98.6 |
| 919 | 90.2 |
| 922 | 87.4 |
| 927 | 93.1 |
| 928 | 85.8 |
| 930 | 96.7 |
| 931 | 15.8 |
| 933 | 99.2 |
| 934 | 98.5 |
| 937 | 88.8 |
| 938 | 98.8 |
| 939 | 97.8 |
| 940 | 88.7 |

TABLE 312A

COMPOUND ACTIVITIES AT 0.2 mM

| Compound Number | % Inhibition |
|---|---|
| 6 | 5.67 |
| 9 | 28.02 |
| 13 | 80.80 |
| 14 | 78.85 |
| 23 | 27.12 |
| 164 | 5.47 |
| 165 | 90.97 |
| 166 | 87.68 |
| 173 | 73.86 |
| 213 | 90.67 |
| 222 | 52.98 |
| 227 | 91.19 |
| 236 | 9.59 |
| 238 | 38.21 |
| 246 | 92.19 |
| 254 | 73.91 |
| 262 | 88.76 |
| 267 | 26.97 |
| 268 | 11.23 |
| 284 | 13.92 |
| 285 | 32.45 |
| 287 | 16.01 |
| 289 | 9.28 |
| 291 | 71.94 |
| 292 | 44.36 |
| 293 | 87.66 |
| 296 | 16.79 |
| 299 | 49.13 |
| 300 | 11.79 |
| 301 | 6.12 |
| 302 | 21.48 |
| 303 | 50.56 |
| 305 | 54.83 |
| 306 | 33.93 |
| 307 | 4.40 |
| 308 | 33.71 |

TABLE 312A-continued

COMPOUND ACTIVITIES AT 0.2 mM

| Compound Number | % Inhibition |
|---|---|
| 310 | 38.29 |
| 311 | 29.67 |
| 318 | 14.94 |
| 322 | 14.40 |
| 323 | 28.08 |
| 324 | 34.99 |
| 329 | 30.77 |
| 330 | 23.96 |
| 334 | 41.67 |
| 335 | 3.28 |
| 339 | 42.87 |
| 341 | 3.54 |
| 342 | 11.92 |
| 343 | 10.82 |
| 344 | 4.58 |
| 348 | 44.42 |
| 351 | 65.08 |
| 354 | 2.96 |
| 355 | 2.08 |
| 356 | 1.95 |
| 357 | 67.58 |
| 358 | 23.19 |
| 359 | 35.55 |
| 360 | 3.46 |
| 363 | 75.01 |
| 364 | 29.20 |
| 365 | 16.45 |
| 367 | 9.72 |
| 369 | 35.33 |
| 370 | 41.34 |
| 371 | 43.85 |
| 373 | 14.13 |
| 377 | 30.12 |
| 379 | 6.27 |
| 380 | 10.09 |
| 382 | 42.85 |
| 383 | 2.76 |
| 384 | 4.10 |
| 385 | 61.62 |
| 386 | 28.75 |
| 388 | 25.86 |
| 389 | 12.44 |
| 392 | 10.89 |
| 394 | 4.62 |
| 399 | 15.22 |
| 401 | 14.26 |
| 403 | 5.07 |
| 405 | 6.07 |
| 406 | 10.96 |
| 407 | 24.14 |
| 408 | 7.04 |
| 409 | 19.02 |
| 410 | 8.77 |
| 411 | 8.84 |
| 413 | 4.76 |
| 414 | 6.91 |
| 415 | 7.72 |
| 417 | 14.59 |
| 418 | 5.95 |
| 419 | 24.28 |
| 420 | 9.16 |
| 421 | 1.86 |
| 422 | 16.23 |
| 423 | 12.09 |
| 425 | 19.12 |
| 428 | 26.53 |
| 429 | 13.01 |
| 430 | 1.20 |
| 431 | 10.77 |
| 432 | 13.21 |
| 434 | 5.36 |
| 435 | 17.24 |
| 436 | 11.57 |
| 437 | 6.91 |
| 438 | 9.45 |

TABLE 312A-continued

COMPOUND ACTIVITIES AT 0.2 mM

| Compound Number | % Inhibition |
|---|---|
| 440 | 12.69 |
| 441 | 11.80 |
| 443 | 5.51 |
| 445 | 5.43 |
| 446 | 13.78 |
| 447 | 2.30 |
| 448 | 2.92 |
| 449 | 8.67 |
| 450 | 7.90 |
| 452 | 20.04 |
| 454 | 7.95 |
| 455 | 2.69 |
| 457 | 3.31 |
| 458 | 15.72 |
| 460 | 4.17 |
| 461 | 17.92 |
| 462 | 3.84 |
| 464 | 13.50 |
| 465 | 7.92 |
| 466 | 5.79 |
| 467 | 15.08 |
| 473 | 15.06 |
| 474 | 2.45 |
| 476 | 17.49 |
| 477 | 10.15 |
| 478 | 9.76 |
| 482 | 17.07 |
| 483 | 7.31 |
| 484 | 39.95 |
| 486 | 4.97 |
| 488 | 17.65 |
| 489 | 5.87 |
| 490 | 2.96 |
| 491 | 8.24 |
| 492 | 2.59 |
| 493 | 9.12 |
| 494 | 17.44 |
| 495 | 6.80 |
| 496 | 36.97 |
| 497 | 29.10 |
| 498 | 47.31 |
| 499 | 25.59 |
| 501 | 4.98 |
| 502 | 44.08 |
| 503 | 37.04 |
| 505 | 25.51 |
| 506 | 21.74 |
| 507 | 26.18 |
| 508 | 51.84 |
| 509 | 78.00 |
| 510 | 20.99 |
| 511 | 11.02 |
| 512 | 17.50 |
| 513 | 23.66 |
| 514 | 22.32 |
| 515 | 30.39 |
| 516 | 29.95 |
| 517 | 34.72 |
| 519 | 16.27 |
| 520 | 55.83 |
| 521 | 29.59 |
| 522 | 35.74 |
| 523 | 18.12 |
| 524 | 30.81 |
| 525 | 8.39 |
| 526 | 42.77 |
| 527 | 73.78 |
| 528 | 65.81 |
| 529 | 15.50 |
| 530 | 20.52 |
| 531 | 36.55 |
| 532 | 53.80 |
| 533 | 24.68 |
| 534 | 26.99 |
| 535 | 12.61 |
| 536 | 32.49 |
| 537 | 10.69 |
| 538 | 40.95 |
| 539 | 16.80 |
| 540 | 20.20 |
| 542 | 15.89 |
| 543 | 28.06 |
| 544 | 19.66 |
| 545 | 32.18 |
| 549 | 14.08 |
| 550 | 28.18 |
| 551 | 50.05 |
| 555 | 30.89 |
| 557 | 10.46 |
| 558 | 1.27 |
| 559 | 33.24 |
| 560 | 46.91 |
| 561 | 24.70 |
| 562 | 46.44 |
| 563 | 22.68 |
| 564 | 26.95 |
| 565 | 15.63 |
| 566 | 29.72 |
| 567 | 22.51 |
| 568 | 18.95 |
| 569 | 34.84 |
| 571 | 17.47 |
| 572 | 31.02 |
| 573 | 26.24 |
| 574 | 11.95 |
| 575 | 42.01 |
| 576 | 2.05 |
| 577 | 20.58 |
| 578 | 30.96 |
| 579 | 12.57 |
| 581 | 21.66 |
| 582 | 6.13 |
| 583 | 31.37 |
| 584 | 68.79 |
| 585 | 17.43 |
| 586 | 2.01 |
| 587 | 56.47 |
| 588 | 2.49 |
| 590 | 28.82 |
| 591 | 18.59 |
| 592 | 18.70 |
| 593 | 60.19 |
| 594 | 2.77 |
| 595 | 17.94 |
| 596 | 56.49 |
| 597 | 19.76 |
| 598 | 43.33 |
| 599 | 19.31 |
| 600 | 3.10 |
| 601 | 2.22 |
| 602 | 59.10 |
| 603 | 51.72 |
| 604 | 34.10 |
| 605 | 68.65 |
| 608 | 6.75 |
| 611 | 15.13 |
| 614 | 8.32 |
| 617 | 2.02 |
| 619 | 19.53 |
| 620 | 19.03 |
| 627 | 11.19 |
| 630 | 10.72 |
| 636 | 17.36 |
| 640 | 1.45 |
| 645 | 4.31 |
| 648 | 5.82 |
| 653 | 20.59 |
| 654 | 2.11 |
| 659 | 25.47 |
| 662 | 8.39 |

TABLE 312A-continued

COMPOUND ACTIVITIES AT 0.2 mM

| Compound Number | % Inhibition |
|---|---|
| 663 | 15.43 |
| 672 | 2.63 |
| 673 | 1.81 |
| 682 | 6.65 |
| 685 | 7.81 |
| 697 | 4.28 |
| 700 | 2.54 |
| 712 | 12.59 |
| 740 | 7.23 |
| 741 | 30.47 |
| 742 | 28.20 |
| 744 | 95.85 |
| 745 | 85.38 |
| 760 | 2.28 |
| 761 | 6.88 |
| 762 | 40.05 |
| 763 | 66.50 |
| 764 | 79.25 |
| 862 | 9.05 |
| 864 | 19.33 |
| 865 | 46.43 |
| 867 | 70.33 |
| 967 | 19.51 |
| 968 | 88.52 |
| 969 | 83.16 |
| 970 | 96.65 |
| 979 | 38.72 |
| 980 | 74.86 |
| 981 | 95.16 |
| 982 | 93.74 |
| 990 | 92.16 |

TABLE 312B

Activities of compounds at 0.2 mM

| Compound No | % Inhibition |
|---|---|
| 995 | 27 |
| 1012 | 2 |
| 1013 | 29 |
| 1014 | 14 |
| 1015 | 15 |
| 1016 | 29 |
| 1017 | 23 |
| 1018 | 17 |
| 1019 | 3 |
| 1020 | 8 |
| 1024 | 45 |
| 1025 | 15 |
| 1026 | 23 |
| 1027 | 2 |
| 1030 | 17 |
| 1031 | 23 |
| 1034 | 30 |
| 1036 | 6 |
| 1038 | 22 |
| 1039 | 30 |
| 1040 | 3 |
| 1045 | 14 |
| 1046 | 2 |
| 1047 | 45 |
| 1053 | 72 |
| 3054 | 86 |
| 1055 | 46 |
| 1056 | 18 |
| 1057 | 59 |
| 1058 | 18 |
| 1059 | 85 |
| 1060 | 19 |
| 1061 | 61 |
| 1062 | 18 |

TABLE 312B-continued

Activities of compounds at 0.2 mM

| Compound No | % Inhibition |
|---|---|
| 1063 | 32 |
| 1064 | 92 |
| 1065 | 81 |
| 1066 | 70 |
| 1067 | 28 |
| 1068 | 92 |
| 1069 | 36 |
| 1070 | 82 |
| 1071 | 55 |
| 1073 | 78 |
| 1074 | 91 |
| 1075 | 79 |
| 1076 | 74 |
| 1077 | 73 |
| 1078 | 68 |
| 1079 | 97 |
| 1080 | 83 |
| 1081 | 84 |
| 1082 | 81 |
| 1084 | 106 |
| 1085 | 87 |
| 1086 | 81 |
| 1087 | 61 |
| 1088 | 100 |
| 1089 | 56 |
| 1090 | 96 |
| 1091 | 74 |
| 1092 | 60 |
| 1093 | 66 |
| 1095 | 161 |
| 1096 | 140 |
| 1097 | 98 |
| 1098 | 75 |
| 1099 | 67 |
| 1105 | 167 |

TABLE 314

COMPOUND ACTIVITIES AT 0.1 mM

| Compound Number | % Inhibition |
|---|---|
| 989 | 54.83 |
| 988 | 84.32 |
| 978 | 80.31 |
| 977 | 87.61 |
| 976 | 70.96 |
| 975 | 55.17 |
| 974 | 88.21 |
| 973 | 97.77 |
| 972 | 96.76 |
| 971 | 100.00 |
| 965 | 8.48 |
| 943 | 21.38 |
| 942 | 97.79 |
| 941 | 100.00 |
| 936 | 97.75 |
| 924 | 97.67 |
| 921 | 96.65 |
| 909 | 97.17 |
| 904 | 47.68 |
| 894 | 91.13 |
| 889 | 93.60 |
| 886 | 94.50 |
| 882 | 94.50 |
| 881 | 90.89 |
| 879 | 99.58 |
| 878 | 96.43 |
| 876 | 95.41 |
| 875 | 93.56 |
| 872 | 98.31 |
| 853 | 73.46 |

TABLE 314-continued

COMPOUND ACTIVITIES AT 0.1 mM

| Compound Number | % Inhibition |
|---|---|
| 850 | 87.46 |
| 849 | 90.92 |
| 848 | 70.02 |
| 832 | 78.64 |
| 831 | 26.21 |
| 769 | 98.31 |
| 768 | 98.64 |
| 767 | 95.96 |
| 766 | 91.22 |
| 765 | 89.99 |
| 749 | 98.19 |
| 748 | 98.38 |
| 747 | 97.81 |
| 746 | 91.27 |
| 743 | 94.10 |
| 715 | 20.73 |
| 676 | 1.46 |
| 670 | 4.65 |
| 638 | 2.31 |
| 637 | 4.42 |
| 589 | 24.98 |
| 556 | 18.19 |
| 554 | 68.22 |
| 553 | 49.49 |
| 552 | 15.24 |
| 548 | 24.59 |
| 547 | 8.32 |
| 546 | 4.72 |
| 541 | 10.26 |
| 518 | 30.39 |
| 500 | 18.25 |
| 487 | 9.88 |
| 472 | 12.76 |
| 451 | 2.94 |
| 444 | 8.55 |
| 439 | 2.57 |
| 433 | 1.79 |
| 426 | 5.49 |
| 402 | 4.71 |
| 397 | 4.51 |
| 396 | 3.64 |
| 395 | 20.85 |
| 387 | 29.97 |
| 381 | 25.05 |
| 376 | 37.32 |
| 375 | 60.14 |
| 374 | 31.84 |
| 373 | 7.72 |
| 368 | 21.10 |
| 362 | 8.31 |
| 361 | 16.08 |
| 355 | 3.31 |
| 352 | 32.69 |
| 349 | 86.56 |
| 346 | 42.57 |
| 345 | 37.00 |
| 344 | 54.05 |
| 344 | 10.78 |
| 338 | 27.28 |
| 337 | 35.94 |
| 336 | 18.02 |
| 333 | 26.29 |
| 332 | 12.27 |
| 328 | 47.85 |
| 327 | 55.31 |
| 326 | 16.11 |
| 325 | 53.22 |
| 321 | 37.25 |
| 320 | 44.72 |
| 319 | 16.99 |
| 317 | 25.04 |
| 316 | 41.58 |
| 315 | 77.23 |
| 314 | 9.19 |
| 313 | 27.37 |

TABLE 314-continued

COMPOUND ACTIVITIES AT 0.1 mM

| Compound Number | % Inhibition |
|---|---|
| 312 | 10.25 |
| 309 | 41.47 |
| 304 | 29.48 |
| 297 | 50.83 |
| 295 | 25.05 |
| 290 | 12.89 |
| 288 | 42.38 |
| 269 | 51.12 |
| 245 | 7.01 |
| 230 | 93.06 |
| 229 | 99.35 |
| 228 | 95.08 |
| 214 | 82.84 |
| 182 | 95.41 |
| 154 | 9.24 |
| 82 | 9.68 |
| 12 | 62.22 |

TABLE 316

COMPOUND ACTIVITIES AT 0.05 mM

| Compound Number | % Inhibition |
|---|---|
| 944 | 2.06 |
| 948 | 2.52 |
| 950 | 7.32 |
| 960 | 6.37 |
| 964 | 1.18 |
| 966 | 8.25 |
| 983 | 92.49 |
| 984 | 87.50 |
| 985 | 92.14 |
| 986 | 30.80 |

Tables 318A mad 318B set out $IC_{50}$ values for compounds of the invention herein. Table 318A sets out values for the various potent compounds ("lead compounds") of the NAD synthetase enzyme inhibitor compound libraries disclosed herein. Table 318B sets out values for a number of compounds of the invention herein, some of which are also considered to be potent compounds. The potency of the compounds is expressed according to $IC_{50}$ values. The $IC_{50}$ value is that amount of NAD synthetase enzyme inhibitor compound required to inhibit the enzyme by 50%.

TABLE 318A

IC 50 DATA
LEAD COMPOUNDS

| Compound Number | IC 50 ($\mu$M) |
|---|---|
| 13 | 50 |
| 174 | 40 |
| 182 | 60 |
| 190 | 50 |
| 213 | 65 |
| 214 | 30 |
| 228 | 60 |
| 229 | 25 |
| 230 | 12.5 |
| 270 | 60 |
| 315 | 100 |
| 349 | 75 |
| 745 | 85 |
| 746 | 50 |
| 747 | 70 |

TABLE 318A-continued

IC 50 DATA LEAD COMPOUNDS

| Compound Number | IC 50 ($\mu$M) |
|---|---|
| 748 | 30 |
| 749 | 25 |
| 765 | 90 |
| 766 | 65 |
| 767 | 60 |
| 768 | 30 |
| 769 | 20 |
| 832 | 90 |
| 848 | 90 |
| 849 | 70 |
| 850 | 80 |
| 853 | 45 |
| 869 | 40 |
| 872 | 50 |
| 875 | 45 |
| 876 | 75 |
| 878 | 80 |
| 879 | 40 |
| 882 | 90 |
| 884 | 45 |
| 886 | 80 |
| 887 | 25 |
| 889 | 75 |
| 891 | 80 |
| 894 | 50 |
| 906 | 25 |
| 909 | 25 |
| 917 | 60 |
| 921 | 25 |
| 924 | 25 |
| 936 | 60 |
| 939 | 25 |
| 941 | 50 |
| 942 | 75 |
| 970 | 55 |
| 972 | 40 |
| 973 | 45 |
| 974 | 35 |
| 975 | 38 |
| 976 | 20 |
| 977 | 10 |
| 981 | 60 |
| 982 | 60 |
| 983 | 25 |
| 984 | 20 |
| 985 | 15 |
| 986 | 10 |
| 988 | 10 |
| 990 | 20 |

TABLE 318B

IC$_{50}$ DATA FOR SELECTED COMPOUNDS

| COMPOUND NUMBER | IC$_{50}$ of Compounds ($\mu$M) |
|---|---|
| 1031 | 36.3 |
| 1064 | 37.5 |
| 1065 | 37.5 |
| 1068 | 62.5 |
| 1070 | 36.2 |
| 1074 | 30 |
| 1075 | 65 |
| 1076 | 135 |
| 1078 | 122.5 |
| 1079 | 36.2 |
| 1080 | 100 |
| 1081 | 67.5 |
| 1082 | 50 |
| 1084 | 12.5 |
| 1085 | 137.5 |
| 1086 | 27.5 |
| 1087 | 40 |
| 1090 | 21.2 |
| 1095 | 100 |
| 1096 | 68.9 |
| 1097 | 63.7 |
| 1099 | 100 |
| 1104 | 61 |

Table 320 sets out screening results for a selection of compounds from the libraries of bacterial NAD synthetase enzyme inhibitor compounds of the invention herein. As apparent firm the table, all compounds tested exhibit some inhibitory activity against *Staphylococcus epidermitis* and, accordingly, the compounds exhibit effectiveness as antimicrobial agents, antibacterial agents and disinfecting agents.

TABLE 320

**SCREENING RESULTS OF NAD SYNTHETASE INHIBITOR COMPOUNDS AGAINST *S. EPIDERMITIS***
(Sorted by Percent Inhibition)

| Compound Number | Concentration Screened | % Inhibition |
|---|---|---|
| 237 | 10 uM | 100.00 |
| 593 | 100 uM | 100.00 |
| 587 | 100 uM | 100.00 |
| 518 | 100 uM | 100.00 |
| 375 | 100 uM | 100.00 |
| 374 | 100 uM | 100.00 |
| 369 | 100 uM | 100.00 |
| 363 | 100 uM | 100.00 |
| 362 | 100 uM | 100.00 |
| 357 | 100 uM | 100.00 |
| 339 | 100 uM | 100.00 |
| 333 | 100 uM | 100.00 |
| 327 | 100 uM | 100.00 |
| 321 | 100 uM | 100.00 |
| 315 | 100 uM | 100.00 |
| 303 | 100 uM | 100.00 |
| 297 | 100 uM | 100.00 |
| 291 | 100 uM | 100.00 |
| 345 | 100 uM | 99.86 |
| 809 | 10 uM | 99.81 |
| 512 | 100 uM | 99.71 |
| 288 | 10 uM | 99.65 |
| 524 | 100 uM | 99.57 |
| 351 | 100 uM | 99.57 |
| 254 | 10 uM | 99.39 |
| 238 | 10 uM | 99.39 |
| 839 | 10 uM | 99.35 |
| 12 | 10 uM | 99.22 |
| 500 | 100 uM | 99.14 |
| 309 | 100 uM | 99.07 |
| 835 | 10 uM | 99.03 |
| 851 | 10 uM | 98.90 |
| 841 | 10 uM | 98.90 |
| 840 | 10 uM | 98.77 |
| 749 | 100 uM | 98.73 |
| 174 | 10 uM | 98.71 |
| 506 | 100 uM | 98.64 |
| 829 | 10 uM | 98.64 |
| 853 | 10 uM | 98.58 |
| 852 | 10 uM | 98.58 |
| 14 | 10 uM | 98.58 |
| 285 | 100 uM | 98.57 |
| 13 | 10 uM | 98.54 |

TABLE 320-continued

SCREENING RESULTS OF NAD SYNTHETASE INHIBITOR COMPOUNDS AGAINST *S. EPIDERMITIS*
(Sorted by Percent Inhibition)

| Compound Number | Concentration Screened | % Inhibition |
| --- | --- | --- |
| 222 | 10 uM | 98.50 |
| 560 | 100 uM | 98.43 |
| 381 | 100 uM | 98.43 |
| 748 | 100 uM | 98.38 |
| 173 | 10 uM | 98.30 |
| 566 | 100 uM | 98.21 |
| 214 | 100 uM | 98.13 |
| 834 | 10 uM | 98.13 |
| 808 | 10 uM | 98.06 |
| 833 | 10 uM | 98.00 |
| 229 | 100 uM | 97.95 |
| 747 | 10 uM | 97.93 |
| 602 | 100 uM | 97.93 |
| 13 | 10 uM | 97.80 |
| 578 | 100 uM | 97.79 |
| 744 | 10 uM | 97.74 |
| 190 | 100 uM | 97.71 |
| 182 | 100 uM | 97.69 |
| 824 | 10 uM | 97.67 |
| 743 | 10 uM | 97.67 |
| 387 | 100 uM | 97.64 |
| 380 | 100 uM | 97.64 |
| 270 | 10 uM | 97.48 |
| 764 | 10 uM | 97.48 |
| 554 | 100 uM | 97.43 |
| 213 | 10 uM | 97.41 |
| 828 | 10 uM | 97.29 |
| 804 | 10 uM | 97.29 |
| 807 | 10 uM | 97.22 |
| 823 | 10 uM | 97.03 |
| 542 | 100 uM | 96.93 |
| 746 | 10 uM | 96.83 |
| 228 | 100 uM | 96.78 |
| 13 | 10 uM | 96.77 |
| 536 | 100 uM | 96.64 |
| 572 | 100 uM | 96.57 |
| 227 | 10 uM | 96.46 |
| 548 | 100 uM | 96.43 |
| 596 | 100 uM | 96.36 |
| 386 | 100 uM | 96.36 |
| 14 | 10 uM | 96.19 |
| 768 | 100 uM | 96.11 |
| 584 | 100 uM | 96.07 |
| 769 | 100 uM | 95.94 |
| 827 | 10 uM | 95.86 |
| 12 | 10 uM | 95.73 |
| 262 | 10 uM | 95.50 |
| 230 | 100 uM | 95.48 |
| 745 | 10 uM | 95.09 |
| 821 | 10 uM | 95.02 |
| 553 | 10 uM | 94.92 |
| 832 | 10 uM | 94.70 |
| 295 | 10 uM | 94.48 |
| 590 | 100 uM | 94.43 |
| 865 | 100 uM | 94.40 |
| 826 | 10 uM | 92.57 |
| 261 | 10 uM | 92.51 |
| 767 | 100 uM | 91.76 |
| 368 | 100 uM | 91.36 |
| 766 | 10 uM | 90.50 |
| 246 | 10 uM | 90.26 |
| 296 | 10 uM | 87.47 |
| 864 | 100 uM | 87.03 |
| 831 | 10 uM | 84.68 |
| 281 | 10 uM | 84.23 |
| 825 | 10 uM | 83.13 |
| 165 | 10 uM | 76.36 |
| 372 | 10 uM | 67.34 |
| 820 | 10 uM | 65.74 |
| 556 | 10 uM | 60.18 |
| 267 | 10 uM | 56.54 |
| 850 | 10 uM | 56.50 |
| 805 | 10 uM | 50.87 |
| 865 | 10 uM | 50.42 |
| 552 | 10 uM | 50.00 |
| 861 | 10 uM | 49.58 |
| 855 | 10 uM | 49.58 |
| 865 | 10 uM | 48.55 |
| 862 | 10 uM | 48.29 |
| 822 | 10 uM | 46.41 |
| 191 | 10 uM | 46.32 |
| 269 | 10 uM | 46.12 |
| 605 | 100 uM | 44.29 |
| 663 | 100 uM | 44.28 |
| 599 | 100 uM | 44.14 |
| 405 | 10 uM | 44.01 |
| 538 | 10 uM | 43.05 |
| 830 | 10 uM | 42.99 |
| 727 | 10 uM | 42.23 |
| 180 | 10 uM | 40.33 |
| 661 | 10 uM | 39.31 |
| 657 | 100 uM | 37.12 |
| 464 | 10 uM | 35.45 |
| 623 | 100 uM | 34.17 |
| 640 | 10 uM | 33.86 |
| 610 | 10 uM | 33.51 |
| 682 | 10 uM | 32.56 |
| 9 | 10 uM | 31.80 |
| 453 | 10 uM | 31.13 |
| 439 | 10 uM | 30.57 |
| 589 | 10 uM | 29.35 |
| 530 | 100 uM | 27.36 |
| 654 | 10 uM | 25.20 |
| 243 | 10 uM | 23.43 |
| 458 | 10 uM | 22.77 |
| 680 | 10 uM | 22.48 |
| 632 | 100 uM | 22.42 |
| 486 | 10 uM | 22.28 |
| 431 | 10 uM | 22.28 |
| 686 | 10 uM | 22.14 |
| 166 | 10 uM | 21.66 |
| 235 | 10 uM | 20.50 |
| 659 | 100 uM | 20.41 |
| 614 | 100 uM | 20.35 |
| 627 | 100 uM | 20.10 |
| 847 | 10 uM | 19.84 |
| 617 | 100 uM | 19.54 |
| 356 | 100 uM | 19.29 |
| 624 | 100 uM | 19.16 |
| 704 | 10 uM | 19.07 |
| 513 | 100 uM | 17.86 |
| 838 | 10 uM | 17.65 |
| 423 | 10 uM | 16.85 |
| 726 | 10 uM | 16.76 |
| 426 | 10 uM | 16.57 |
| 573 | 10 uM | 16.09 |
| 459 | 10 uM | 16.09 |
| 215 | 10 uM | 15.87 |
| 507 | 100 uM | 15.86 |
| 411 | 10 uM | 15.74 |
| 643 | 10 uM | 15.46 |
| 545 | 10 uM | 15.39 |
| 171 | 10 uM | 15.33 |
| 342 | 10 uM | 14.97 |
| 648 | 100 uM | 14.57 |
| 687 | 10 uM | 14.44 |
| 693 | 10 uM | 14.37 |
| 626 | 100 uM | 14.26 |
| 471 | 10 uM | 14.07 |
| 630 | 100 uM | 13.69 |
| 203 | 10 uM | 13.62 |
| 651 | 100 uM | 13.51 |
| 647 | 100 uM | 13.38 |
| 728 | 10 uM | 13.28 |

TABLE 320-continued

SCREENING RESULTS OF NAD SYNTHETASE INHIBITOR
COMPOUNDS AGAINST *S. EPIDERMITIS*
(Sorted by Percent Inhibition)

| Compound Number | Concentration Screened | % Inhibition |
|---|---|---|
| 709 | 10 uM | 12.94 |
| 665 | 100 uM | 12.75 |
| 620 | 100 uM | 12.69 |
| 631 | 10 uM | 12.19 |
| 677 | 100 uM | 12.12 |
| 437 | 10 uM | 11.84 |
| 615 | 100 uM | 11.81 |
| 621 | 100 uM | 11.75 |
| 655 | 10 uM | 11.51 |
| 675 | 100 uM | 11.37 |
| 519 | 10 uM | 11.35 |
| 669 | 100 uM | 11.24 |
| 445 | 10 uM | 11.21 |
| 491 | 10 uM | 11.14 |
| 476 | 10 uM | 11.14 |
| 618 | 100 uM | 11.06 |
| 492 | 10 uM | 11.00 |
| 684 | 10 uM | 10.83 |
| 638 | 100 uM | 10.55 |
| 612 | 100 uM | 10.24 |
| 529 | 10 uM | 10.15 |
| 634 | 10 uM | 10.08 |
| 690 | 10 uM | 10.01 |
| 608 | 100 uM | 9.86 |
| 422 | 10 uM | 9.82 |
| 611 | 100 uM | 9.67 |
| 392 | 10 uM | 9.61 |
| 562 | 10 uM | 9.44 |
| 765 | 10 uM | 9.31 |
| 683 | 10 uM | 9.26 |
| 199 | 10 uM | 9.26 |
| 645 | 100 uM | 9.23 |
| 200 | 10 uM | 9.20 |
| 606 | 100 uM | 9.17 |
| 432 | 10 uM | 8.91 |
| 642 | 100 uM | 8.86 |
| 598 | 10 uM | 8.86 |
| 531 | 10 uM | 8.77 |
| 440 | 10 uM | 8.77 |
| 65 | 10 uM | 8.66 |
| 653 | 100 uM | 8.42 |
| 729 | 10 uM | 8.24 |
| 452 | 10 uM | 8.22 |
| 641 | 100 uM | 8.10 |
| 465 | 10 uM | 8.08 |
| 344 | 10 uM | 8.08 |
| 622 | 10 uM | 7.97 |
| 501 | 100 uM | 7.93 |
| 503 | 10 uM | 7.82 |
| 417 | 10 uM | 7.80 |
| 625 | 10 uM | 7.77 |
| 24 | 10 uM | 7.76 |
| 449 | 10 uM | 7.73 |
| 412 | 10 uM | 7.73 |
| 650 | 100 uM | 7.73 |
| 674 | 10 uM | 7.70 |
| 443 | 10 uM | 7.66 |
| 350 | 10 uM | 7.59 |
| 635 | 100 uM | 7.47 |
| 450 | 10 uM | 7.45 |
| 639 | 100 uM | 7.41 |
| 609 | 100 uM | 7.35 |
| 236 | 10 uM | 7.29 |
| 394 | 10 uM | 7.03 |
| 710 | 10 uM | 6.95 |
| 636 | 100 uM | 6.72 |
| 706 | 10 uM | 6.68 |
| 629 | 100 uM | 6.66 |
| 455 | 10 uM | 6.55 |
| 406 | 10 uM | 6.41 |
| 225 | 10 uM | 6.40 |
| 326 | 10 uM | 6.27 |

TABLE 320-continued

SCREENING RESULTS OF NAD SYNTHETASE INHIBITOR
COMPOUNDS AGAINST *S. EPIDERMITIS*
(Sorted by Percent Inhibition)

| Compound Number | Concentration Screened | % Inhibition |
|---|---|---|
| 300 | 10 uM | 6.20 |
| 188 | 10 uM | 6.06 |
| 543 | 10 uM | 5.99 |
| 390 | 10 uM | 5.92 |
| 444 | 10 uM | 5.85 |
| 428 | 10 uM | 5.85 |
| 397 | 10 uM | 5.85 |
| 355 | 10 uM | 5.78 |
| 671 | 100 uM | 5.72 |
| 434 | 10 uM | 5.64 |
| 367 | 10 uM | 5.64 |
| 670 | 10 uM | 5.59 |
| 616 | 10 uM | 5.59 |
| 579 | 10 uM | 5.57 |
| 451 | 10 uM | 5.57 |
| 361 | 10 uM | 5.57 |
| 633 | 100 uM | 5.53 |
| 676 | 10 uM | 5.52 |
| 400 | 10 uM | 5.50 |
| 537 | 10 uM | 5.43 |
| 438 | 10 uM | 5.29 |
| 391 | 10 uM | 5.29 |
| 367 | 10 uM | 5.22 |
| 740 | 10 uM | 5.17 |
| 403 | 10 uM | 4.87 |
| 780 | 10 uM | 4.78 |
| 863 | 10 uM | 4.72 |
| 539 | 10 uM | 4.67 |
| 457 | 10 uM | 4.67 |
| 312 | 10 uM | 4.60 |
| 550 | 10 uM | 4.40 |
| 482 | 10 uM | 4.39 |
| 306 | 10 uM | 4.32 |
| 703 | 10 uM | 4.29 |
| 681 | 10 uM | 4.22 |
| 644 | 100 uM | 4.02 |
| 701 | 10 uM | 3.88 |
| 664 | 10 uM | 3.88 |
| 477 | 10 uM | 3.69 |
| 456 | 10 uM | 3.69 |
| 446 | 10 uM | 3.69 |
| 707 | 10 uM | 3.61 |
| 700 | 10 uM | 3.61 |
| 220 | 10 uM | 3.61 |
| 181 | 10 uM | 3.47 |
| 662 | 10 uM | 3.27 |
| 549 | 10 uM | 3.13 |
| 462 | 10 uM | 3.13 |
| 568 | 10 uM | 3.10 |
| 668 | 10 uM | 3.07 |
| 429 | 10 uM | 3.06 |
| 318 | 10 uM | 2.99 |
| 488 | 10 uM | 2.72 |
| 694 | 10 uM | 2.59 |
| 656 | 10 uM | 2.59 |
| 652 | 10 uM | 2.52 |
| 284 | 10 uM | 2.51 |
| 167 | 10 uM | 2.45 |
| 409 | 10 uM | 2.44 |
| 208 | 10 uM | 2.32 |
| 843 | 10 uM | 2.20 |
| 364 | 10 uM | 2.16 |
| 742 | 10 uM | 2.13 |
| 585 | 10 uM | 2.09 |
| 416 | 10 uM | 2.09 |
| 415 | 10 uM | 1.95 |
| 223 | 10 uM | 1.91 |
| 408 | 10 uM | 1.88 |
| 338 | 10 uM | 1.67 |
| 603 | 10 uM | 1.60 |
| 540 | 10 uM | 1.60 |
| 672 | 10 uM | 1.57 |

TABLE 320-continued

SCREENING RESULTS OF NAD SYNTHETASE INHIBITOR
COMPOUNDS AGAINST S. EPIDERMITIS
(Sorted by Percent Inhibition)

| Compound Number | Concentration Screened | % Inhibition |
|---|---|---|
| 219 | 10 uM | 1.57 |
| 396 | 10 uM | 1.53 |
| 373 | 10 uM | 1.53 |
| 673 | 10 uM | 1.50 |
| 658 | 10 uM | 1.43 |
| 613 | 10 uM | 1.36 |
| 483 | 10 uM | 1.25 |
| 424 | 10 uM | 1.11 |
| 646 | 10 uM | 1.09 |
| 698 | 10 uM | 1.02 |
| 359 | 100 uM | 1.01 |

Table 322 sets out the $MIC_{85}$ (minimum inhibitory concentration to achieve 85% inhibition) values against *B. subtilis* (gram positive bacteria) for a number of lead compounds within a library of bacterial NAD synthetase enzyme inhibitor compounds from Table 301 above and of the invention herein. This table demonstrates that the compounds of the invention herein are useful as antibacterial agents, antimicrobial agents and disinfecting agents.

TABLE 322

MIC85 RESULTS OF NAD SYNTHETASE
ENZYME INHIBITOR LEAD COMPOUNDS
AGAINST B. SUBTILLIS
(Sorted by MIC85)

| COMPOUND NUMBER | MIC85 ($\mu$M) |
|---|---|
| 769 | 3 |
| 749 | 3 |
| 977 | 10 |
| 986 | 10 |
| 988 | 10 |
| 990 | 10 |
| 230 | 10 |
| 976 | 10 |
| 985 | 10 |
| 984 | 30 |

Table 324 sets out the $MIC_{85}$ (minimum inhibitory concentration to achieve 85% inhibition) against *Staphylococcus epidermitis* for a number of compounds within a library of bacterial NAD synthetase enzyme inhibitor compounds of the invention herein. This table demonstrates that the compounds of the invention herein are useful as antibacterial agents, antimicrobial agents and disinfecting agents.

TABLE 324

$MIC_{85}$ RESULTS OF NAD SYNTHETASE ENZYME
INHIBITOR COMPOUNDS AGAINST S. EPIDERMITIS
(Sorted by $MIC_{85}$ Values)

| Compound Number | $MIC_{85}$ ($\mu$M) |
|---|---|
| 190 | 3 |
| 229 | 3 |
| 230 | 3 |
| 238 | 3.3 |
| 824 | 3.7 |
| 826 | 3.7 |
| 827 | 3.7 |
| 828 | 3.7 |

TABLE 324-continued $MIC_{85}$ RESULTS OF NAD SYNTHETASE ENZYME
INHIBITOR COMPOUNDS AGAINST S. EPIDERMITIS
(Sorted by $MIC_{85}$ Values)

| Compound Number | $MIC_{85}$ ($\mu$M) |
|---|---|
| 834 | 3.7 |
| 835 | 3.7 |
| 14 | 10 |
| 173 | 10 |
| 174 | 10 |
| 182 | 10 |
| 213 | 10 |
| 214 | 10 |
| 228 | 10 |
| 237 | 10 |
| 254 | 10 |
| 262 | 10 |
| 270 | 10 |
| 295 | 10 |
| 553 | 10 |
| 554 | 10 |
| 743 | 10 |
| 746 | 10 |
| 747 | 10 |
| 748 | 10 |
| 749 | 10 |
| 767 | 10 |
| 768 | 10 |
| 769 | 10 |
| 807 | 10 |
| 809 | 10 |
| 823 | 10 |
| 833 | 10 |
| 840 | 10 |
| 841 | 10 |
| 12 | 30 |
| 13 | 30 |
| 222 | 30 |
| 227 | 30 |
| 246 | 30 |
| 261 | 30 |
| 288 | 30 |
| 291 | 30 |
| 296 | 30 |
| 297 | 30 |
| 315 | 30 |
| 362 | 30 |
| 363 | 30 |
| 372 | 30 |
| 374 | 30 |
| 375 | 30 |
| 500 | 30 |
| 512 | 30 |
| 518 | 30 |
| 552 | 30 |
| 744 | 30 |
| 745 | 30 |
| 764 | 30 |
| 766 | 30 |
| 804 | 30 |
| 808 | 30 |
| 821 | 30 |
| 831 | 30 |
| 832 | 30 |
| 839 | 30 |
| 851 | 30 |
| 852 | 30 |
| 853 | 30 |

Example 11

In Vitro Toxicity in Human Cells of Selected Compounds Within the Library of Compounds Using the K562 human myeloid cell line, stock solutions of inhibitors in DMSO were added to the cell culture in RPMI 1640 medium which contained 10% fetal calf serum and was kept under a 10% $CO_2$ atmosphere. The final concentration of DMSO was less than 5%, and a DMSO control was included. The mixtures were incubated at doubling dilutions (approximately 1000 μM–10 μM range) of inhibitor for 15 hours at 37° C. At this time propidium iodide was added (1 μg/mL) and the mixture incubated at 30 min. at 4° C. The cells were washed once with medium, centrifuged, and resuspended in 2% bovine serum albumin/phosphate-buffered saline. The cell suspension was then run through a FAC Saliber flow cytometer and approximately 5000 cells were counted. The proportion of dead (stained) cells was determined, and the percent of live cells was expressed as % controls. The minimum toxic concentration was the lowest tested concentration of inhibitor which caused a significantly lower percentage of live cells as compared to controls.

TABLE 326

HUMAN CELL TOXICITY OF SELECTED LEAD COMPOUNDS

| Compound Number | Minimum Toxic Dose (μM) |
|---|---|
| 940 | 1000 |
| 949 | 200 |
| 951 | 500 |
| 409 | 200 |
| 948 | 200 |
| 270 | 200 |
| 939 | 500 |
| 947 | 200 |
| 953 | 100 |
| 274 | 300 |

It will be apparent to those skilled in the art that various modifications and variations can be made in the present invention without departing from the scope or spirit of the invention.

Throughout this application, where publications are referenced, the disclosures of these publications in their entireties are hereby incorporated by reference into this application in order to more fully describe the state of the art to which this invention pertains.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method of treating or preventing a microbial infection in a mammal comprising administering to the mammal a treatment effective or treatment preventive amount of a bacterial NAD synthetase enzyme inhibitor compound.

2. The method of claim 1 wherein the compound microbial infection is a bacterial infection.

3. The method of claim 1 wherein the bacterium is a gram negative or gram positive bacteria.

4. The method of claim 1 wherein the microbial infection comprises an infection caused by an antibiotic strain of bacteria.

5. The method of claim 1 comprising oral, rectal, intramuscularly, intravenous, intravesicular or topical administration.

6. The method of claim 1 wherein the compound is administered in a dosage of between about 0.1 to about 15 g per day and wherein the dosage is administered from about 1 to about 4 times per day.

7. The method of claim 1 further comprising administering a broad spectrum antibiotic.

8. A method of killing a prokaryote with an amount of prokaryotic NAD synthetase enzyme inhibitor to reduce or eliminate the production of NAD whereby the prokaryote is killed.

9. A method of decreasing prokaryotic growth, comprising contacting the prokaryote with an amount of a prokaryotic NAD synthetase enzyme inhibitor effective to reduce or eliminate the production of NAD whereby prokaryotic growth is decreased.

10. The method of claim 9 wherein the prokaryote is a bacterium.

11. The method of claim 10 wherein the bacterium is a gram negative or a gram positive bacteria.

12. The method of claim 9 wherein the prokaryote is an antibiotic resistant strain of bacteria.

13. The method of claim 9 wherein the NAD synthetase enzyme inhibitor is a compound that selectively binds with catalytic sites on a bacterial NAD synthetase enzyme to reduce or eliminate the production of NAD by the bacteria.

14. The method of claim 9 wherein the NAD synthetase enzyme inhibitor is a compound that selectively binds with catalytic sites on a bacterial NAD synthetase enzyme to reduce or eliminate the production of NAD by the bacteria.

15. The method of claim 9 wherein the administering step comprises oral, rectal, intramuscularly, intravenous, intravesicular or topical administration.

16. The method of claim 9 wherein the compound is administered in a dosage of between about 0.1 to about 15 g per day and wherein the dosage is administered from about 1 to about 4 times per day.

17. The method of claim 9, further comprising administering a broad spectrum antibiotic.

* * * * *